US011648265B2

(12) United States Patent
Sullivan et al.

(10) Patent No.: US 11,648,265 B2
(45) Date of Patent: May 16, 2023

(54) CELL THERAPY COMPOSITIONS AND METHODS OF USE THEREOF

(71) Applicant: Aurelius Biotherapeutics, LLC, Bellingham, WA (US)

(72) Inventors: Edmund Sullivan, Bellingham, WA (US); Theresa Westfall, Bellingham, WA (US)

(73) Assignee: Aurelius Biotherapeutics, LLC, Bellingham, WA (US)

( * ) Notice: Subject to any disclaimer, the term of this patent is extended or adjusted under 35 U.S.C. 154(b) by 249 days.

(21) Appl. No.: 16/320,729

(22) PCT Filed: Aug. 10, 2017

(86) PCT No.: PCT/US2017/046354
§ 371 (c)(1),
(2) Date: Jan. 25, 2019

(87) PCT Pub. No.: WO2018/031811
PCT Pub. Date: Feb. 15, 2018

(65) Prior Publication Data
US 2019/0151359 A1    May 23, 2019

Related U.S. Application Data

(60) Provisional application No. 62/373,243, filed on Aug. 10, 2016.

(51) Int. Cl.
| *A61K 35/17* | (2015.01) |
| *A61P 35/00* | (2006.01) |
| *C12N 5/0784* | (2010.01) |
| *C12N 5/0783* | (2010.01) |
| *A61K 35/15* | (2015.01) |
| *A61K 38/17* | (2006.01) |
| *A61K 31/475* | (2006.01) |
| *A61K 31/675* | (2006.01) |
| *A61K 31/704* | (2006.01) |
| *A61K 31/519* | (2006.01) |
| *A61K 38/50* | (2006.01) |
| *A61K 45/06* | (2006.01) |
| *A61K 31/573* | (2006.01) |
| *A61N 5/10* | (2006.01) |
| *A61K 39/00* | (2006.01) |
| *A61K 35/12* | (2015.01) |

(52) U.S. Cl.
CPC ............ *A61K 35/15* (2013.01); *A61K 31/475* (2013.01); *A61K 31/519* (2013.01); *A61K 31/573* (2013.01); *A61K 31/675* (2013.01); *A61K 31/704* (2013.01); *A61K 35/17* (2013.01); *A61K 38/177* (2013.01); *A61K 38/50* (2013.01); *A61K 45/06* (2013.01); *A61N 5/10* (2013.01); *A61P 35/00* (2018.01); *C12N 5/0636* (2013.01); *C12N 5/0639* (2013.01); *C12Y 305/01001* (2013.01); *A61K 2035/124* (2013.01); *A61K 2039/5154* (2013.01); *C12N 2501/2302* (2013.01); *C12N 2501/2321* (2013.01); *C12N 2510/00* (2013.01)

(58) Field of Classification Search
None
See application file for complete search history.

(56) References Cited

U.S. PATENT DOCUMENTS

| 7,531,628 | B2 * | 5/2009 | Beall ................. G01N 33/5052 435/69.7 |
| 2005/0048071 | A1 | 3/2005 | Bae et al. |
| 2005/0271662 | A1 | 12/2005 | Beall et al. |
| 2006/0269973 | A1 * | 11/2006 | Yee ................... G01N 33/57484 435/7.23 |
| 2010/0136558 | A1 | 6/2010 | Kano et al. |
| 2011/0217298 | A1 | 9/2011 | Hansen et al. |
| 2012/0321666 | A1 | 12/2012 | Cooper et al. |
| 2013/0183343 | A1 | 7/2013 | Czerniecki et al. |
| 2014/0316125 | A1 | 10/2014 | Ferrand et al. |

FOREIGN PATENT DOCUMENTS

| WO | WO-2016201394 A1 | 12/2016 |
| WO | WO-2018031811 A1 | 2/2018 |

OTHER PUBLICATIONS

Schnurr et al. Cancer Res. Sep. 1, 2001; 61(17):6445-6450 (Year: 2001).*
Panjwani et al., Mol Ther. Sep. 2016;24(9):1602-1614 (Year: 2016).*
Wang, X.: The Clinical Research of Anti-CD20 CAR-T Cells in Patients With Refractory or Relapsed B Lymphocyte Lymphoma. NIH U.S. National Library of Medicine, ClinicalTrials.gov. Study Details; Tabular View; Disclaimer: 15 pages. https://clinicaltrials.gov/ct2/show/NCT03576807 (Accessed on Jul. 22, 2020).
Bae et al.: Identification of CD19 and CD20 Peptides for Induction of Antigen-Specific CTLs against B-Cell Malignancies. Clin Cancer Res. 11(4): 1629-1638 (2005).
European Patent Application No. 17840300.2 Supplementary European Search Report dated Mar. 4, 2020.
PCT/US17/46354 International Search Report dated Nov. 21, 2017.
Addissie, et al. Cellular Immunotherapy of Canine Cancer. Veterinary sciences 5.4 (Dec. 6, 2018): 100. 8 pages.
Appelbaum, et al. Cure of malignant lymphoma in dogs with peripheral blood stem cell transplantation. Transplantation 42.1 (Jul. 1986): 19-22.

(Continued)

*Primary Examiner* — Daniel C Gamett
(74) *Attorney, Agent, or Firm* — Wilson Sonsini Goodrich & Rosati

(57) ABSTRACT

The present disclosure provides compositions of immune cells presenting a target molecule or a fragment thereof and provides compositions and methods of producing immune cell therapies with targeted activity against cancer. Methods for conditioning a subject receiving the immune cell therapy of the disclosure are additionally disclosed. The immune cell therapies of the present disclosure can be administered to a subject in need thereof for diseases such as cancer.

25 Claims, 23 Drawing Sheets

Specification includes a Sequence Listing.

(56) References Cited

OTHER PUBLICATIONS

Bujak, et al. Adoptive cell transfer: new perspective treatment in veterinary oncology. Acta veterinaria scandinavica 60.1 (Oct. 18, 2018): 60. 13 pages.
Deeg, et al. Autologous marrow transplantation as consolidation therapy for canine lymphoma: efficacy and toxicity of various regimens of total body irradiation. American journal of veterinary research 46.9 (1985): 2016-2018.
Frimberger, et al. A combination chemotherapy protocol with dose intensification and autologous bone marrow transplant (VELCAP—HDC) for canine lymphoma. Journal of veterinary internal medicine 20.2 (2006): 355-364.
Hudecek, et al. Adoptive T-cell therapy for B-cell malignancies. Expert review of hematology 2.5 (Oct. 2009): 517-532.
Kano, et al. Canine CD20 gene. Veterinary immunology and immunopathology 108.3-4 (2005): 265-268.
Klingenmann, H. Immunotherapy for dogs: running behind humans. Frontiers in Immunology9 (Feb. 5, 2018): 133. 6 Pages.
Lupu, et al. Five decades of progress in haematopoietic cell transplantation based on the preclinical canine model. Veterinary and comparative oncology 5.1 (Mar. 2007): 14-30.
Lupu, et al. Use of multigeneration-family molecular dog leukocyte antigen typing to select a hematopoietic cell transplant donor for a dog with T-cell lymphoma. Journal of the American Veterinary Medical Association 228.5 (2006): 728-732.
Marconato, L. The staging and treatment of multicentric high-grade lymphoma in dogs: a review of recent developments and future prospects. The Veterinary Journal 188.1 (2011): 34-38.
Marconato, L. The staging and treatment of multicentric high-grade lymphoma in dogs: a review of recent developments and future prospects. The Veterinary Journal 188.1 (Apr. 2011): 34-38.
Mata, et al. Towards immunotherapy with redirected T cells in a large animal model: Ex vivo activation, expansion, and genetic modification of canine T cells. Journal of immunotherapy (Hagerstown, Md.: 1997) 37.8 (2014): 407-415.
Mie, et al. Change in peripheral blood lymphocyte count in dogs following adoptive immunotherapy using lymphokine-activated T killer cells combined with palliative tumor resection. Veterinary immunology and immunopathology 177 (2016): 58-63.
Oconnor, et al. Adoptive T-cell therapy improves treatment of canine non-Hodgkin lymphoma post chemotherapy. Scientific reports 2 (Feb. 13, 2012): 249. 12 pages.
O'Connor, et al. Developing T cell cancer immunotherapy in the dog with lymphoma. ILAR journal 55.1 (2014): 169-181.
Richards, et al. Man's best friend: what can pet dogs teach US about non- H odgkin's lymphoma?. Immunological reviews263.1 (2015): 173-191.
Sun, et al. B lymphoblastoid cell lines as efficient APC to elicit CD8+ T cell responses against a cytomegalovirus antigen. The Journal of Immunology 165.7 (2000): 4105-4111.
Suter, et al. Allogeneic hematopoietic cell transplantation in a dog with acute large granular lymphocytic leukemia. Journal of the American Veterinary Medical Association 246.9 (2015): 994-997. Partial retraction in: J Am Vet Med Assoc. Aug. 1, 2015;247(3):299.
Suter, et al. Allogeneic hematopoietic cell transplantation in a dog with acute large granular lymphocytic leukemia. Journal of the American Veterinary Medical Association 246.9 (May 1, 2015): 994-997.
Tagawa, et al. Evaluation of costimulatory molecules in dogs with B cell high grade lymphoma. PloS one 13.7 (Jul. 24, 2018): e0201222. 14 Pages.
Wang, et al. Cellular immunotherapy for follicular lymphoma using genetically modified CD20-specific CD8+ cytotoxic T lymphocytes. Molecular Therapy 9.4 (Apr. 2004): 577-586.
Waugh, et al. Optimisation and validation of a PCR for antigen receptor rearrangement (PARR) assay to detect clonality in canine lymphoid malignancies. Veterinary immunology and immunopathology 182 (2016): 115-124.
EP Application No. 17840300.2 Communication pursuant to Article 94(3) EPC mailed Oct. 14, 2021.
PCT/US2017/046354 International Preliminary Report on Patentability dated Feb. 12, 2019.
Redeker, A. et al., "The Particular Role of T Cell Costimulation, Cytokines, and Post-Transfer Vaccination", Frontiers in Immunology, 2016, vol. 7, Article 345, pp. 1-17.
Redeker et al.: Improving Adoptive T Cell Therapy: The Particular Role of T Cell Costimulation, Cytokines, and Post-Transfer Vaccination. Front Immunol. 7(345): 1-17 (2016).

\* cited by examiner

SEQUENCE LISTING

<160> NUMBER OF SEQ ID NOS: 11

<210> SEQ ID NO 1
<211> LENGTH: 296
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 1

Met Thr Thr Pro Arg Asn Ser Met Ser Gly Thr Leu Pro Val Asp Pro
1               5                   10                  15

Met Lys Ser Pro Thr Ala Met Tyr Pro Val Gln Lys Ile Ile Pro Lys
            20                  25                  30

Arg Met Pro Ser Val Val Gly Pro Thr Gln Asn Phe Phe Met Arg Glu
        35                  40                  45

Ser Lys Thr Leu Gly Ala Val Gln Ile Met Asn Gly Leu Phe His Ile
    50                  55                  60

Ala Leu Gly Ser Leu Leu Met Ile His Thr Asp Val Cys Ala Pro Ile
65                  70                  75                  80

Cys Ile Thr Met Trp Tyr Pro Leu Trp Gly Ile Met Phe Ile Ile
                85                  90                  95

Ser Gly Ser Leu Leu Ala Ala Asp Lys Asn Pro Arg Lys Ser Leu
                100                 105                 110

Val Lys Gly Lys Met Ile Met Asn Ser Leu Ser Leu Phe Ala Ala Ile
            115                 120                 125

Ser Gly Ile Ile Phe Leu Ile Met Asp Ile Phe Asn Ile Thr Ile Ser
    130                 135                 140

His Phe Phe Lys Met Glu Asn Leu Asn Leu Ile Lys Ala Pro Met Pro
145                 150                 155                 160

Tyr Val Asp Ile His Asn Cys Asp Pro Ala Asn Pro Ser Glu Lys Asn
                165                 170                 175

Ser Leu Ser Gln Tyr Cys Gly Ser Ile Arg Ser Val Phe Leu Gly Val
                180                 185                 190

Phe Ala Val Met Leu Ile Phe Ala Phe Phe Gln Lys Leu Val Thr Ala
            195                 200                 205

Gly Ile Val Glu Asn Glu Trp Lys Lys Leu Cys Ser Lys Pro Lys Ser
        210                 215                 220

Asp Val Val Leu Leu Ala Ala Glu Glu Lys Lys Glu Gln Pro Ile
225                 230                 235                 240

Glu Thr Thr Glu Glu Met Val Glu Leu Thr Glu Ile Ala Ser Gln Pro
                245                 250                 255

Lys Lys Glu Glu Asp Ile Glu Ile Pro Val Gln Glu Glu Glu Gly
            260                 265                 270

Glu Leu Glu Ile Asn Phe Ala Glu Pro Pro Gln Glu Gln Glu Ser Ser
        275                 280                 285

Pro Ile Glu Asn Asp Ser Ile Pro
    290                 295

<210> SEQ ID NO 2
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg

-continued

```
                20                  25                  30
Arg Met Ser Ser Leu Val Gly Pro Thr Gln Ser Phe Phe Met Arg Glu
             35                  40                  45
Ser Lys Thr Leu Gly Ala Val Gln Ile Met Asn Gly Leu Phe His Ile
         50                  55                  60
Ala Leu Gly Gly Leu Leu Met Ile Pro Ala Gly Ile Tyr Ala Pro Ile
 65                  70                  75                  80
Cys Val Thr Val Trp Tyr Pro Leu Trp Gly Gly Ile Met Tyr Ile Ile
                 85                  90                  95
Ser Gly Ser Leu Leu Ala Ala Thr Glu Lys Asn Ser Arg Lys Cys Leu
             100                 105                 110
Val Lys Gly Lys Met Ile Met Asn Ser Leu Ser Leu Phe Ala Ala Ile
         115                 120                 125
Ser Gly Met Ile Leu Ser Ile Met Asp Ile Leu Asn Ile Lys Ile Ser
     130                 135                 140
His Phe Leu Lys Met Glu Ser Leu Asn Phe Ile Arg Ala His Thr Pro
145                 150                 155                 160
Tyr Ile Asn Ile Tyr Asn Cys Glu Pro Ala Asn Pro Ser Glu Lys Asn
                 165                 170                 175
Ser Pro Ser Thr Gln Tyr Cys Tyr Ser Ile Gln Ser Leu Phe Leu Gly
             180                 185                 190
Ile Leu Ser Val Met Leu Ile Phe Ala Phe Phe Gln Glu Leu Val Ile
         195                 200                 205
Ala Gly Ile Val Glu Asn Glu Trp Lys Arg Thr Cys Ser Arg Pro Lys
     210                 215                 220
Ser Asn Ile Val Leu Leu Ser Ala Glu Glu Lys Lys Glu Gln Thr Ile
225                 230                 235                 240
Glu Ile Lys Glu Glu Val Val Gly Leu Thr Glu Thr Ser Ser Gln Pro
                 245                 250                 255
Lys Asn Glu Glu Asp Ile Glu Ile Ile Pro Ile Gln Glu Glu Glu Glu
             260                 265                 270
Glu Glu Thr Glu Thr Asn Phe Pro Glu Pro Pro Gln Asp Gln Glu Ser
         275                 280                 285
Ser Pro Ile Glu Asn Asp Ser Ser Pro
     290                 295
```

<210> SEQ ID NO 3
<211> LENGTH: 298
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Thr Thr Pro Arg Asn Ser Met Ser Gly Thr Leu Pro Ala Asp Ala
 1               5                  10                  15
Met Lys Ser Pro Thr Ala Met Asn Pro Val Gln Lys Ile Ile Pro Lys
             20                  25                  30
Lys Met Pro Ser Val Val Gly Pro Thr Gln Asn Phe Phe Met Lys Glu
         35                  40                  45
Ser Lys Pro Leu Gly Ala Val Gln Ile Met Asn Gly Leu Phe His Met
     50                  55                  60
Ala Leu Gly Gly Leu Leu Met Ile His Met Glu Val Tyr Ala Pro Ile
 65                  70                  75                  80
```

```
Cys Met Thr Val Trp Tyr Pro Leu Trp Gly Ile Met Tyr Ile Ile
                85                  90                  95
Ser Gly Ser Leu Leu Val Ala Ala Glu Lys Asn Pro Arg Lys Ser Leu
            100                 105                 110
Val Lys Gly Lys Met Ile Met Asn Ser Leu Ser Leu Phe Ala Ala Ile
        115                 120                 125
Ser Gly Met Ile Leu Leu Ile Met Asp Ile Phe Asn Ile Ala Ile Ser
    130                 135                 140
His Phe Phe Lys Met Glu Asn Leu Asn Leu Leu Lys Ser Pro Lys Pro
145                 150                 155                 160
Tyr Ile Asp Ile His Thr Cys Gln Pro Glu Ser Lys Pro Ser Glu Lys
                165                 170                 175
Asn Ser Leu Ser Ile Lys Tyr Cys Asp Ser Ile Arg Ser Val Phe Leu
            180                 185                 190
Ser Ile Phe Ala Val Met Val Val Phe Thr Leu Phe Gln Lys Leu Val
        195                 200                 205
Thr Ala Gly Ile Val Glu Asn Glu Trp Lys Lys Leu Cys Ser Lys Pro
    210                 215                 220
Lys Ala Asp Val Val Val Leu Leu Ala Ala Glu Glu Lys Lys Glu Gln
225                 230                 235                 240
Leu Val Glu Ile Thr Glu Glu Ala Val Glu Leu Thr Glu Val Ser Ser
                245                 250                 255
Gln Pro Lys Asn Glu Glu Asp Ile Glu Ile Ile Pro Val Gln Glu Glu
            260                 265                 270
Glu Glu Glu Thr Glu Met Asn Phe Pro Glu Pro Pro Gln Asp Gln Glu
        275                 280                 285
Pro Ser Leu Ile Glu Asn Asp Ser Ile Pro
    290                 295

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgcagactct tggaattggg t                                             21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcagaggta agcgatcgtg                                               20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
```

```
gtggggagca aayaggatta ga                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcatgatga tttgacgtcr t                                               21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcctgagag ccgaggac                                                   18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgaggagacg gtgaccagg                                                  19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagcctgaga gccgaggaca c                                               21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaggagacg gtgaccaggg t                                               21
```

CELL THERAPY COMPOSITIONS AND METHODS OF USE THEREOF

CROSS REFERENCE

This application is a U.S. National Phase Application under 35 U.S.C. § 371 of International Application No. PCT/US2017/046354, filed Aug. 10, 2017, which claims the benefit of U.S. Provisional Patent Application No. 62/373,243, filed Aug. 10, 2016, which are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Aug. 4, 2017, is named 48434-701_601_SL.txt and is 10,106 bytes in size.

BACKGROUND

Cancers such as B cell lymphoma, including Hodgkin's and non-Hodgkin's lymphoma, continue to be a significant burden on health and healthcare. Lymphomas are generally referred to as "blood cancers" and are difficult to treat due to the non-targeted and non-specific nature of conventional chemotherapy treatment or radiation treatment.

SUMMARY

The present disclosure relates to compositions and methods of cell therapy. Described herein are cells presenting antigen, methods of making cells presenting antigen, methods of stimulating antigen-specific cells, methods of conditioning a subject prior to treatment with the cell therapy of the present disclosure, and methods of administering to a subject in need thereof the cell therapy of the present disclosure.

In various aspects, the present disclosure provides a cell presenting a recombinant CD20 or fragment thereof. In some aspects, the recombinant CD20 or the fragment thereof is a canine CD20 or a fragment thereof. In certain aspects, the recombinant CD20 or the fragment thereof comprises at least 80% sequence identity to SEQ ID NO: 1 (MTTPRNSMSGTLPVDPMKSPTAMYPVQKIIPKRMPSVVGPTQNFFMRESKTLGAVQIM NGLFHIALGSLLMIHTDVCAPICITMWYPLWGGIMFIISGSLLAAADKNPRKSLVKGKMI MNSLSLFAAISGIIFLIMDIFNITISHFFKMENLNLIKAPMPYVDIHNCDPANPSEKNSLSQY CGSIRSVFLGVFAVMLIFAFFQKLVTAGIVENEWKKLCSKPKSDVVVLLAAEEKKEQPIE TTEEMVELTEIASQPKKEEDIEIIPVQEEEGELEINFAEPPQEQESSPIENDSIP) or a fragment thereof.

In other aspects, the recombinant CD20 or the fragment thereof is a human CD20 or a fragment thereof. In certain aspects, the recombinant CD20 or the fragment thereof comprises at least 80% sequence identity to SEQ ID NO: 2 (MTTPRNSVNGTFPAEPMKGPIAMQSGPKPLFRRMSSLVGPTQSFFMRESKTLGAVQIMN GLFHIALGGLLMIPAGIYAPICVTVWYPLWGGIMYIISGSLLAATEKNSRKCLVKGKMIM NSLSLFAAIS GMILSIMDILNIKISHFLKMESLNFIRAHTPYINIYNCEPANPSEKNSPSTQY CYSIQSLFLGILSVMLIFAFFQELVIAGIVENEWKRTCSRPKSNIVLLS AEEKKEQTIEIKEE VVGLTETSSQPKNEEDIEIIPIQEEEEEETETNFPEPPQDQESSPIENDSSP) or a fragment thereof.

In still other aspects, the recombinant CD20 or the fragment thereof is a feline CD20 or a fragment thereof. In certain aspects, the recombinant CD20 comprises at least 80% sequence identity to SEQ ID NO: 3 (MTTPRNSMSGTLPADAMKSPTAMNPVQKIIPKKMPSVVGPTQNFFMKESKPLGAVQIM NGLFHMALGGLLMIHMEVYAPICMTVWYPLWGGIMYIISGSLLVAAEKNPRKSLVKGK MIMNSLSLFAAISGMILLIMDIFNIAISHFFKMENLNLLKSPKPYIDIHTCQPESKPSEKNSL SIKYCDSIRSVFLSIFAVMVVFTLFQKLVTAGIVENEWKKLCSKPKADVVVLLAAEEKKE QLVEITEEAVELTEVSSQPKNEEDIEIIPVQEEEEETEMNF PEPPQDQEPSLIENDSIP) or a fragment thereof.

In some aspects, the cell is an antigen presenting cell. In certain aspects, the antigen presenting cell is a dendritic cell, a macrophage, or a B cell. In some aspects, the antigen presenting cell is derived from a chronic lymphocytic leukemia cell line.

In some aspects, the cell further expresses at least one human cell surface molecule. In further aspects, the cell further expresses CD19, CD64, CD86, CD137L, or membrane bound IL-15, or any combination thereof. In other aspects, the cell further presents autologous or allogeneic tumor cell membrane extracts.

In certain aspects, the cell is heat killed. In some aspects, the cell is exposed to 57° C. for 25 minutes. In other aspects, the cell is irradiated. In certain aspects, the cell is exposed to a direct dose of gamma radiation. In some aspects, the direct dose of gamma radiation is 120 Gy. In certain aspects, the cell line is at least 99%, at least 99.5%, or at least 99.9% inactivated.

In various aspects, the present disclosure provides methods of producing a feeder cell of a feeder cell line, the method comprising transfecting a cell with a nucleotide sequence encoding a recombinant CD20 or a fragment thereof, thereby producing the feeder cell of the feeder cell line. In some aspects, the recombinant CD20 or the fragment thereof is a canine CD20 or a fragment thereof. In certain aspects, the nucleotide sequence encodes an amino acid sequence with at least 80% sequence identity to SEQ ID NO: 1 (MTTPRNSMSGTLPVDPMKSPTAMYPVQKIIPKRMPSVVGPTQNFFMRESKTLGAVQIM NGLFHIALGSLLMIHTDVCAPICITMWYPLWGGIMFIISGSLLAAADKNPRKSLVKGKMI MNSLSLFAAISGIIFLIMDIFNITISHFFKMENLNLIKAPMPYVDIHNCDPANPSEKNSLSQY CGSIRSVFLGVFAVMLIFAFFQKLVTAGIVENEWKKLCSKPKSDVVVLLAAEEKKEQPIE TTEEMVELTEIASQPKKEEDIEIIPVQEEEGELEINFAEPPQEQESSPIENDSIP) or a fragment thereof.

In other aspects, the recombinant CD20 or the fragment thereof of the method is a human CD20 or a fragment thereof. In certain aspects, the nucleotide sequence encodes an amino acid sequence with at least 80% sequence identity to SEQ ID NO: 2 (MTTPRNSVNGTFPAEPMKGPIAMQSGPKPLFRRMSSLVGPTQSFFMRESKTLGAVQIMN GLFHIALGGLLMIPAGIYAPICVTVWYPLWGGIMYIISGSLLAATEKNSRKCLVKGKMIM NSLSLFAAISGMILSIMDILNIKISHFLKMESLNFIRAHTPYINIYNCEPANPSEKNSPSTQY CYSIQSLFLGILSVMLIFAFFQELVIAGIVENEWKRT- CSRPKSNIVLLSAEEKKEQTIEIKEE VVGLTETSSQPK-NEEDIEIIPIQEEEEEETETNFPEPPQDQESSPIENDSSP) or a fragment thereof.

In other aspects, the recombinant CD20 or the fragment thereof of the method is a feline CD20 or a fragment thereof. In certain aspects, the nucleotide sequence encodes an amino acid sequence with at least 80% sequence identity to SEQ ID NO: 3 (MTTPRNSMSGTLPADAMKSPTAM-NPVQKIIPKKMPSVVGPTQNFFMKESKPLGAVQIM NGLFHMALGGLLMIHMEVYAPICMTVWYPLWG-GIMYIISGSLLVAAEKNPRKSLVKGK MIMNSLSL-FAAISGMILLIMDIFNIAISHFFKMENLNLLKSPKPYI-DIHTCQPESKPSEKNSL SIKYCDSIRSVFLSIFAVMVVFTLFQKLVTAGIVE-NEWKKLCSKPKADVVVLLAAEEKKE QLVEITEE-AVELTEVSSQPKNEEDIEIIPVQEEEEETEMNF-PEPPQDQEPSLIENDSIP) or a fragment thereof.

In some aspects, the cell of the method is an antigen presenting cell. In certain aspects, the antigen presenting cell is a dendritic cell, a macrophage, or a B cell. In some aspects, the antigen presenting cell is derived from a chronic lymphocytic leukemia cell line.

In some aspects, the present disclosure provides methods further comprising transducing the cell to express a human cell surface molecule. In certain aspects, the method further comprises transducing the cell to express CD19, CD64, CD86, CD137L, or membrane bound IL-15, or a combination thereof. In other aspects, the method further comprises pulsing the cell with autologous or allogeneic tumor cell membrane extracts. In certain aspects, the transducing the cell is with a lentivirus. In still other aspects, the method the transfecting is via electroporation with the nucleotide sequence encoding the recombinant CD20 or the fragment thereof.

In certain aspects, the present disclosure provides methods further comprising heat killing the cell after transfecting. In some aspects, the heat killing is exposing the cell to 57° C. for 25 minutes. In other aspects, the method further comprises irradiating the cell after transfecting. In some aspects, the irradiating is exposing the cell to a direct dose of gamma radiation. In certain aspects, the direct dose of gamma radiation is 120 Gy. In some aspects, the feeder cell line is at least 99%, at least 99.5%, or at least 99.9% inactivated. In further aspects, the method further comprises mixing the feeder cell line with human anti-CD3 antibody.

In various aspects, the present disclosure provides a composition comprising a first cell with antigen-specificity for CD20 or a fragment thereof imparted by a second cell, wherein the second cell is the composition or feeder cell of the feeder cell line as described above.

In some aspects, the first cell is in a plurality of cells. In certain aspects, the plurality of cells comprises a polyclonal population of cells. In some aspects, the first cell is a T cell. In certain aspects, the first cell is a CD8+ T cell. In other aspects, the first cell is a CD4+ T cell. In further aspects, the plurality of cells further comprises an NK cell. In certain aspects, the first cell kills cancer cells. In some aspects, the first cell kills B cell lymphoma cells. In still certain aspects, the cancer cells are from B cell lymphoma, T cell lymphoma, osteosarcoma, hemangiosarcoma, multiple myeloma, or plasma cell tumors.

In some aspects, the CD20 or the fragment thereof is a canine CD20 or a fragment thereof. In certain aspects, the CD20 or the fragment thereof comprises at least 80% sequence identity to SEQ ID NO: 1 (MTTPRN-SMSGTLPVDPMKSPTAMYPVQKIIPKRM-PSVVGPTQNFFMRESKTLGAVQIM NGLFHIALGSLL-MIHTDVCAPICITMWYPLWGGIMFIISGSLLAAADKN-PRKSLVKGKMI MNSLSLFAAISGIIFLIMDIFNITISHFFKMENLN-LIKAPMPYVDIHNCDPANPSEKNSLSQY CGSIRSVFLGVFAVMLIFAFFQKLVTAGIVE-NEWKKLCSKPKSDVVVLLAAEEKKEQPIE TTEEMVELTEIASQPKKEEDIEIIPVQEEEGELEINFAE-PPQEQESSPIENDSIP) or a fragment thereof.

In other aspects, the CD20 or a fragment thereof is a human CD20 or a fragment thereof. In certain aspects, the CD20 or the fragment thereof comprises at least 80% sequence identity to SEQ ID NO: 2 (MTTPRNSVNGTF-PAEPMKGPIAMQSGPKPLFRRMSSLVGPTQSFFM-RESKTLGAVQIMN GLFHIALGGLLMIPAGIYAPI-CVTVWYPLWGGIMYIISGSLLAATEKNSRKCLVKG-KMIM NSLSLFAAISGMILSIMDILNIKISHFLKMESLN-FIRAHTPYINIYNCEPANPSEKNSPSTQY CYSIQSLFLGILSVMLIFAFFQELVIAGIVENEWKRT-CSRPKSNIVLLSAEEKKEQTIEIKEE VVGLTETSSQPK-NEEDIEIIPIQEEEEEETETNFPEPPQDQESSPIENDSSP) or a fragment thereof.

In still other aspects, the CD20 or the fragment thereof is a feline CD20 or a fragment thereof. In certain aspects, the CD20 or the fragment thereof comprises at least 80% sequence identity to SEQ ID NO: 3 (MTTPRNSMSGTLP-ADAMKSPTAM-NPVQKIIPKKMPSVVGPTQNFFMKESKPLGAVQIM NGLFHMALGGLLMIHMEVYAPICMTVWYPLWG-GIMYIISGSLLVAAEKNPRKSLVKGK MIMNSLSL-FAAISGMILLIMDIFNIAISHFFKMENLNLLKSPKPYI-DIHTCQPESKPSEKNSL SIKYCDSIRSVFLSIFAVMVVFTLFQKLVTAGIVE-NEWKKLCSKPKADVVVLLAAEEKKE QLVEITEE-AVELTEVSSQPKNEEDIEIIPVQEEEEETEMNF-PEPPQDQEPSLIENDSIP) or a fragment thereof.

In various aspects, the present disclosure provides a method of producing an antigen specific cell, the method comprising contacting a first cell with a second cell, wherein the first cell is the composition or feeder cell of the feeder cell line as described above, thereby producing the antigen specific cell. In some aspects, the method further comprises collecting the second cell from a subject. In certain aspects, the second cell is a mononuclear white blood cell.

In some aspects, the method further comprises isolating the second cell from whole peripheral blood. In certain aspects, the isolating is by density centrifugation. In some aspects, the second cell is cryopreserved.

In certain aspects, the contacting occurs in a co-culture. In some aspects, co-culture comprises a 1:2 ratio of the first cell and the second cell.

In some aspects, the co-culture further comprises an interleukin mixture. In certain aspects, the interleukin mixture comprises interleukin 21 or interleukin 2, or a combination thereof. In further aspects, the interleukin 21 is a recombinant human interleukin 21. In still further aspects, the interleukin 2 is a recombinant human interleukin 2. In some aspects, the method further comprises adding phytohemaglutinin or anti-CD3 antibody, or a combination thereof, to the co-culture.

In some aspects, the method further comprises propagating the co-culture for 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, or 42 days.

In some aspects, the method further comprises adding interleukin 21 at least three times in the first week of the co-culture. In certain aspects, the interleukin 21 is added at a dose of 100 U/ml. In other aspects, the interleukin 21 is added at a dose of 30 U/ml, 40 U/ml, 50 U/ml, 60 U/ml, 70 U/ml, 80 U/ml, 90 U/ml, 100 U/ml, 110 U/ml, 120 U/ml, 130 U/ml, 140 U/ml, 150 U/ml, 160 U/ml, 170 U/ml, 180 U/ml, 190 U/ml, 200 U/ml, 210 U/ml, 220 U/ml, 230 U/ml, 240 U/ml, 250 U/ml, 260 U/ml, 270 U/ml, 280 U/ml, 290 U/ml, or 300 U/ml.

In some aspects, the method further comprises co-administering interleukin 21 and interleukin 2 three times a week starting in the second week of the co-culture. In certain aspects, interleukin 21 and interleukin 2 are each added at a dose of 100 U/ml. In other aspects, interleukin 21 and interleukin 2 are each added at a dose of 30 U/ml, 40 U/ml, 50 U/ml, 60 U/ml, 70 U/ml, 80 U/ml, 90U/ml, 100 U/ml, 110 U/ml, 120 U/ml, 130 U/ml, 140 U/ml, 150 U/ml, 160 U/ml, 170 U/ml, 180 U/ml, 190 U/ml, 200 U/ml, 210 U/ml, 220 U/ml, 230 U/ml, 240 U/ml, 250 U/ml, 260 U/ml, 270 U/ml, 280 U/ml, 290 U/ml, or 300 U/ml.

In some aspects, the method further comprises adding interleukin 2 to the co-culture at least three times a week in a second week of the co-culture, a third week of co-culture, a fourth week of the co-culture, a fifth week of the co-culture, a sixth week of the co-culture, or any combination thereof. In certain aspects, interleukin 2 is added at a dose of 100 U/ml. In other aspects, interleukin 2 is added at a dose of 30 U/ml, 40 U/ml, 50 U/ml, 60 U/ml, 70 U/ml, 80 U/ml, 90U/ml, 100 U/ml, 110 U/ml, 120 U/ml, 130 U/ml, 140 U/ml, 150 U/ml, 160 U/ml, 170 U/ml, 180 U/ml, 190 U/ml, 200 U/ml, 210 U/ml, 220 U/ml, 230 U/ml, 240 U/ml, 250 U/ml, 260 U/ml, 270 U/ml, 280 U/ml, 290 U/ml, or 300 U/ml.

In certain aspects, the method further comprises adding an additional first cell every 7 days, every 8 days, every 9 days, or every 10 days of the co-culture. In some aspects, the second cell is the antigen specific cell after at least 10 days in the co-culture. In certain aspects, an antigen of the antigen specific cell is CD20 or a fragment thereof.

In some aspects, the antigen specific cell is in a plurality of cells. In certain aspects, the plurality of cell comprises a polyclonal population of cells. In certain aspects, the antigen specific cell is a T cell. In some aspects, the antigen specific cell is a CD8+ T cell. In other aspects, the antigen specific cell is a CD4+ T cell. In further aspects, the plurality of cells further comprise an NK cell.

In some aspects, the antigen specific cell kills cancer cells. In certain aspects, the antigen specific cell kills a B cell lymphoma cell. In further aspects, the cancer cell is from a B cell lymphoma, a T cell lymphoma, an osteosarcoma, a hemangiosarcoma, a multiple myeloma, or a plasma cell tumor.

In various aspects, the present disclosure provides a method of conditioning a subject in need thereof before administering the antigen specific cell as described above, the method comprising treating a subject with a chemotherapy; and consolidating the chemotherapy with high dose chemotherapy or total body irradiation. In some aspects, the chemotherapy is an induction chemotherapy or a maintenance chemotherapy. In certain aspects, the chemotherapy is a multi-agent chemotherapy comprising one or more of cyclophosphamide, doxorubicin, adriamycin, or vincristine.

In further aspects, the high dose chemotherapy comprises cyclophosphamide. In some aspects, the high dose chemotherapy is given at a dose of from 250 mg/m$^2$-650 mg/m$^2$. In other aspects, the high dose chemotherapy is given at a dose of from 250 mg/m$^2$-300 mg/m$^2$, 300 mg/m$^2$-350 mg/m$^2$, 350 mg/m$^2$-400 mg/m$^2$, 400 mg/m$^2$-450 mg/m$^2$, 450 mg/m$^2$-500 mg/m$^2$, 500 mg/m$^2$-550 mg/m$^2$, 550 mg/m$^2$-600 mg/m$^2$, or 600 mg/m$^2$-650 mg/m$^2$.

In some aspects, the total body irradiation is achieved by exposing a subject to a dose of gamma irradiation. In certain aspects, the dose of gamma irradiation is from 2-12 Gy. In other aspects, the dose of gamma irradiation is from 2-4 Gy, 4-6 Gy, 6-8 Gy, 8-10 Gy, or 10-12 Gy.

In certain aspects, the method further comprises rescuing the subject with a dose of autologous or allogeneic CD34+ cells from $0.5 \times 10^6$-$10 \times 10^6$ cells/kg. In other aspects, the dose of autologous or allogeneic CD34+ cells is from $0.5 \times 10^6$-$2 \times 10^6$ cells/kg, $2 \times 10^6$-$4 \times 10^6$ cells/kg, $4 \times 10^6$-$6 \times 10^6$ cells/kg, $6 \times 10^6$-$8 \times 10^6$ cells/kg, or $8 \times 10^6$-$10 \times 10^6$ cells/kg.

In various aspects, the present disclosure provides a method of treating a subject in need thereof comprising administering the antigen specific cell as described previously to the subject. In some aspects, the administering is an infusion via a peripheral vein catheter.

In some aspects, the administering comprises at least one dose of the antigen specific cell. In certain aspects, the administering comprises a first dose infused at a rate of $5 \times 10^8$ cells/m$^2$. In further aspects, the method further comprises administering a second dose infused two weeks after the first dose. In still further aspects, the second dose is infused at a rate of $5 \times 10^9$ cells/m$^2$. In some aspects, the method further comprises administering a third dose infused four weeks after the first dose and two weeks after the second dose. In further aspects, the third dose is infused at a rate of $5 \times 10^9$ cells/m$^2$.

In certain aspects, the subject undergoes the conditioning as described above. In some aspects, the subject is a canine. In other aspects, the subject is a human. In still other aspects, the subject is a feline.

In some aspects, the subject has a disease. In certain aspects, the disease is cancer. In further aspects, the cancer is B cell lymphoma. In still further aspects, the cancer is B cell lymphoma, T cell lymphoma, osteosarcoma, hemangiosarcoma, multiple myeloma, or plasma cell tumors.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
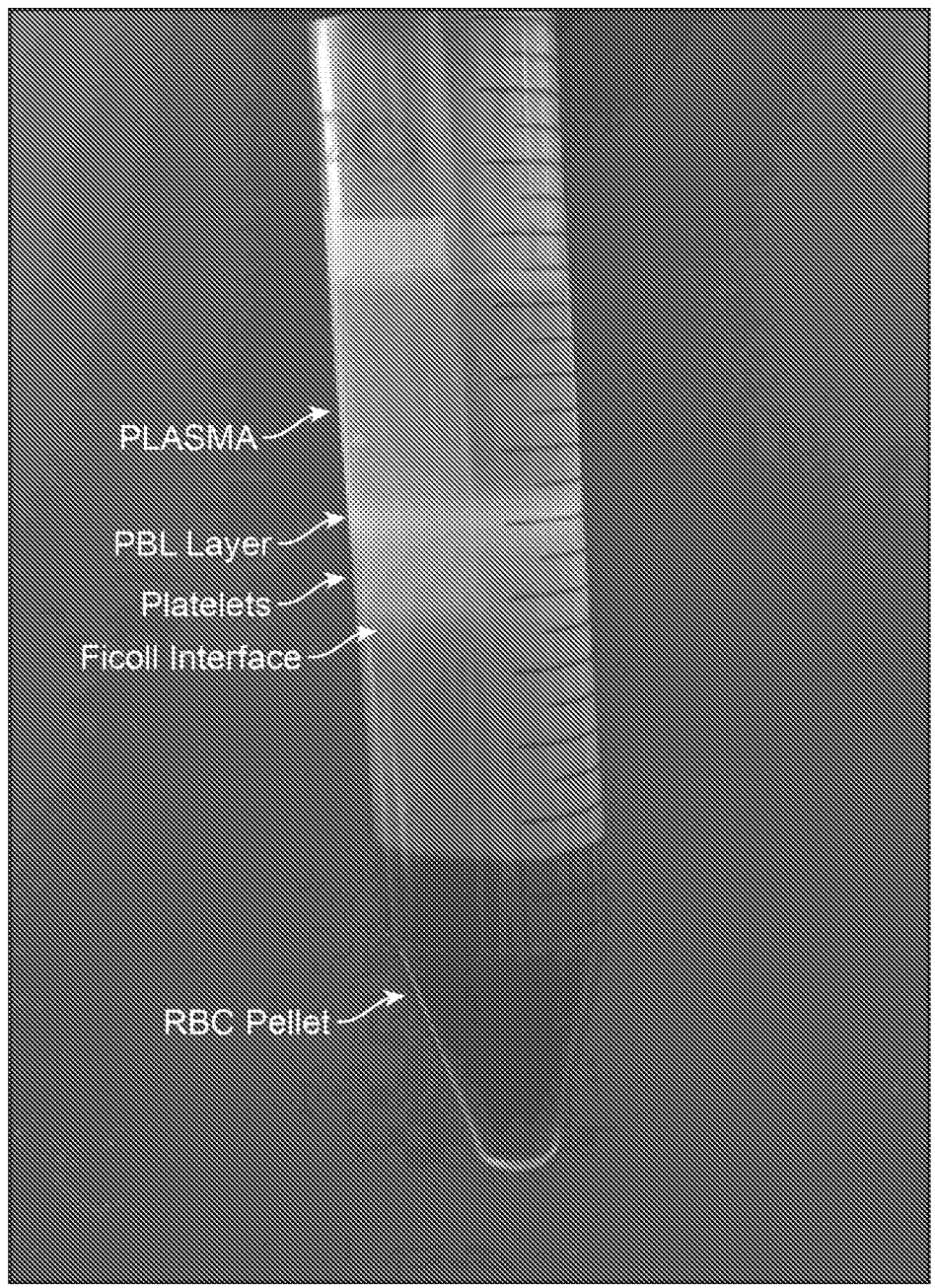
FIG. 1 shows density centrifugation of whole blood over a Ficoll layer. From top to bottom, the layers are: plasma, peripheral blood lymphocyte (PBL) layer, platelets, Ficoll interface, and red blood cell (RBC) pellet.

Immunotherapies for B cell lymphoma have been primarily focused on monoclonal antibody therapy. Cell-based immunotherapies targeted towards cancer cells overexpressing specific antigens are only recently emerging. The present disclosure provides compositions of a cell presenting a target antigen, such as a recombinant CD20 antigen. Furthermore, the present disclosure provides methods of producing the cell presenting CD20 antigen. The present disclosure also provides methods of producing CD20 antigen specific cells that comprise an adoptive T cell therapy (ACT). Methods for administering the adoptive T cell therapy to a subject in need thereof are provided as well as methods for conditioning the subject prior to administration of the ACT.

As used herein, the term "feeder cells" may refer to an antigen presenting cell that may be used to present a target antigen and activate T lymphocytes with effector functions directed towards cells expressing the target antigen. Feeder cells may be any antigen presenting cells including dendritic cells, monocytes, macrophages, or any combination thereof.

As used herein, the term "priming" may refer to the process by which a feeder cell activates a T cell. This process may include contacting of the T cell's T cell receptor (TCR) with its cognate antigen presented in the context of a surface major histocompatibility complex molecule, release of cytokines by the antigen presenting cell, and stimulation of co-stimulatory molecules of the T cell via engagement by other surface receptors.

As used herein, the term "antigen specific T cell" may refer to a T lymphocyte primed by a feeder cell presenting a target antigen. Antigen specific T cells may be CD4+ T cells or CD8+ T cells. Antigen specific CD4+ T cells may help enhance effector functions of other cell types, and antigen specific CD8+ T cells may act directly on cells expressing the target antigen.

As used herein, the term "polyclonal population of effector cells" may refer to a population of T cells with diverse TCRs that may be specific for a single antigen, wherein these diverse TCRs may recognize different epitopes of an antigen. The T cells may be CD4+ T cells, CD8+ T cells, or a combination thereof.

As used herein, the term "ACT" may refer to adoptive T cell therapy. In this therapy, immune cells isolated from a subject may be primed ex vivo to selectively recognize a target antigen and carry out an effector function such as target cell destruction. ACT may be used in the treatment of cancer, where immune cells may be isolated from a patient, T cells may be primed and expanded ex vivo by feeder cells, and T cells may be administered back into a patient. The T cell population administered back into the patient may be a clonal T cell population or a polyclonal T cell population.

As used herein, the term "CHOP" may refer to a standard multi-agent chemotherapy protocol and may be administered to subjects in need thereof. CHOP therapy may include a combination of three chemotherapeutic agents including cyclophosphamide, doxorubicin, and vincristine and a steroid including prednisone. CHOP may be used in treatment of subjects in need thereof, or as a pre-conditioning step prior to ACT. Dosing of CHOP therapy may be administered as shown in Table 1.

TABLE 1

CHOP Therapy Dosing Regimen

| Week | Cyclophosphamide | Doxorubicin | Vincristine | Prednisone |
|---|---|---|---|---|
| 1 | | | 0.7 mg/m² IV | 2 mg/kg PO SID |
| 2 | 250 mg/m² IV or PO | | | 1.5 mg/kg PO SID |
| 3 | | | 0.7 mg/m² IV | 1 mg/kg PO SID |
| 4 | | 30 mg/m² IV | | 0.5 mg/kg PO SID |
| 5 | | | | |
| 6 | | | 0.7 mg/m² IV | |
| 7 | 250 mg/m² IV or PO | | | |
| 8 | | | 0.7 mg/m² IV | |
| 9 | | 30 mg/m² IV | | |

IV: intravenous
PO: orally
SID: once a day

As used herein, the term "conditioning" may refer to a chemotherapy treatment regimen administered to a subject prior to infusion of the ACT. In some aspects, a subject may be preconditioned with standard CHOP therapy. In other aspects, CHOP therapy conditioning may be consolidated with high dose cyclophosphamide chemotherapy (500 mg/m² IV or PO) or total body irradiation and may be rescued with autologous or allogeneic CD34+ cells.

As used herein, the term "infusion" may refer to administration of a therapy to a subject in need thereof. Infusion may be carried out by administering the therapy to a subject in need thereof via a peripheral vein catheter.

CD20 Antigen

CD20 is also known as the B-lymphocyte antigen CD20 and may be a glycosylated phosphoprotein expressed by B cells. CD20 may be expressed on the surface of all B cells except early pro-B cells and plasma cells. As B cells mature, the expression of CD20 may increase. However, CD20 may also be expressed by cancer cells, in particular B lymphoma cells, T lymphoma cells, and leukemia.

The present disclosure provides an antigen presenting feeder cell presenting CD20 or a fragment thereof. In some embodiments, the feeder cell may be transfected with a nucleotide sequence encoding CD20 or a fragment thereof. The CD20 or the fragment thereof may be a recombinant canine CD20 or a fragment thereof, or a recombinant human CD20 or a fragment thereof. In some embodiments, the recombinant CD20 or the fragment thereof may comprise a nucleotide sequence encoding the amino acid sequence of SEQ ID NO: 1 (MTTPRNSMSGTLPVDPMKSPTAM-YPVQKIIPKRMPSVVGPTQNFFMRESKTLGAVQIM NGLFHIALGSLLMIHTDVCAPICITMWYPLWGGIMFI-ISGSLLAAADKNPRKSLVKGKMI MNSLSLFAAISGII-FLIMDIFNITISHFFKMENLNLIKAPMPYVDIHNCD-PANPSEKNSLSQY CGSIRSVFLGVFAVMLIFAFFQKLVTAGIVE-NEWKKLCSKPKSDVVVLLAAEEKKEQPIE TTEEMVELTEIASQPKKEEDIEIIPVQEEEGELEINFAE-PPQEQESSPIENDSIP) or a fragment thereof. In certain embodiments, the recombinant CD20 or a fragment thereof may comprise at least 70%, 75%, 80%, 85%, 90%, 95%, or 99% sequence identity to a nucleotide sequence encoding the amino acid sequence of SEQ ID NO: 1 or a fragment thereof. In other embodiments, the recombinant CD20 or the fragment thereof may comprise a nucleotide sequence encoding the amino acid sequence of SEQ ID NO: 2 (MTTPRNSVNGTFPAEPMKGPIAMQSGPKPL-FRRMSSLVGPTQSFFMRESKTLGAVQIMN GLFHIAL-GGLLMIPAGIYAPICVTVWYPLWGGIMYIISGSL-LAATEKNSRKCLVKGKMIM NSLSLFAAISGMILSIMDILNIKISHFLKMESLN-FIRAHTPYINIYNCEPANPSEKNSPSTQY CYSIQSLFLGILSVMLIFAFFQELVIAGIVENEWKRT-CSRPKSNIVLLSAEEKKEQTIEIKEE VVGLTETSSQPK-NEEDIEIIPIQEEEEEETETNFPEPPQDQESSPIENDSSP) or a fragment thereof. In certain embodiments, the recombinant CD20 or a fragment thereof may comprise at least 70%, 75%, 80%, 85%, 90%, 95%, or 99% sequence identity to a nucleotide sequence encoding the amino acid sequence of SEQ ID NO: 2 or a fragment thereof. In other embodiments, the CD20 or the fragment thereof may be a recombinant feline CD20 or a fragment thereof. In some embodiments, the recombinant CD20 or the fragment thereof may comprise a nucleotide sequence encoding the amino acid sequence of SEQ ID NO: 3 (MTTPRNSMSGTLPADAMK-SPTAMNPVQKIIPKKMPSVVGPTQNFFMKESKPL-GAVQIM NGLFHMALGGLLMIHMEVYAPICMTVWY-PLWGGIMYIISGSLLVAAEKNPRKSLVKGK MIMNSLSLFAAISGMILLIMDIFNIAISHFFK-MENLNLLKSPKPYIDIHTCQPESKPSEKNSL SIKYCD-SIRSVFLSIFAVMVVFTLFQKLVTAGIVE-NEWKKLCSKPKADVVVLLAAEEKKE QLVEITEEAVELTEVSSQPKNEEDIEIIPVQEEEEE-TEMNFPEPPQDQEPSLIENDSIP) or a fragment thereof. In certain embodiments, the recombinant CD20 or the fragment thereof may comprise at least 70%, 75%, 80%, 85%, 90%, 95%, or 99% sequence identity to a nucleotide sequence encoding the amino acid sequence of SEQ ID NO: 3 or a fragment thereof.

In some embodiments, the recombinant CD20 or the fragment thereof may comprise an amino acid sequence of SEQ ID NO: 1 (MTTPRNSMSGTLPVDPMKSPTAM-YPVQKIIPKRMPSVVGPTQNFFMRESKTLGAVQIM NGLFHIALGSLLMIHTDVCAPICITMWYPLWGGIMFI-ISGSLLAAADKNPRKSLVKGKMI MNSLSLFAAISGII-FLIMDIFNITISHFFKMENLNLIKAPMPYVDIHNCD-PANPSEKNSLSQY CGSIRSVFLGVFAVMLIFAFFQKLVTAGIVE-NEWKKLCSKPKSDVVVLLAAEEKKEQPIE TTEEMVELTEIASQPKKEEDIEIIPVQEEEGELEINFAE-PPQEQESSPIENDSIP) or a fragment thereof. In certain embodiments, the recombinant CD20 or the fragment thereof may comprise at least 70%, 75%, 80%, 85%, 90%, 95%, or 99% sequence identity to an amino acid sequence of SEQ ID NO: 1 or a fragment thereof. In other embodiments, the recombinant CD20 or the fragment thereof may comprise an amino acid sequence of SEQ ID NO: 2 (MTT-PRNSVNGTFPAEPMKGPIAMQSGPKPL-FRRMSSLVGPTQSFFMRESKTLGAVQIMN GLFHIAL-GGLLMIPAGIYAPICVTVWYPLWGGIMYIISGSL- LAATEKNSRKCLVKGKMIM NSLSLFAAISGMILSIMDILNIKISHFLKMESLNFIRAHTPYINIYNCEPANPSEKNSPSTQY CYSIQSLFLGILSVMLIFAFFQELVIAGIVENEWKRTCSRPKSNIVLLSAEEKKEQTIEIKEE VVGLTETSSQPKNEEDIEIIPIQEEEEEETETNFPEPPQDQESSPIENDSSP) or a fragment thereof. In certain embodiments, the recombinant CD20 or the fragment thereof may comprise at least 70%, 75%, 80%, 85%, 90%, 95%, or 99% sequence identity to an amino acid sequence of SEQ ID NO: 2 or a fragment thereof. In alternate embodiments, the CD20 or the fragment thereof may be a recombinant feline CD20 or a fragment thereof. In some embodiments, the recombinant CD20 or the fragment thereof may comprise an amino acid sequence of SEQ ID NO: 3 (MTTPRNSMSGTLPADAMKSPTAMNPVQKIIPKKMPSVVGPTQNFFMKESKPLGAVQIM NGLFHMALGGLLMIHMEVYAPICMTVWYPLWGGIMYIISGSLLVAAEKNPRKSLVKGK MIMNSLSLFAAISGMILLIMDIFNIAISHFFKMENLNLLKSPKPYIDIHTCQPESKPSEKNSL SIKYCDSIRSVFLSIFAVMVVFTLFQKLVTAGIVENEWKKLCSKPKADVVVLLAAEEKKE QLVEITEEAVELTEVSSQPKNEEDIEIIPVQEEEEETEMNFPEPPQDQEPSLIENDSIP) or a fragment thereof. In certain embodiments, the recombinant CD20 or the fragment thereof may comprise at least 70%, 75%, 80%, 85%, 90%, 95%, or 99% sequence identity to an amino acid sequence of SEQ ID NO: 3 or a fragment thereof.

Feeder Cells

The present disclosure provides a cell, also referred to herein as a feeder cell or an antigen-presenting feeder cell, presenting CD20 or a fragment thereof. The CD20 or the fragment thereof may be recombinant CD20 or a fragment thereof. Antigen presenting feeder cells may be used to prime antigen specific effector T cells in cell culture. In some embodiments, the feeder cells may be any antigen presenting cell line including dendritic cells, macrophages, or B cells. In some embodiments, the feeder cells may be a gamma irradiated, killed chronic lymphocytic leukemia cell line. In some embodiments, the feeder cells may be a heat killed chronic lymphocytic leukemia cell line. The feeder cells may be a variant of a gamma irradiated, killed chronic lymphocytic leukemia cell line. The feeder cells may be a variant of a heat killed chronic lymphocytic leukemia cell line. The feeder cells may be a gamma irradiated, killed ABT-2 chronic lymphocytic leukemia cell line. The feeder cells may be a heat killed ABT-2 chronic lymphocytic leukemia cell line. The feeder cells may be a variant of ABT-2 chronic lymphocytic leukemia cell line. The feeder cells may be a gamma irradiated, killed variant of ABT-2 chronic lymphocytic leukemia cell line. The feeder cells may be a heat killed variant of ABT-2 chronic lymphocytic leukemia cell line. The chronic lymphocytic leukemia cell line may be comprised of a heterogeneous population of white blood cells. In some embodiments, the chronic lymphocytic leukemia cell line may be a B cell line.

In other embodiments, the feeder cells may be pulsed with tumor cell membrane extracts from autologous tumor cells. For example, the membrane extracts may be derived from autologous tumor cells or allogeneic tumor cells and may be pulsed with ABT-2 cells or ABT-2+ cells to allow for additional presentation of tumor antigens. The membranes may be prepared by exposing tumor cells to three freeze/thaw cycles using liquid nitrogen at −120° C. for five minutes and thawing cells to 37° C. This may result in swelling and ice crystal formation that may disrupt cells and the resulting cells may be centrifuged at 3000 rpm for 10 minutes. The supernatant may be discarded and the tumor cell pellet containing membrane extracts may be added to the co-culture of feeder cells and lymphocytes on Day 1.

The present disclosure provides methods for producing an antigen presenting feeder cell line presenting CD20 or a fragment thereof. In some embodiments, the present disclosure provides methods for transfecting a feeder cell line with a nucleotide sequence encoding CD20 or a fragment thereof. The method may comprise transfecting a feeder cell line with a nucleotide sequence encoding a recombinant CD20 or a fragment thereof. The method may comprise transfecting a feeder cell line with a nucleotide sequence encoding a canine CD20 or a fragment thereof. The method may comprise transfecting a feeder cell line with a nucleotide sequence encoding a recombinant canine CD20 or a fragment thereof. The method may comprise transfecting a feeder cell line with a nucleotide sequence encoding a feline CD20 or a fragment thereof. The method may comprise transfecting a feeder cell line with a nucleotide sequence encoding a feline recombinant CD20 or a fragment thereof. The method may comprise transfecting a feeder cell line with a nucleotide sequence encoding a human CD20 or a fragment thereof. The method may comprise transfecting a feeder cell line with a nucleotide sequence encoding a recombinant human CD20 or a fragment thereof. In some embodiments, the present disclosure provides methods for transfecting a feeder cell line with nucleotide sequence encoded by a CD20 or a fragment thereof of any one of SEQ ID NO: 1-SEQ ID NO: 3 or a fragment thereof. In other embodiments, the present disclosure provides methods for transfecting a feeder cell line with a nucleotide sequence encoded by a CD20 or a fragment thereof that has at least 70%, 75%, 80%, 85%, 90%, 95%, or 99% sequence identity with any one of SEQ ID NO: 1-SEQ ID NO: 3 or a fragment thereof. In certain embodiments, a method of transfecting may comprise transfection of a feeder cell. The transfection may comprise lipofection or electroporation. The transfection may enhance cellular uptake of antigens. The transfection may enhance cellular uptake of a nucleotide sequence encoding CD20 or a fragment thereof. After transfection, the transfected cells of the feeder cell line may express CD20 or a fragment thereof. After transfection, the transfected cells of the feeder cell line may express recombinant CD20 or a fragment thereof. After transfection, the transfected cells of the feeder cell line may express canine CD20 or a fragment thereof. After transfection, the transfected cells of the feeder cell line may express recombinant canine CD20 or a fragment thereof. After transfection, the transfected cells of the feeder cell line may express feline CD20 or a fragment thereof. After transfection, the transfected cells of the feeder cell line may express recombinant feline CD20 or a fragment thereof. After transfection, the transfected cells of the feeder cell line may express human CD20 or a fragment thereof. After transfection, the transfected cells of the feeder cell line may express recombinant human CD20 or a fragment thereof. After transfection, the transfected cells of the feeder cell line may present CD20 or a fragment thereof. After transfection, the transfected cells of the feeder cell line may present recombinant CD20 or a fragment thereof. After transfection, the transfected cells of the feeder cell line may present canine CD20 or a fragment thereof. After transfection, the transfected cells of the feeder cell line may present recombinant canine CD20 or a fragment thereof. After transfection, the transfected cells of the feeder cell line may present feline CD20 or a fragment thereof. After transfection, the transfected cells of the feeder cell line may present recombinant feline CD20 or a fragment thereof. After transfection, the transfected cells of the feeder cell line may present human CD20 or a fragment thereof. After transfection, the transfected cells may present recombinant human CD20 or a fragment thereof.

In some embodiments, the present disclosure provides methods for pulsing of a feeder cell line with CD20 or a fragment thereof. The method may comprise pulsing a feeder cell line with a recombinant CD20 or a fragment thereof. The method may comprise pulsing a feeder cell line with a canine CD20 or a fragment thereof. The method may comprise pulsing a feeder cell line with a recombinant canine CD20 or a fragment thereof. The method may comprise pulsing a feeder cell line with a feline CD20 or a fragment thereof. The method may comprise pulsing a feeder cell line with a feline recombinant CD20 or a fragment thereof. The method may comprise pulsing a feeder cell line with a human CD20 or a fragment thereof. The method may comprise pulsing a feeder cell line with a recombinant human CD20 or a fragment thereof. In some embodiments, the present disclosure provides methods for pulsing a feeder cell line with a CD20 or a fragment thereof of any one of SEQ ID NO: 1-SEQ ID NO: 3, or a fragment thereof. In other embodiments, the present disclosure provides methods for pulsing a feeder cell line with a CD20 or a fragment thereof that has at least 70%, 75%, 80%, 85%, 90%, 95%, or 99% sequence identity with any one of SEQ ID NO: 1-SEQ ID NO: 3 or a fragment thereof. The pulsing may enhance cellular uptake of antigens. The pulsing may enhance cellular uptake of CD20. After pulsing, the pulsed cells may present CD20 or a fragment thereof. After pulsing, the pulsed cells of the feeder cell line may present recombinant CD20 or a fragment thereof. After pulsing, the pulsed cells of the feeder cell line may present canine CD20 or a fragment thereof. After pulsing, the pulsed cells of the feeder cell line may present recombinant canine CD20 or a fragment thereof. After pulsing, the pulsed cells of the feeder cell line may present feline CD20 or a fragment thereof. After pulsing, the pulsed cells of the feeder cell line may present recombinant feline CD20 or a fragment thereof. After pulsing, the pulsed cells of the feeder cell line may present human CD20 or a fragment thereof. After pulsing, the pulsed cells of the feeder cell line may present recombinant human CD20 or a fragment thereof. The method may comprise transfecting a feeder cell line with a nucleic acid sequence encoding a recombinant CD20 or a fragment thereof. The method may comprise transfecting a feeder cell line with a nucleic acid sequence encoding a canine CD20 or a fragment thereof. The method may comprise transfecting a feeder cell line with a nucleic acid sequence encoding a recombinant canine CD20 or a fragment thereof. The method may comprise transfecting a feeder cell line with a nucleic acid sequence encoding a feline CD20 or a fragment thereof. The method may comprise transfecting a feeder cell line with a nucleic acid sequence encoding a feline recombinant CD20 or a fragment thereof. The method may comprise transfecting a feeder cell line with a nucleic acid sequence encoding a human CD20 or a fragment thereof. The method may comprise transfecting a feeder cell line with a nucleic acid sequence encoding a recombinant human CD20 or a fragment thereof. In some embodiments, the present disclosure provides methods for transfecting a feeder cell line with a nucleic acid sequence encoding CD20 or a fragment thereof of any one of SEQ ID NO: 1-SEQ ID NO: 3 or a fragment thereof. In other embodiments, the present disclosure provides methods for transfecting a feeder cell line with a nucleic acid sequence encoding CD20 or a fragment thereof that has at least 70%, 75%, 80%, 85%, 90%, 95%, or 99% sequence identity with any one of SEQ ID NO: 1-SEQ ID NO: 3 or a fragment thereof. The transfection may enhance cellular uptake of nucleic acids encoding antigens. The transfection may enhance cellular uptake of nucleic acids encoding CD20 or a fragment thereof. After transfection, the transfected cells may present CD20 or a fragment thereof. After transfection, the transfected cells of the feeder cell line may present recombinant CD20 or a fragment thereof. After transfecting, the transfected cells of the feeder cell line may present canine CD20 or a fragment thereof. After transfecting, the transfected cells of the feeder cell line may present recombinant canine CD20 or a fragment thereof. After transfecting, the transfected cells of the feeder cell line may present feline CD20 or a fragment thereof. After transfecting, the transfected cells of the feeder cell line may present recombinant feline CD20 or a fragment thereof. After transfecting, the transfected cells of the feeder cell line may present human CD20 or a fragment thereof. After transfecting, the transfected cells of the feeder cell line may present recombinant human CD20 or a fragment thereof.

Feeder cells may be transduced with human cell surface molecules to improve efficiency of activation or proliferation of T cells or other immune cells upon contact. The present disclosure provides methods for transducing feeder cells to express a human cell surface molecule. A lentivirus may be used to transduce feeder cells to express a human cell surface molecule. For example, in some embodiments, the human cell surface molecules may be CD19, CD64, CD86, CD137L, membrane bound IL-15, or any combination thereof. After transduction, the feeder cells may express CD19, CD64, CD86, CD137L, membrane bound IL-15, or any combination thereof. The feeder cells may be transduced after being transfected with CD20. The feeder cells may be transduced before being transfected with CD20. The feeder cells may be transduced after being pulsed with CD20. The feeder cells may be transduced before being pulsed with CD20.

A feeder cell presenting CD20 and transduced to express human cell surface molecules may be heat killed or irradiated. In some embodiments, the present disclosure provides methods for heat killing a feeder cell after transfection as described herein. In some embodiments, the present disclosure provides methods for heat killing a feeder cell after transfection and transduction as described herein. In some embodiments, the present disclosure provides methods for heat killing a feeder cell after pulsing as described herein. In some embodiments, the present disclosure provides methods for heat killing a feeder cell after pulsing and transduction as described herein. For example, a feeder cell may be heat killed by exposing the cell to 57° C. for 25 minutes. A feeder cell may be heat killed by exposing the cell to 57° C. for 15 minutes, 16 minutes, 17 minutes, 18 minutes, 19 minutes, 20 minutes, 21 minutes, 22 minutes, 23 minutes, 24 minutes, 26 minutes, 27 minutes, 28 minutes, 29 minutes, or 30 minutes. In other embodiments, a feeder cell may be heat killed by exposing the cell to 55° C. for 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes. In other embodiments, a feeder cell may be heat killed by exposing the cell to 56° C. for 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes. In other embodiments, a feeder cell may be heat killed by exposing the cell to 58°

C. for 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes. In other embodiments, a feeder cell may be heat killed by exposing the cell to 59° C. for 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes. A feeder cell may be heat killed by exposing the cell to from 56° C. to 58° C. for 15 minutes, 16 minutes, 17 minutes, 18 minutes, 19 minutes, 20 minutes, 21 minutes, 22 minutes, 23 minutes, 24 minutes, 26 minutes, 27 minutes, 28 minutes, 29 minutes, or 30 minutes. A feeder cell may be heat killed by exposing the cell to from 56° C. to 58° C. for from 15 minutes to 30 minutes, 20 minutes to 30 minutes, 25 minutes to 30 minutes, 22 minutes to 28 minutes, or 24 minutes to 26 minutes. A feeder cell may be heat killed by exposing the cell to from 57° C. for from 15 minutes to 30 minutes, 20 minutes to 30 minutes, 25 minutes to 30 minutes, 22 minutes to 28 minutes, or 24 minutes to 26 minutes. In other embodiments, the present disclosure provides methods for irradiating a feeder cell after transfection. In some embodiments, the present disclosure provides methods for irradiating a feeder cell after transfection as described herein. In some embodiments, the present disclosure provides methods for irradiating a feeder cell after transfection and transduction as described herein. In some embodiments, the present disclosure provides methods for irradiating a feeder cell after pulsing as described herein. In some embodiments, the present disclosure provides methods for irradiating a feeder cell after pulsing and transduction as described herein. For example, the feeder cell may be irradiated by exposing the cell to a direct dose of gamma radiation. In some embodiments, the direct dose of gamma radiation may be 100 Gy, 110 Gy, 120 Gy, 130 Gy, 140 Gy, or 150 Gy. In other embodiments, the direct dose of gamma radiation may be from 100 Gy to 150 Gy, 110 Gy to 140 Gy, 110 Gy to 130 Gy, 110 Gy to 120 Gy, 115 Gy to 125 Gy, or 118 Gy to 122 Gy. The present disclosure provides methods of heat killing or irradiating that may result in at least 99%, at least 99.5%, or at least 99.9% inactivation.

Cells

The present disclosure provides a cell or population of cells used in an immunotherapy. A cell may be an antigen specific cell. An antigen specific cell may be an immune cell. An antigen specific cell may be a T cell. In some embodiments an antigen specific cell may be a CD8+ T cell, whose effector function may be to kill cells that express a target antigen. An antigen specific cell may also be a CD4+ T cell, whose effector function may be to aid CD8+ T cells in cytolytic function.

An antigen specific cell may be a T cell which may have been primed by an antigen presenting cell. During priming, an antigen presenting cell may stimulate proliferation of a T cell expressing a TCR specific for the antigen presented by the antigen presenting cell. The antigen may be in the context of a major histocompatibility complex I (MHC I) molecule, major histocompatibility complex II (MHC II) molecule, human leukocyte antigen I (HLA I) molecule, or human leukocyte antigen II (HLA II) molecule on the antigen presenting cell. This proliferation may be a T cell clonal expansion. In some embodiments, T cells with different TCRs may be stimulated by antigen presenting cells presenting the same antigen, which may lead to the clonal expansion of multiple T cells to establish a polyclonal population of T cells.

A population of cells may comprise immune cells. A population of cells may comprise antigen specific cells. A population of cells may comprise T cells. A population of cells may comprise clonally expanded T cells. A population of cells may comprise a polyclonal population of T cells. A population of cells may comprise natural killer (NK) cells. A population of cells may comprise T cells, B cells, NK cells, natural killer T cells (NKT), macrophages, dendritic cells, monocytes, innate-like lymphocytes (ILCs), or any combination thereof. In some embodiments, NK cells may be activated to secrete inflammatory cytokines such as IFN-γ and TNF-α to stimulate an immune response to target cells. In certain embodiments, NKT cells may secrete IL21 and IL2 to further stimulate a heightened immune response to target cells. The cell or these cell populations may be used in immunotherapies. The cell or these cell populations may be directed against a range of immune mediated diseases and cancers.

Cell-Based Immunotherapies

Immunotherapy may involve leveraging specialized immune cells to treat various diseases including cancer. This may be achieved by administering a patient's own immune cells or allogeneic immune cells that have been trained ex vivo to recognize a target antigen overexpressed by or associated with diseased cells, and selectively kill these diseased cells.

DC-based immunotherapy. Cell-based immunotherapies may involve administration of mature leukocytes or lymphocytes to a subject in need thereof. For example, naïve antigen presenting cells (APCs) may be isolated from a patient and pulsed or transfected with a target antigen that is overexpressed by tumor cells. These naïve APCs may be any host cell capable of presenting antigen on major histocompatibility complex molecules, including monocytes or dendritic cells (DCs). After isolation from a subject, APCs may be pulsed or transfected ex vivo with a target antigen that is overexpressed by tumor cells yielding mature, professional APCs that are capable of stimulating potent T cell responses. Mature APCs may be administered back into a patient to stimulate antigen specific T cell responses in vivo directed against target antigen-overexpressing immune cells. A recombinant CD20 of the disclosure, including a nucleotide encoding the amino acid of SEQ ID NO: 1, SEQ ID NO: 2, or SEQ ID NO: 3, may be used to develop mature CD20 antigen presenting cells. These CD20-specific APCs may be administered back into a patient to stimulate CD20 specific T cell responses in vivo.

CAR T cell therapy. Cell-based immunotherapies may also involve administration of genetically engineered lymphocytes to a subject. For example, chimeric antigen receptors (CAR) T cell therapy may involve isolation of T lymphocytes from a patient and genetic engineering of the T cell receptor to induce expression of chimeric antigen receptors that may be derived from the small chain variable fragment of an antibody specific for a target antigen. These T lymphocytes may be administered back into a subject, where they may be directed towards tumor cells that overexpress the target antigen. CAR T cells may be able to bind the target antigen expressed on diseased cells and carry out effector functions. The small chain variable fragment of an antibody specific for a CD20 of the disclosure, including CD20 sequences of SEQ ID NO: 1, SEQ ID NO: 2, or SEQ ID NO: 3, may be used to genetically engineer CAR T cells. These CAR T cells may be administered back into a subject, where they are directed towards cancer cells overexpressing the CD20 antigen.

Figure 2:
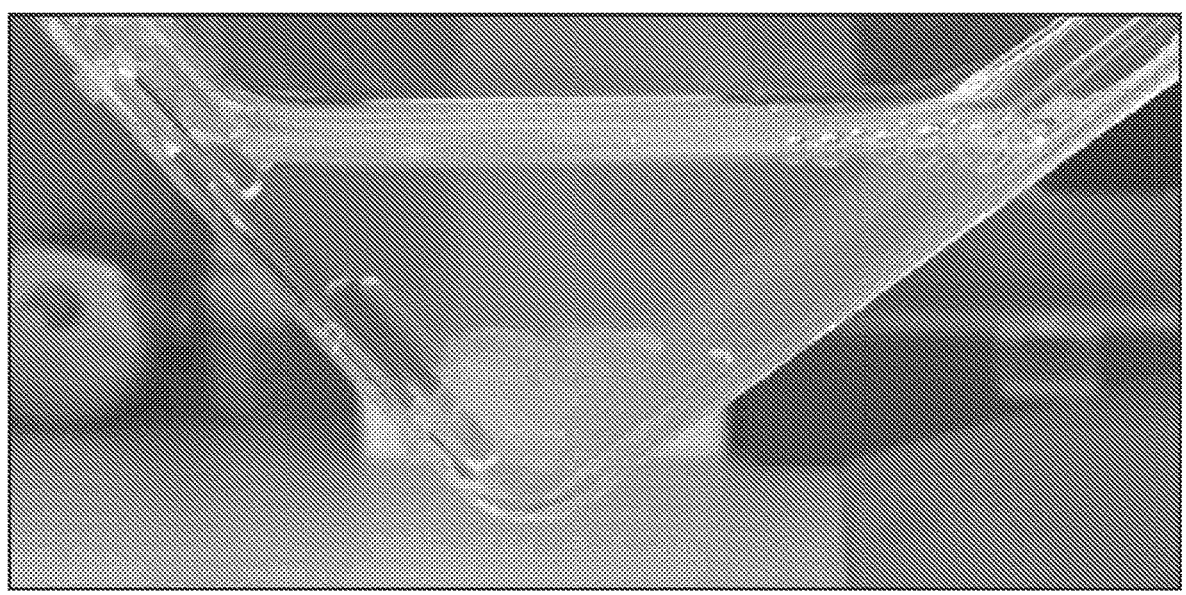
FIG. 2 shows fibrin/platelet clots after incubation of a culture flask containing cells from apheresis harvest.

Adoptive T cell therapy (ACT). Adoptive T cell therapy (ACT) may be another type of cell-based immunotherapy. ACT may involve isolation of mononuclear cells from a subject and ex vivo priming of lymphocytes into antigen specific cells by a feeder cell line presenting a target antigen that may be overexpressed by or associated with tumor cells. In some embodiments, the antigen specific cells may be polyclonal in nature. The antigen specific cells may be CD4+ T cells, CD8+ T cells, or any combination thereof. In other embodiments, the antigen specific cells may be primarily CD8+ T cells. In some embodiments, the present disclosure provides methods for isolation of mononuclear cells from a subject, ex vivo activation of antigen specific cells, and autologous adoptive T cell therapy in which the antigen specific cells may be infused back into the subject. Whole blood may be collected from a subject and layered over a Ficoll gradient for density centrifugation and separation of peripheral blood mononuclear cells (PBMCs). FIG. 1 shows cell layers that may be obtained by density centrifugation of whole blood. In alternate embodiments, PBMCs may be isolated from apheresis harvest and may be separated from fibrin clots and platelets as shown in FIG. 2. Isolated mononuclear cells may be resuspended in an induction media, which may include additional cytokines or proteins such as interleukin 21 or phytohemaglutinin. In some embodiments, the mononuclear cells may be cryopreserved before use in ex vivo co-culture with antigen presenting cells. The method of co-culture may impact the resulting antigen specific cells that are used in ACT.

Furthermore, other immune cells may be infused in ACT. Other immune cells may include natural killer cells (NK cells), macrophages, innate-like lymphocytes, natural killer T cells, and B cells. NK cells may be activated during the ex vivo co-culture comprising antigen presenting cells. NK cells also may boost the immune response when infused with the antigen specific cells.

In certain embodiments, antigen specific cells may be primed and may be expanded ex vivo by antigen presenting feeder cells that are presenting a target antigen. In some embodiments, the antigen presenting feeder cells that are presenting a target antigen may be irradiated. In some embodiments, the target antigen may be overexpressed by cancer cells. The target antigen may be an antigen associated with a cancer. The target antigen may be an antigen associated with the specific cancer from the subject to be treated. In other embodiments, the target antigen may be overexpressed by B or T lymphoma cells. In some embodiments, the target antigen may be a CD20 antigen or a fragment thereof. The CD20 antigen or the fragment thereof may be a canine CD20 or a fragment thereof, or a human C20 or a fragment thereof. The CD20 antigen or the fragment thereof may be a recombinant canine CD20 or a fragment thereof, a recombinant feline CD20 or a fragment thereof, or a recombinant human CD20 or a fragment thereof. In some embodiments, the recombinant CD20 or the fragment thereof may comprise a nucleotide sequence encoding the amino acid sequence of SEQ ID NO: 1 or a fragment thereof. In certain embodiments, the recombinant CD20 or the fragment thereof may comprise at least 70%, 75%, 80%, 85%, 90%, 95%, or 99% sequence identity to a nucleotide sequence encoding the amino acid sequence of SEQ ID NO: 1 or a fragment thereof. In other embodiments, the recombinant CD20 or the fragment thereof may comprise a nucleotide sequence encoding the amino acid sequence of SEQ ID NO: 2 or a fragment thereof. In certain embodiments, the recombinant CD20 or the fragment thereof may comprise at least 70%, 75%, 80%, 85%, 90%, 95%, or 99% sequence identity to a nucleotide sequence encoding an amino acid sequence of SEQ ID NO: 2 or a fragment thereof. In alternate embodiments, the CD20 or a fragment thereof may be a feline CD20 or a fragment thereof, or a recombinant feline CD20 or a fragment thereof. In other embodiments, the recombinant CD20 or the fragment thereof may comprise a nucleotide sequence encoding an amino acid sequence of SEQ ID NO: 3 or a fragment thereof. In certain embodiments, the recombinant CD20 or the fragment thereof may comprise at least 70%, 75%, 80%, 85%, 90%, 95%, or 99% sequence identity to a nucleotide sequence encoding an amino acid sequence of SEQ ID NO: 3 or a fragment thereof.

In some embodiments, the recombinant CD20 or the fragment thereof may comprise an amino acid sequence of SEQ ID NO: 1 or a fragment thereof. In certain embodiments, the recombinant CD20 or the fragment thereof may comprise at least 70%, 75%, 80%, 85%, 90%, 95%, or 99% sequence identity to an amino acid sequence of SEQ ID NO: 1 or a fragment thereof. In other embodiments, the recombinant CD20 or the fragment thereof may comprise an amino acid sequence of SEQ ID NO: 2 or a fragment thereof. In certain embodiments, the recombinant CD20 or a fragment thereof may comprise at least 70%, 75%, 80%, 85%, 90%, 95%, or 99% sequence identity to an amino acid sequence of SEQ ID NO: 2 or a fragment thereof. In alternate embodiments, the CD20 or the fragment thereof may be a feline CD20 or a fragment thereof, or a recombinant feline CD20 or a fragment thereof. In other embodiments, the recombinant CD20 or the fragment thereof may comprise an amino acid sequence of SEQ ID NO: 3 or a fragment thereof. In certain embodiments, the recombinant CD20 or the fragment thereof may comprise at least 70%, 75%, 80%, 85%, 90%, 95%, or 99% sequence identity to an amino acid sequence of SEQ ID NO: 3 or a fragment thereof.

The present disclosure provides methods of co-culturing feeder cells presenting a target antigen with isolated mononuclear cells to generate and expand a population of antigen specific T cells. Antigen presenting feeder cells presenting CD20 may be co-cultured with mononuclear cells isolated from a subject at varying ratios of feeder cells to mononuclear cells including 1:5, 1:4, 1:3, 1:2, 1:1, 2:1, 3:1, 4:1, or 5:1. The co-culture may be propagated for several days including 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, or 42 days. The co-culture may be propagated for several days including from 10 days to 42 days, 10 days to 40 days, 10 days to 35 days, 10 days to 30 days, 10 days to 25 days, 10 days to 20 days, 10 days to 15 days, 10 days to 12 days, 15 days to 42 days, 15 days to 30 days, 15 days to 25 days, 15 days to 20 days, 20 days to 42 days, 20 days 40 days, 20 days to 35 days, 20 days to 30 days, 20 days to 25 days, 25 days to 42 days, 25 days to 40 days, 25 days to 35 days, 25 days to 35 days, 25 days to 30 days, 30 days to 42 days, 30 days to 40 days, 30 days to 35 days, 35 days to 42 days, 35 days to 40 days, or 40 days to 42 days. In certain embodiments, the cells may reach a cell nadir by Day 7, and then IL-2 may be added and the cells may then proceed to reach maximum viable co-culture cell numbers by Day 21. In other embodiments, the cells may take longer to reach the nadir, and thus IL-2 may be added later after the cells have reached this nadir. In some embodiments, the cells may be kept in co-culture and supplemented with interleukins and growth factors as needed. In some embodiments co-culture of feeder cells and mononuclear cells may include additional cytokines such as an interleukin. In certain embodiments, the co-culture may be supplemented with interleukin 21 (IL-21), interleukin 2 (IL-2), or a combination of thereof. In some embodiments the co-culture may be supplemented with a recombinant human IL-21. In certain embodiments, the co-culture may be supplemented with a recombinant human IL-2. The co-culture may be supplemented with cytokines on any day of the co-culture and at several doses. For example, IL-21 may be added to the co-culture at least once, two times, three times, four times, or five times in the first week of co-culture. In certain embodiments, IL-21 may be added at a dose of 30 U/ml, 40 U/ml, 50 U/ml, 60 U/ml, 70 U/ml, 80 U/ml, 90 U/ml, 100 U/ml, 110 U/ml, 120 U/ml, 130 U/ml, 140 U/ml, 150 U/ml, 160 U/ml, 170 U/ml, 180 U/ml, 190 U/ml, 200 U/ml, 210 U/ml, 220 U/ml, 230 U/ml, 240 U/ml, 250 U/ml, 260 U/ml, 270 U/ml, 280 U/ml, 290 U/ml, or 300 U/ml. In certain embodiments, IL-21 may be added at a dose of from 30 U/ml to 300 U/ml, 30 U/ml to 250 U/ml, 30 U/ml to 200 U/ml, 30 U/ml to 150 U/ml, 30 U/ml to 100 U/ml, 30 U/ml to 50 U/ml, 50 U/ml to 300 U/ml, 50 U/ml to 250 U/ml, 50 U/ml to 200 U/ml, 50 U/ml to 150 U/ml, 50 U/ml to 100 U/ml, 100 U/ml to 300 U/ml, 100 U/ml to 250 U/ml, 100 U/ml to 200 U/ml, 100 U/ml to 150 U/ml, 150 U/ml to 300 U/ml, 150 U/ml to 250 U/ml, 150 U/ml to 200 U/ml, 40 U/ml to 80 U/ml, 40 U/ml to 70 U/ml, 40 U/ml to 60 U/ml, 40 U/ml to 50 U/ml, 60 U/ml to 100 U/ml, 60 U/ml to 90 U/ml, 60 U/ml to 80 U/ml, or 60 U/ml to 70 U/ml. In some embodiments, IL-21 and IL-2 may be added together, once, two times, three times, four times, or five times a week starting in the second week of the co-culture. IL-21 and IL-2 may be added at a dose of 30 U/ml, 40 U/ml, 50 U/ml, 60 U/ml, 70 U/ml, 80 U/ml, 90U/ml, 100 U/ml, 110 U/ml, 120 U/ml, 130 U/ml, 140 U/ml, 150 U/ml, 160 U/ml, 170 U/ml, 180 U/ml, 190 U/ml, 200 U/ml, 210 U/ml, 220 U/ml, 230 U/ml, 240 U/ml, 250 U/ml, 260 U/ml, 270 U/ml, 280 U/ml, 290 U/ml, or 300 U/ml. IL-21 and IL-2 may be added at a dose of from 30 U/ml to 300 U/ml, 30 U/ml to 250 U/ml, 30 U/ml to 200 U/ml, 30 U/ml to 150 U/ml, 30 U/ml to 100 U/ml, 30 U/ml to 50 U/ml, 50 U/ml to 300 U/ml, 50 U/ml to 250 U/ml, 50 U/ml to 200 U/ml, 50 U/ml to 150 U/ml, 50 U/ml to 100 U/ml, 100 U/ml to 300 U/ml, 100 U/ml to 250 U/ml, 100 U/ml to 200 U/ml, 100 U/ml to 150 U/ml, 150 U/ml to 300 U/ml, 150 U/ml to 250 U/ml, 150 U/ml to 200 U/ml, 40 U/ml to 80 U/ml, 40 U/ml to 70 U/ml, 40 U/ml to 60 U/ml, 40 U/ml to 50 U/ml, 60 U/ml to 100 U/ml, 60 U/ml to 90 U/ml, 60 U/ml to 80 U/ml, or 60 U/ml to 70 U/ml. In certain embodiments, IL-2 may be added at least once, two times, three times, four times, or five times a week in the second, third, fourth, fifth, or sixth week of the co-culture. IL-2 may be added at a dose of 30 U/ml, 40 U/ml, 50 U/ml, 60 U/ml, 70 U/ml, 80 U/ml, 90U/ml, 100 U/ml, 110 U/ml, 120 U/ml, 130 U/ml, 140 U/ml, 150 U/ml, 160 U/ml, 170 U/ml, 180 U/ml, 190 U/ml, 200 U/ml, 210 U/ml, 220 U/ml, 230 U/ml, 240 U/ml, 250 U/ml, 260 U/ml, 270 U/ml, 280 U/ml, 290 U/ml, or 300 U/ml. IL-2 may be added at a dose of from 30 U/ml to 300 U/ml, 30 U/ml to 250 U/ml, 30 U/ml to 200 U/ml, 30 U/ml to 150 U/ml, 30 U/ml to 100 U/ml, 30 U/ml to 50 U/ml, 50 U/ml to 300 U/ml, 50 U/ml to 250 U/ml, 50 U/ml to 200 U/ml, 50 U/ml to 150 U/ml, 50 U/ml to 100 U/ml, 100 U/ml to 300 U/ml, 100 U/ml to 250 U/ml, 100 U/ml to 200 U/ml, 100 U/ml to 150 U/ml, 150 U/ml to 300 U/ml, 150 U/ml to 250 U/ml, 150 U/ml to 200 U/ml, 40 U/ml to 80 U/ml, 40 U/ml to 70 U/ml, 40 U/ml to 60 U/ml, 40 U/ml to 50 U/ml, 60 U/ml to 100 U/ml, 60 U/ml to 90 U/ml, 60 U/ml to 80 U/ml, or 60 U/ml to 70 U/ml. In certain embodiments, 6 mM L-Glutamine may be added to the co-culture Day 1 through Day 7, which may suppress T regulatory cells expansion.

The co-culture may be supplemented with additional proteins such as phytohemaglutinin (PHA). PHA may be added at a dose of 10 ug/L, 20 ug/L, 30 ug/L, 40 ug/L, 50 ug/L, 60 ug/L, 70 ug/L, 80 ug/L, 90 ug/L, or 100 ug/L in the induction and propagation phases and at a dose of 10 ug/L, 20 ug/L, 30 ug/L, 40 ug/L, 50 ug/L, or 60 ug/L in the expansion phase. PHA may be added at a dose of from 10 ug/L to 100 ug/L, 20 ug/L to 100 ug/L, 30 ug/L to 100 ug/L, 40 ug/L to 100 ug/L, 50 ug/L to 100 ug/L, 60 ug/L to 100 ug/L, 70 ug/L to 100 ug/L, 80 ug/L to 100 ug/L, 90 ug/L to 100 ug/L, or 20 ug/L to 60 ug/L in the induction and propagation phases and at a dose of from 10 ug/L to 60 ug/L, 20 ug/L to 60 ug/L, 30 ug/L to 60 ug/L, 40 ug/L to 60 ug/L, 50 ug/L to 60 ug/L, or 20 ug/L to 40 ug/L in the expansion phase. In some embodiments, T cell activating antibodies may be added to the co-culture. For example, an anti-CD3 antibody may be added to the co-culture. The anti-CD3 antibody may be added at a dose of 2 ug/ml, 4 ug/ml, 6 ug/ml, 8 ug/ml, 10 ug/ml, 12 ug/ml, or 14 ug/ml beginning on Day 1 and ending on Day 14. The anti-CD3 antibody may be added at a dose of 2 ug/ml, 4 ug/ml, 6 ug/ml, 8 ug/ml, 10 ug/ml, 12 ug/ml, or 14 ug/ml beginning on Day 1, Day 2, Day 3, or Day 4 and ending on Day 12, Day 13, Day 14, Day 15, or Day 16. The anti-CD3 antibody may be added at a dose of from 2 ug/ml to 14 ug/ml, 2 ug/ml to 10 ug/ml, 2 ug/ml to 8 mg/ml, 2 ug/ml to 6 mg/ml, 2 ug/ml to 4 ug/ml, 4 ug/ml to 14 ug/ml, 4 ug/ml to 10 ug/ml, 4 ug/ml to 8 mg/ml, 4 ug/ml to 6 mg/ml, 6 ug/ml to 14 mg/ml, 6 ug/ml to 10 ug/ml, 6 ug/ml to 8 mg/ml, 8 ug/ml to 14 mg/ml, 8 ug/ml to 10 ug/ml, 10 ug/ml to 14 mg/ml, 10 ug/ml to 12 mg/ml, or 12 ug/ml to 14 ug/ml beginning on Day 1 and ending on Day 14. The anti-CD3 antibody may be added at a dose of from 2 ug/ml to 14 ug/ml, 2 ug/ml to 10 ug/ml, 2 ug/ml to 8 mg/ml, 2 ug/ml to 6 mg/ml, 2 ug/ml to 4 ug/ml, 4 ug/ml to 14 ug/ml, 4 ug/ml to 10 ug/ml, 4 ug/ml to 8 mg/ml, 4 ug/ml to 6 mg/ml, 6 ug/ml to 14 mg/ml, 6 ug/ml to 10 ug/ml, 6 ug/ml to 8 mg/ml, 8 ug/ml to 14 mg/ml, 8 ug/ml to 10 ug/ml, 10 ug/ml to 14 mg/ml, 10 ug/ml to 12 mg/ml, or 12 ug/ml to 14 ug/ml beginning on Day 1, Day 2, Day 3, or Day 4 and ending on Day 12, Day 13, Day 14, Day 15, or Day 16.

In some embodiments, the co-culture may also be supplemented with autologous or allogeneic tumor cell membrane preparations at a rate of 1 ml/l, 10 ml/l, or 20 ml/l, and may be added to co-cultures Day 1 through Day 21 of the co-culture. For example, the membrane extracts may be derived from autologous tumor cells or allogeneic tumor cells and may be pulsed in ABT-2 cells or ABT-2+ cells to allow for additional presentation of tumor antigens. The membranes may be prepared by exposing tumor cells to three freeze/thaw cycles using liquid nitrogen at −120° C. for five minutes and thawing cells to 37° C. This may result in swelling and ice crystal formation that disrupts cells and the resulting cells may be centrifuged at 3000 rpm for 10 minutes. The supernatant may be discarded and the tumor cell pellet containing membrane extracts may be added to the co-culture as described above.

In some embodiments, the co-culture may be supplemented with additional antigen presenting feeder cells presenting a target antigen such as CD20 or a fragment thereof. For example, a CD20 or fragment thereof presenting, irradiated antigen presenting feeder cells may be added to the co-culture every 2 days, 3 days, 4 days, 5 days, 6 days, 7 days, 8 days, 9 days, or 10 days of the co-culture. In some embodiments, co-culture of feeder cells with mononuclear cells isolated from a subject may result in expansion of a plurality of cells that may include antigen specific cells and activated cells. In some embodiments, co-culture of feeder cells with mononuclear cells isolated from a subject may result in expansion of the antigen specific, effector T cells of the disclosure. In some embodiments, the antigen specific cells may be CD4+ T cells, CD8+ T cells, or a combination of both. In further embodiments, the activated cells may be NK cells. In some embodiments, the plurality of cells may comprise over 30%, over 40%, over 50%, over 60%, over 70%, over 80%, over 90%, or 100% antigen specific cells. In some embodiments, antigen specific cells may comprise over 30%, over 40%, over 50%, over 60%, over 70%, over 80%, over 90%, or 100% CD8+ T cells. In some embodiments, the antigen specific cells may kill cancer cells. The cancer cells may express the target antigen. In certain embodiments the cancer cells may overexpress the target antigen. In certain embodiments, the cancer cells may be B cell lymphoma cells or T cell lymphoma cells. In other embodiments, the cancer cells may be osteosarcoma, hemangiosarcoma, multiple myeloma, or plasma tumor cells. In some embodiments, the present disclosure methods for producing the antigen specific cells that comprise the cells used in adoptive T cell therapy.

Figure 3:
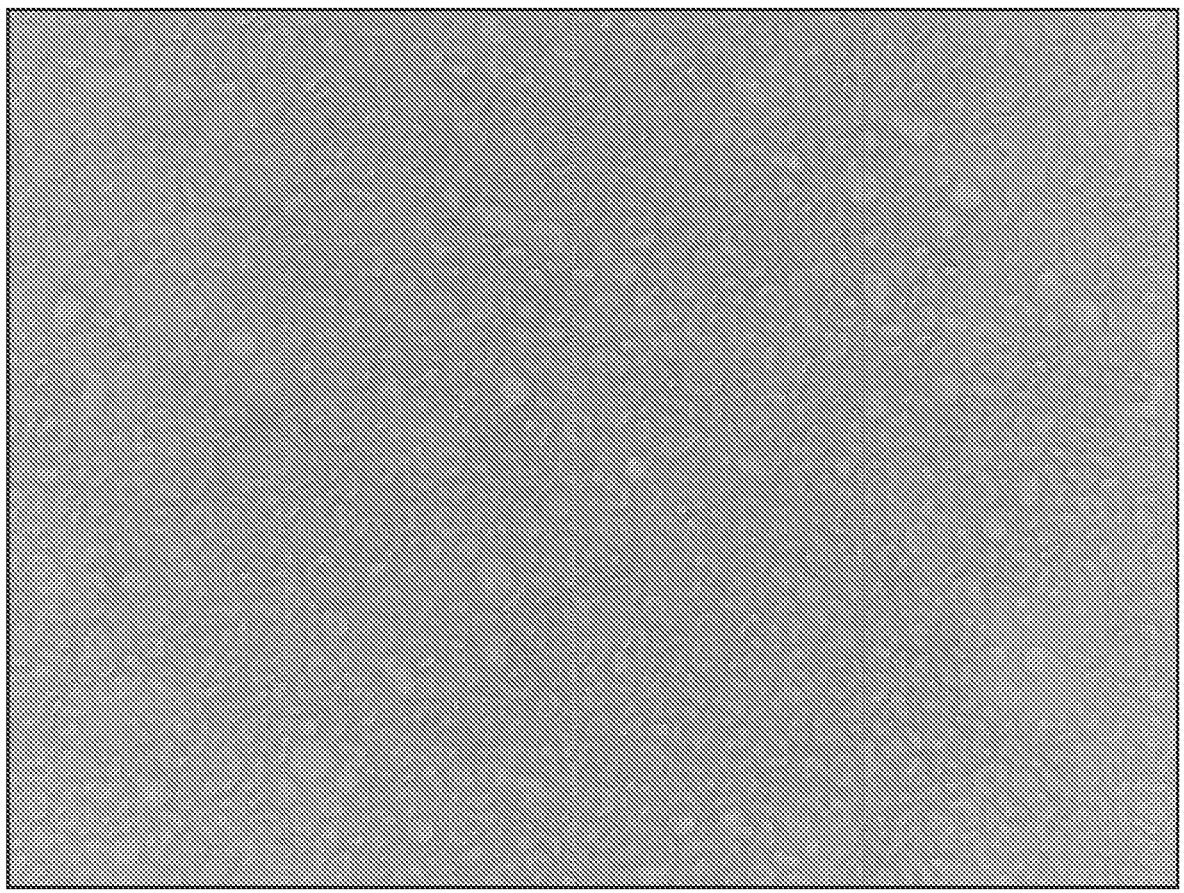
FIG. 3 shows ABT-2+ Gy cells and peripheral blood mononuclear cells (PBMCs) at Day 7 of the co-culture, by which point unresponsive cells isolated from density centrifugation have died.
Figure 4:
FIG. 4 shows T cells bound in clusters around ABT-2+ Gy cells at Day 7 of the co-culture.
Figure 5:
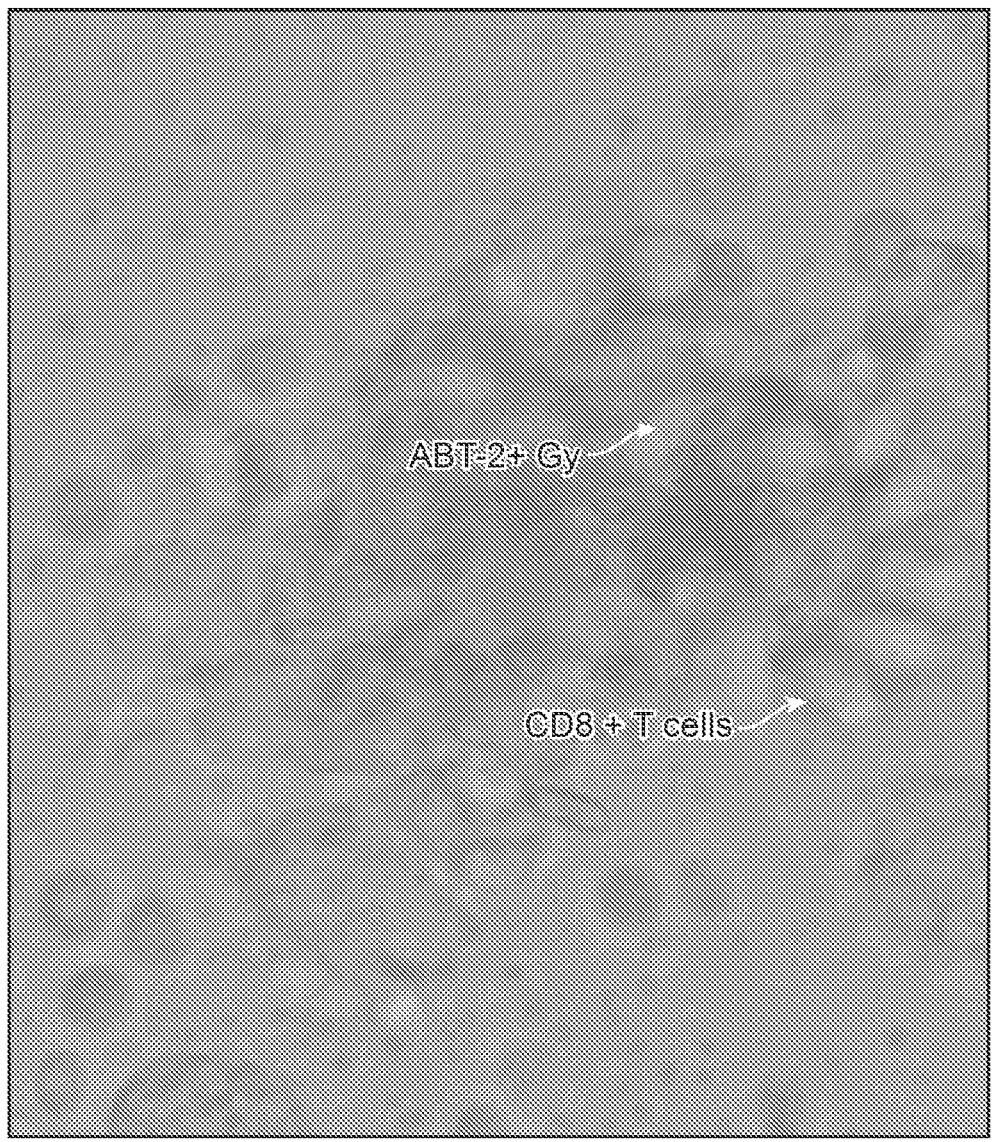
FIG. 5 shows CD8+ T cells bound in clusters around ABT-2+ Gy cells at Day 11 of the co-culture.
Figure 6:
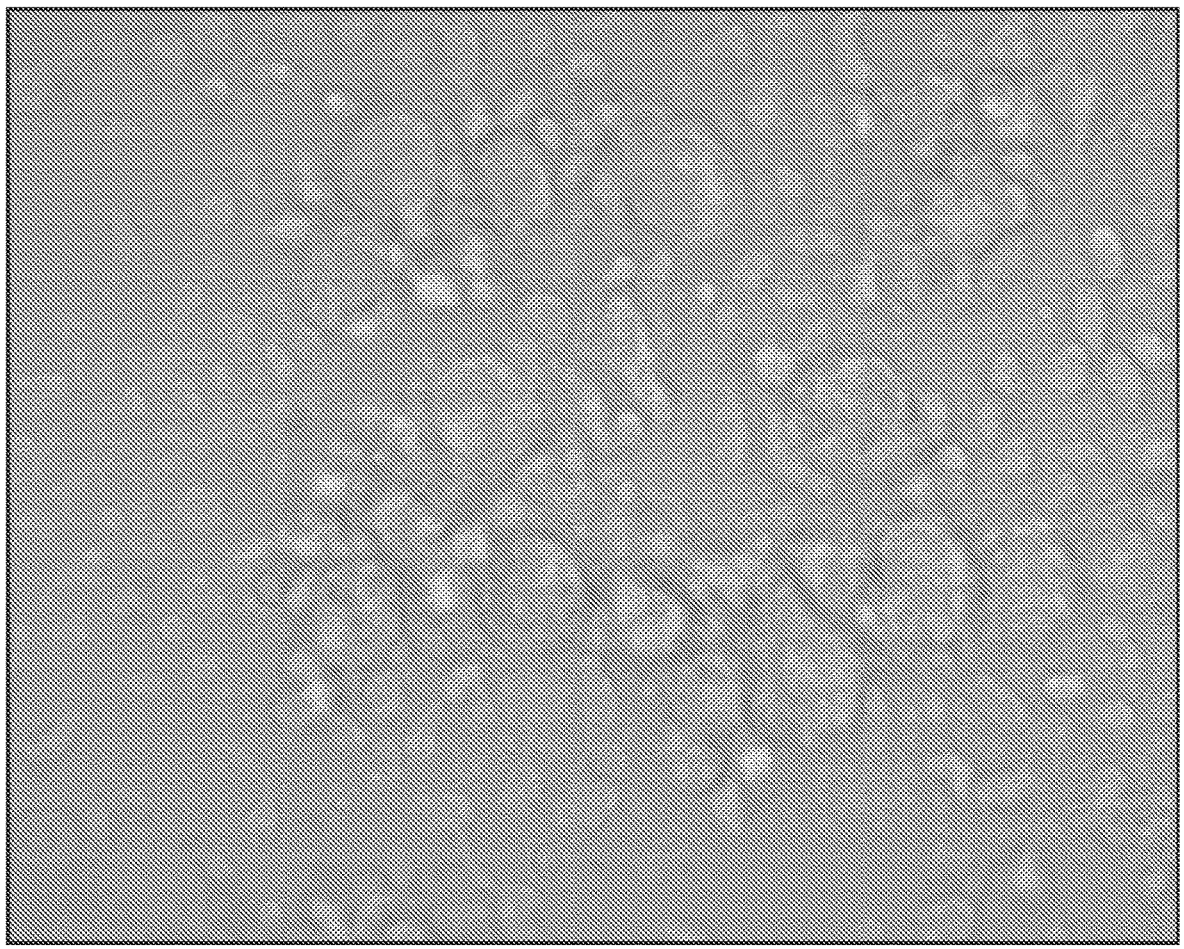
FIG. 6 shows T cells attached to ABT-2+ Gy cells at Day 14 of the co-culture.
Figure 7:
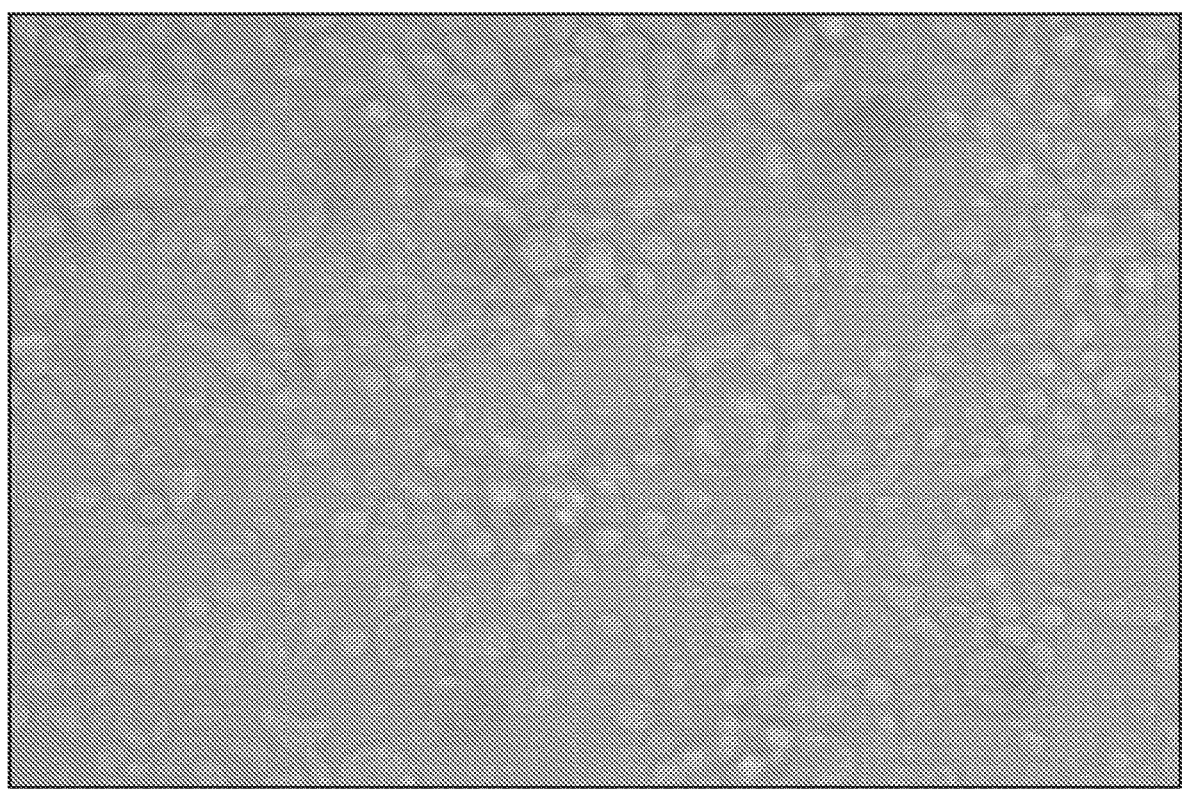
FIG. 7 shows T cells attached to ABT-2+ Gy cells at Day 16 of the co-culture.
Figure 8:
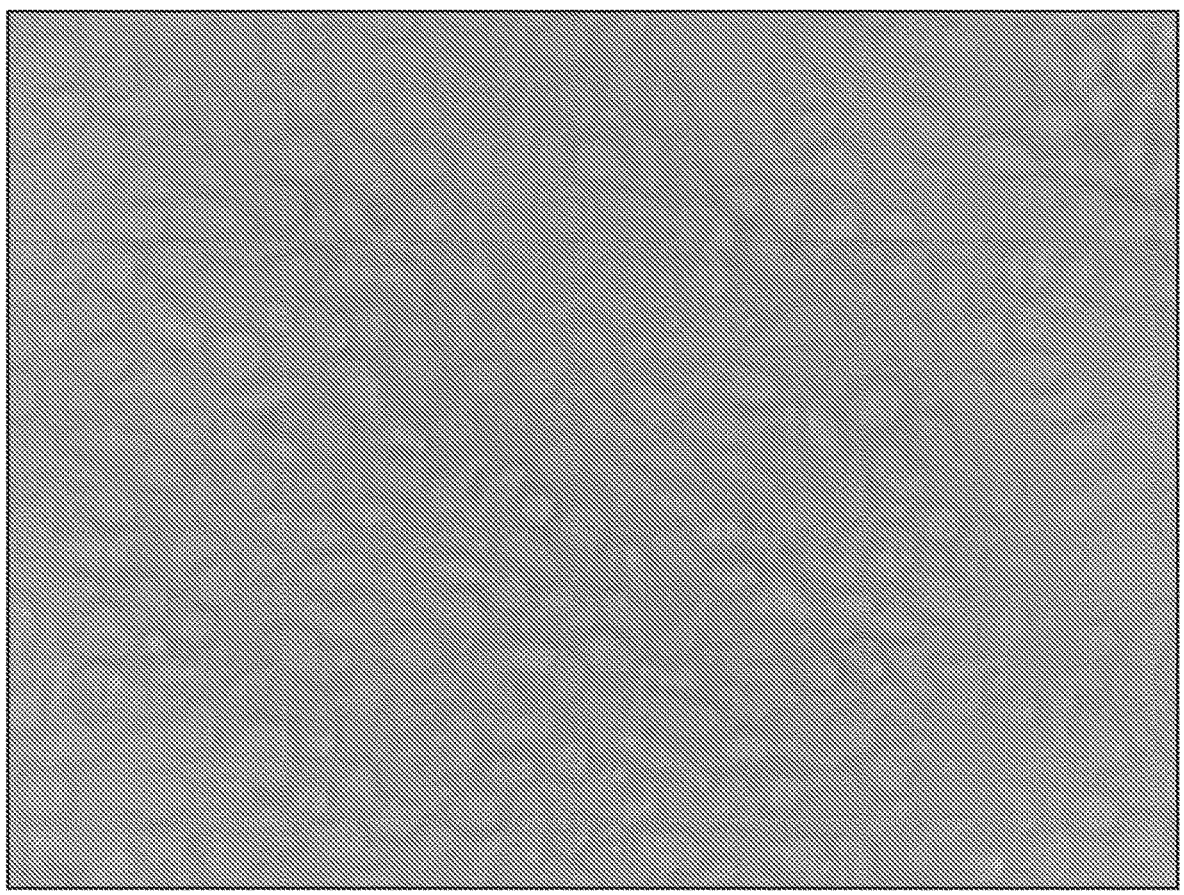
FIG. 8 shows clonal expansions of T cells at Day 12 of the co-culture, by which point all T cells were oriented in an end-to-end manner.
Figure 9:
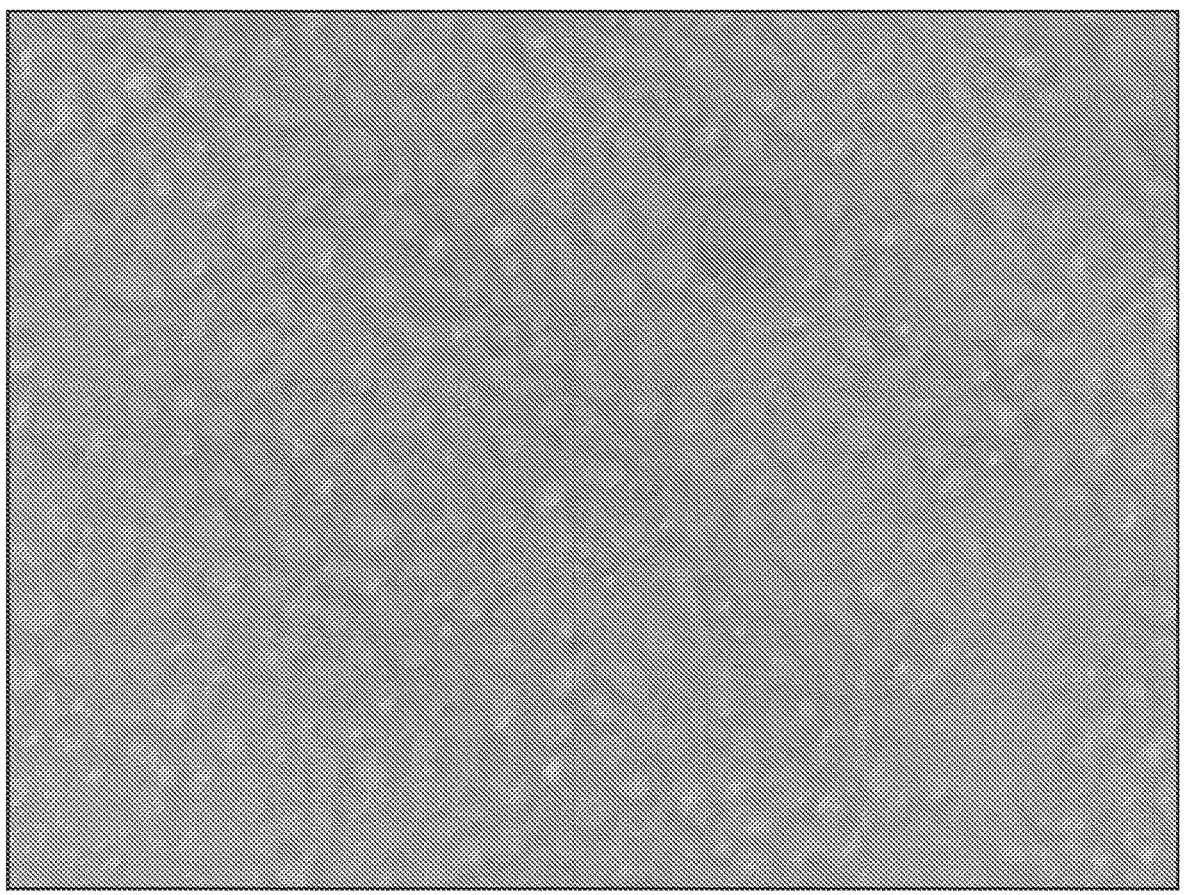
FIG. 9 shows T cells at the final stage of expansion on Day 21 at which point cells covered the surface of a flask in a confluent layer.
Figure 13:
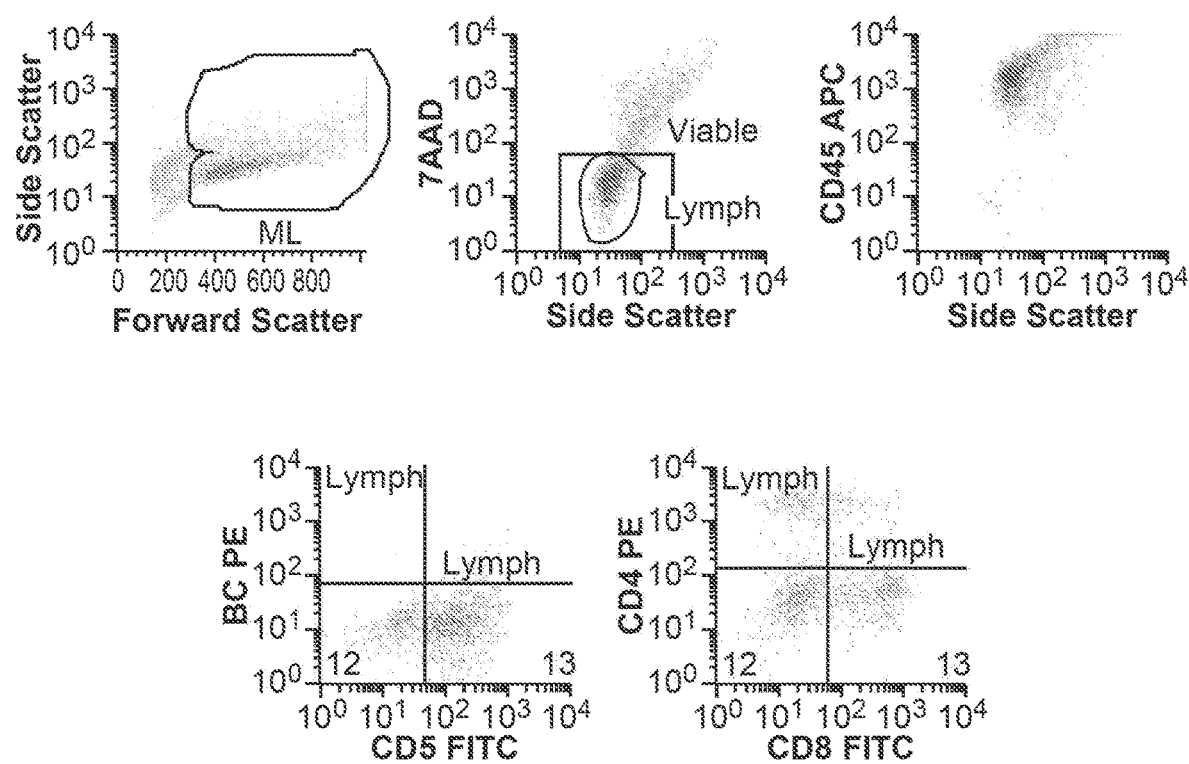
FIG. 13 shows flow cytometry dot plots of cell populations from the adoptive T cell therapy (ACT) prepared for infusion in patient GS.
Figure 14:
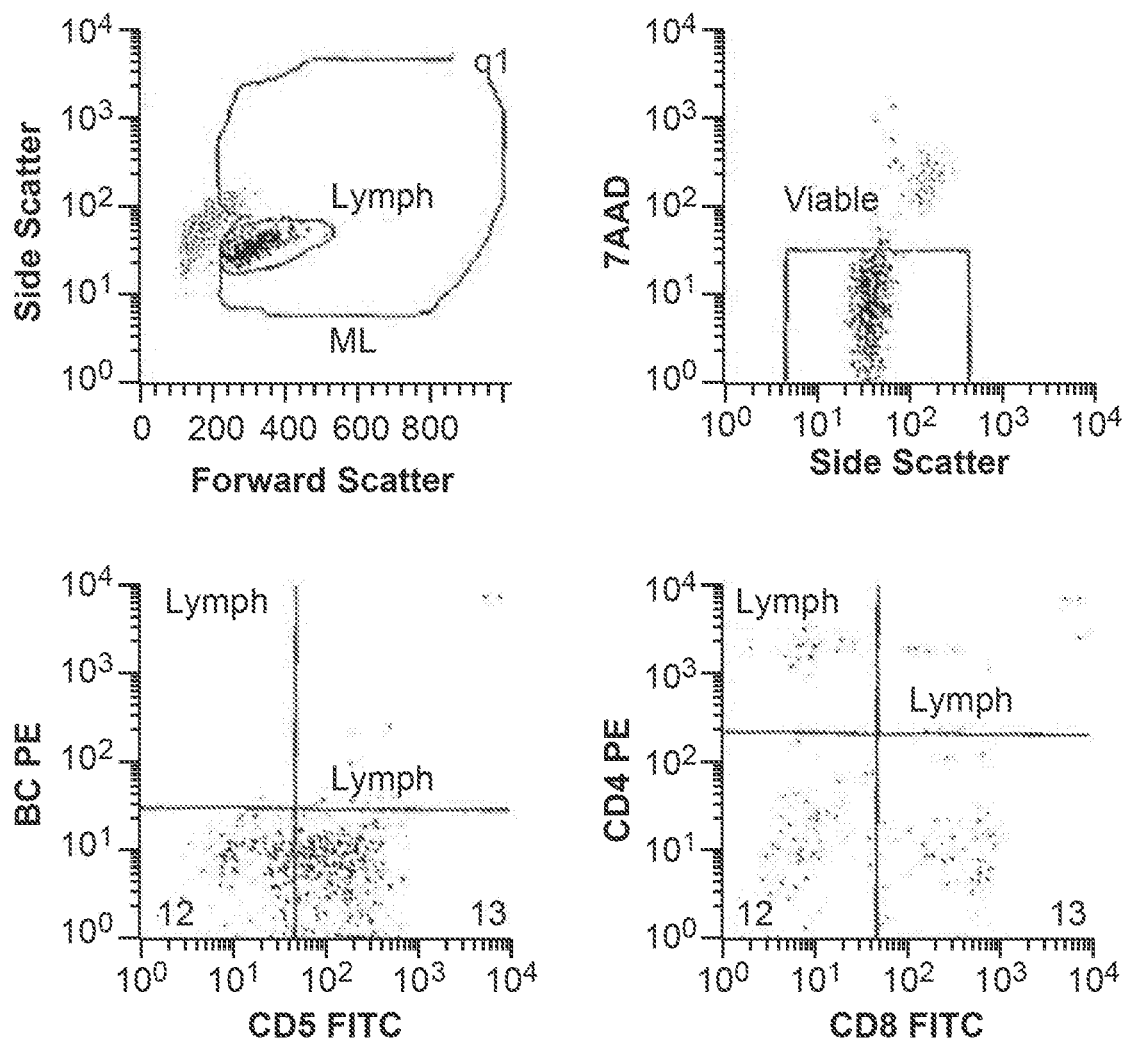
FIG. 14 shows flow cytometry dot plots of cell populations from Day 21 of the ABT2+ Gy cells and PBMC co-culture.
Figure 17:
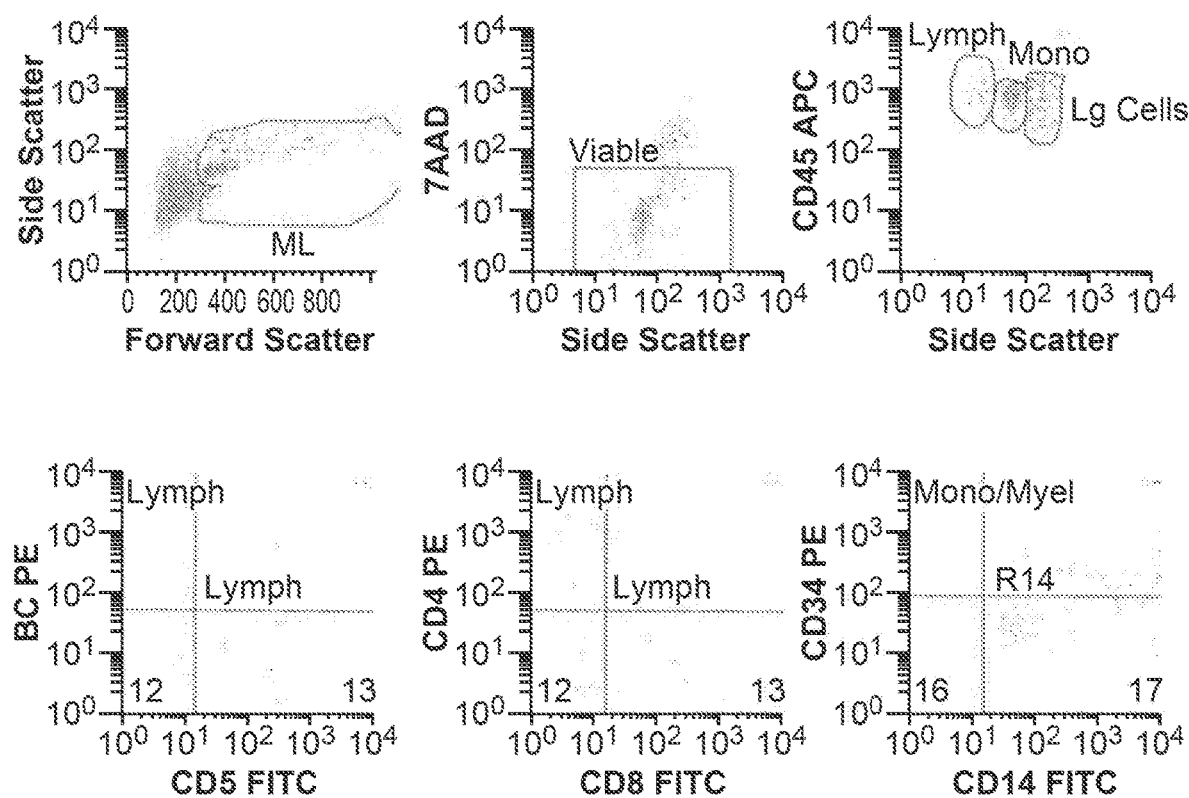
FIG. 17 shows flow cytometry dot plots of cell populations from Day 8 of the ABT2+ Gy cells and PBMC co-culture grown in flasks.
Figure 18:
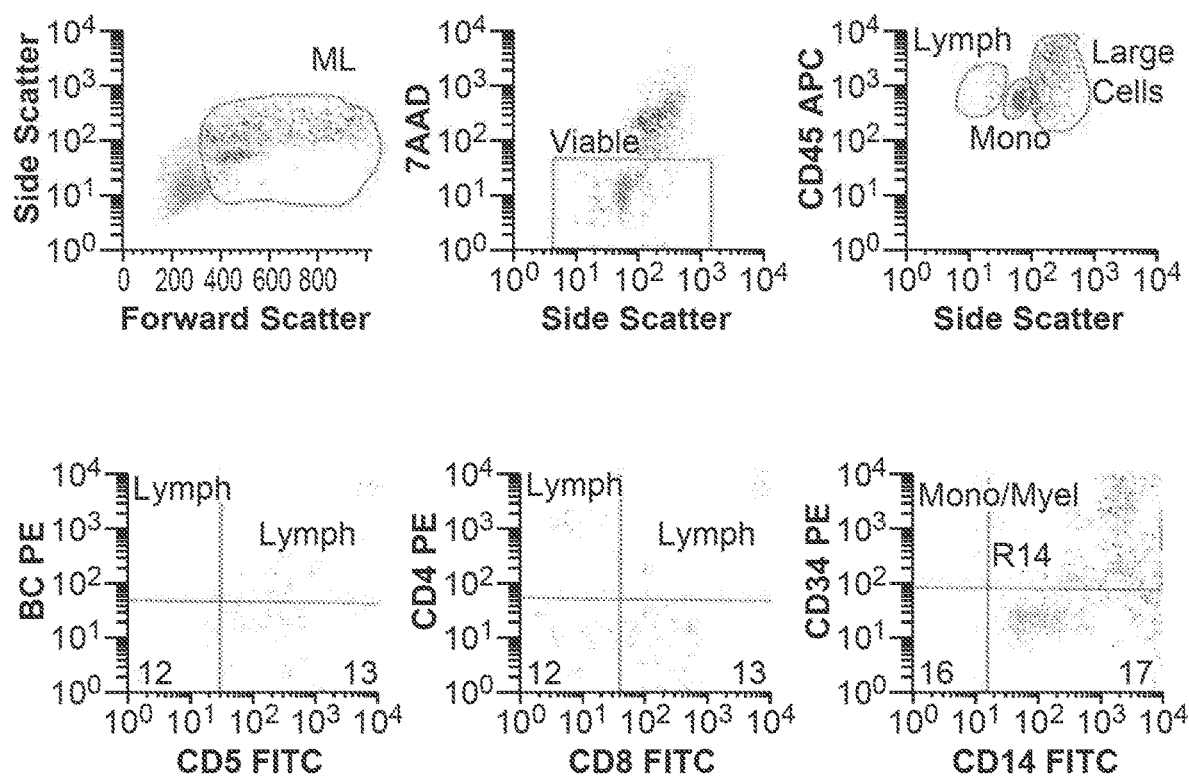
FIG. 18 shows flow cytometry dot plots of cell populations from Day 8 of a co-culture of ABT2+ Gy cells and PBMCs different from the co-culture of FIG. 17 and grown in wells.

FIG. 3-FIG. 9 show the co-culture at various stages of the priming process. For example, FIG. 3 shows the co-culture at Day 7 by which time mononuclear cells unresponsive to antigen presentation by feeder cells may die. During T cell priming, T cells may cluster around irradiated feeder cells, as shown in FIG. 4 at Day 7 and FIG. 5 at Day 11. FIG. 8 shows the expanded population of antigen specific T cells at Day 12. At later stages of the co-culture, all surviving antigen presenting feeder cells may have attached T cells as shown in FIG. 6 at Day 14 and FIG. 7 at Day 16. By Day 21, the antigen specific T cells may be expanded to cover the flask in a confluent layer, as shown in FIG. 9. FIG. 13 shows flow cytometry dot plots of T cells that were infused into patient GS according to Table 4. FIG. 14 shows flow cytometry dot plots enumerating the composition of cells in the culture 21 days after growth. Importantly, the CD4+ T cell to CD8+ T cell ratio was 18:33. FIG. 17 shows flow cytometry dot plots enumerating the composition of cells at Day 8 of the co-culture and the CD4+ T cell to CD8+ T cell ratio was 35:47. FIG. 18 shows flow cytometry dot plots enumerating the composition of cells at Day 8 of a co-culture different from FIG. 17. The CD4+ to CD8+ T cell ratio was 20:61.

In certain embodiments, the co-culture may also be propagated by addition of feeder cells pulsed with tumor cell membrane extracts. In this case, the co-culture may additionally give rise to tumor-specific T cells that may be administered to a subject in need thereof. In some embodiments, the subject may have osteosarcoma or hemangio sarcoma.

Conditioning

A subject in need of treatment for a cancer may be treated with standard chemotherapy protocols. The present disclosure provides methods for conditioning a subject prior to administration of adoptive T cell therapy (ACT). In some embodiments, the method of conditioning may involve treating a subject with a standard multi-agent chemotherapy and consolidating with a high dose chemotherapy or total body irradiation. In certain embodiments, the standard induction chemotherapy may include CHOP therapy including cyclophosphamide, doxorubicin, vincristine, and prednisone. For example, CHOP therapy may be administered according to the dosing regimen set forth in Table 1. In some embodiments, consolidation of standard multi-agent therapy may be achieved with a dose of cyclophosphamide. Cyclophosphamide may be administered at a dose of 200 mg/m$^2$, 250 mg/m$^2$, 300 mg/m$^2$, 350 mg/m$^2$, 400 mg/m$^2$, 450 mg/m$^2$, 500 mg/m$^2$, 550 mg/m$^2$, 600 mg/m$^2$, 650 mg/m$^2$, 700 mg/m$^2$, 750 mg/m$^2$, or 800 mg/m$^2$. In some embodiments, the high dose of cyclophosphamide may be administered at a dose of from 250 mg/m$^2$-300 mg/m$^2$, 300 mg/m$^2$-350 mg/m$^2$, 350 mg/m$^2$-400 mg/m$^2$, 400 mg/m$^2$-450 mg/m$^2$, 450 mg/m$^2$-500 mg/m$^2$, 500 mg/m$^2$-550 mg/m$^2$, 550 mg/m$^2$-600 mg/m$^2$, or 600 mg/m$^2$-650 mg/m$^2$. In alternate embodiments, consolidation of standard multi-agent therapy may be achieved with total body irradiation. Total body irradiation may be carried out by exposing a subject to a dose of gamma irradiation. The present disclosure provides methods for exposing a subject to a dose of gamma irradiation including 2 Gy, 3 Gy, 4 Gy, 5 Gy, 6 Gy, 7 Gy, 8 Gy, 9 Gy, 10 Gy, 11 Gy, or 12 Gy. In some embodiments, the dose of gamma irradiation may be from 2-12 Gy. In other embodiments, the dose of gamma irradiation may be from 2-4 Gy, 4-6 Gy, 6-8 Gy, 8-10 Gy, or 10-12 Gy. The subject may be rescued with a dose of autologous or allogeneic CD34+ cells administered at a dose of from $0.5 \times 10^6$-$10 \times 10^6$ cells/kg. In some embodiments, the subject may be rescued with a dose of autologous or allogeneic CD34+ cells administered at a dose of from $0.5 \times 10^6$-$2 \times 10^6$ cells/kg, $2 \times 10^6$-$4 \times 10^6$ cells/kg, $4 \times 10^6$-$6 \times 10^6$ cells/kg, $6 \times 10^6$-$8 \times 10^6$ cells/kg, or $8 \times 10^6$-$10 \times 10^6$ cells/kg. In some embodiments, the present disclosure provides methods for conditioning of a subject that may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days prior to the date of the first ACT infusion. In some embodiments, the present disclosure provides methods for conditioning of a subject that may be administered from 1 day to 20 days, 1 day to 15 days, 1 day to 10 days, 1 day to 5 days, 5 days to 20 days, 5 days to 15 days, 5 days to 10 days, 10 days to 20 days, 10 days to 15 days, or 15 days to 20 days prior to the date of the first ACT infusion.

In alternate embodiments, the subject may be conditioned with a truncated induction chemotherapy protocol that may include L-asparaginase, vincristine, doxorubicin, and cyclophosphamide. L-asparaginase may be administered subcutaneously at a dose of 10,000 IU/m$^2$, vincristine may be administered intravenously at a dose of 0.7 mg/m$^2$, doxorubicin may be administered intravenously at 30 mg/m$^2$, and cyclophosphamide may be administered intravenously at 500 mg/m$^2$. L-asparaginase may be administered subcutaneously at a dose of about 10,000 IU/m$^2$, vincristine may be administered intravenously at a dose of about 0.7 mg/m$^2$, doxorubicin may be administered intravenously at about 30 mg/m$^2$, and cyclophosphamide may be administered intravenously at about 500 mg/m$^2$. In certain embodiments, the cyclophosphamide may be administered orally. Conditioning of a subject with the truncated induction chemotherapy may be administered 10 days, 11 days, 12 days, 13 days, 14 days, 15 days, 16 days, 17 days, 18 days, 19 days, or 20 days prior to the date of the first ACT infusion. Conditioning of a subject with the truncated induction chemotherapy may be administered from 10 days to 20 days, 10 days to 18 days, 10 days to 16 days, 10 days to 14 days, 10 days to 12 days, 12 days to 20 days, 12 days to 18 days, 12 days to 16 days, 12 days to 14 days, 14 days to 20 days, 14 days to 18 days, 14 days to 16 days, 16 days to 20 days, 16 days to 18 days, or 18 days to 20 days prior to the date of the first ACT infusion.

Administration

Subjects in need thereof may be treated by administering the cells with the methods of administration of the present disclosure. In some embodiments the subject may be a canine. In other embodiments, the subject may be a human. In alternate embodiments, the subject may be a feline. The subject may have a cancer, such as B cell lymphoma, T cell lymphoma, osteosarcoma, hemangiosarcoma, multiple myeloma, or a plasma tumor. In some embodiments, the present disclosure provides treatment of a subject with a cancer overexpressing CD20 antigen, including B cell lymphoma. In other embodiments, the subject may have an autoimmune disease or an auto-inflammatory disease that is B cell mediated. In certain embodiments, the antigen specific cell of the disclosure is administered to a subject in need thereof as a form of adoptive T cell therapy. In some embodiments, administration may be performed by infusion via a peripheral vein catheter.

In some embodiments, the subject may be conditioned according to any of the methods described above prior to infusion of the ACT. For example, the subject may be administered CHOP therapy followed by high-dose cyclophosphamide or total body irradiation. In other embodiments, the subject may be further administered any of the chemotherapies used in conditioning during or after administration of the ACT infusion.

The antigen specific cell may be administered to a subject at a first dose, a second dose, a third dose, or any combination thereof. In some embodiments the first dose may be infused at a rate of $5\times10^5$ cells/m$^2$ $5\times10^6$ cells/m$^2$, $5\times10^7$ cells/m$^2$, $5\times10^8$ cells/m$^2$, $5\times10^9$ cells/m$^2$, or $5\times10^{10}$ cells/m$^2$. In some embodiments the first dose may be infused at a rate of from $5\times10^5$ cells/m$^2$ to $5\times10^{10}$ cells/m$^2$, $5\times10^5$ cells/m$^2$ to $5\times10^9$ cells/m$^2$, $5\times10^5$ cells/m$^2$ to $5\times10^8$ cells/m$^2$, $5\times10^5$ cells/m$^2$ to $5\times10^7$ cells/m$^2$, $5\times10^5$ cells/m$^2$ to $5\times10^6$ cells/m$^2$, $5\times10^6$ cells/m$^2$ to $5\times10^{10}$ cells/m$^2$, $5\times10^6$ cells/m$^2$ to $5\times10^9$ cells/m$^2$, $5\times10^6$ cells/m$^2$ to $5\times10^8$ cells/m$^2$, $5\times10^6$ cells/m$^2$ to $5\times10^7$ cells/m$^2$, $5\times10^7$ cells/m$^2$ to $5\times10^{10}$ cells/m$^2$, $5\times10^7$ cells/m$^2$ to $5\times10^9$ cells/m$^2$, $5\times10^7$ cells/m$^2$ to $5\times10^8$ cells/m$^2$, $5\times10^8$ cells/m$^2$ to $5\times10^{10}$ cells/m$^2$, $5\times10^8$ cells/m$^2$ to $5\times10^9$ cells/m$^2$, or $5\times10^9$ cells/m$^2$ to $5\times10^{10}$ cells/m$^2$. In some embodiments the second dose may be infused at a rate of $5\times10^5$ cells/m$^2$, $5\times10^6$ cells/m2, $5\times10^7$ cells/m$^2$, $5\times10^8$ cells/m$^2$, $5\times10^9$ cells/m$^2$, or $5\times10^{10}$ cells/m$^2$. In some embodiments the second dose may be infused at a rate of from $5\times10^5$ cells/m$^2$ to $5\times10^{10}$ cells/m$^2$, $5\times10^5$ cells/m$^2$ to $5\times10^9$ cells/m$^2$, $5\times10^5$ cells/m$^2$ to $5\times10^8$ cells/m$^2$, $5\times10^5$ cells/m$^2$ to $5\times10^7$ cells/m$^2$, $5\times10^5$ cells/m$^2$ to $5\times10^6$ cells/m$^2$, $5\times10^6$ cells/m$^2$ to $5\times10^{10}$ cells/m$^2$, $5\times10^6$ cells/m$^2$ to $5\times10^9$ cells/m$^2$, $5\times10^6$ cells/m$^2$ to $5\times10^8$ cells/m$^2$, $5\times10^6$ cells/m$^2$ to $5\times10^7$ cells/m$^2$, $5\times10^7$ cells/m$^2$ to $5\times10^{10}$ cells/m$^2$, $5\times10^7$ cells/m$^2$ to $5\times10^9$ cells/m$^2$, $5\times10^7$ cells/m$^2$ to $5\times10^8$ cells/m$^2$, $5\times10^8$ cells/m$^2$ to $5\times10^{10}$ cells/m$^2$, $5\times10^8$ cells/m$^2$ to $5\times10^9$ cells/m$^2$, or $5\times10^9$ cells/m$^2$ to $5\times10^{10}$ cells/m$^2$. In some embodiments the third dose may be infused at a rate of $5\times10^5$ cells/m$^2$, $5\times10^6$ cells/m$^2$, $5\times10^7$ cells/m$^2$, $5\times10^8$ cells/m$^2$, $5\times10^9$ cells/m2, or $5\times10^{10}$ cells/m$^2$. In some embodiments the third dose may be infused at a rate of from $5\times10^5$ cells/m$^2$ to $5\times10^{10}$ cells/m$^2$, $5\times10^5$ cells/m$^2$ to $5\times10^9$ cells/m$^2$, $5\times10^5$ cells/m$^2$ to $5\times10^8$ cells/m$^2$, $5\times10^5$ cells/m$^2$ to $5\times10^7$ cells/m$^2$, $5\times10^5$ cells/m$^2$ to $5\times10^6$ cells/m$^2$, $5\times10^6$ cells/m$^2$ to $5\times10^{10}$ cells/m$^2$, $5\times10^6$ cells/m$^2$ to $5\times10^9$ cells/m$^2$, $5\times10^6$ cells/m$^2$ to $5\times10^8$ cells/m$^2$, $5\times10^6$ cells/m$^2$ to $5\times10^7$ cells/m$^2$, $5\times10^7$ cells/m$^2$ to $5\times10^{10}$ cells/m$^2$, $5\times10^7$ cells/m$^2$ to $5\times10^9$ cells/m$^2$, $5\times10^7$ cells/m$^2$ to $5\times10^8$ cells/m$^2$, $5\times10^8$ cells/m$^2$ to $5\times10^{10}$ cells/m$^2$, $5\times10^8$ cells/m$^2$ to $5\times10^9$ cells/m$^2$, or $5\times10^9$ cells/m$^2$ to $5\times10^{10}$ cells/m$^2$. In certain embodiments, the second dose may be administered 4 days, 5 days, 6 days, 7 days, 8 days, 9 days, 10 days, 11 days, 12 days, 13 days, or 14 days after the first dose. In certain embodiments, the second dose may be administered from 4 days to 14 days, 4 days to 10 days, 4 days to 6 days, 6 days to 14 days, 6 days to 10 days, 6 days to 8 days, 8 days to 14 days, 8 days to 10 days, 10 days to 12 days, or 12 days to 14 days after the first dose. In further embodiments, the third dose may be infused 2 weeks, 3 weeks, 4 weeks, 5 weeks, 6 weeks, 7 weeks, or 8 weeks after the first dose. In further embodiments, the third dose may be infused from 2 weeks to 3 weeks, 2 weeks to 4 weeks, 2 weeks to 5 weeks, 2 weeks to 6 weeks, 2 weeks to 7 weeks, 2 weeks to 8 weeks, 3 weeks to 4 weeks, 3 weeks to 5 weeks, 3 weeks to 6 weeks, 3 weeks to 7 weeks, 3 weeks to 8 weeks, 4 weeks to 5 weeks, 4 weeks to 6 weeks, 4 weeks to 7 weeks, 4 weeks to 8 weeks, 5 weeks to 6 weeks, 5 weeks to 7 weeks, 5 weeks to 8 weeks, 6 weeks to 7 weeks, 6 weeks to 8 weeks, or 7 weeks to 8 weeks after the first dose.

Treatment of Diseases

The adoptive T cell therapy (ACT) of the present disclosure may be used to treat diseases in a subject in need thereof. Also provided are methods of treatment of diseases with the ACT of the present disclosure. In some embodiments, the ACT of the present disclosure may be used to treat a range of diseases including cancer. In other embodiments, the ACT of the present disclosure may be used to treat autoimmune diseases, and auto inflammatory diseases.

Lymphomas. Lymphomas are a family of cancers, which may affect immune cells in the hematopoietic and lymphatic systems. Lymphomas may be Hodgkin's lymphomas, non-Hodgkin's lymphomas, multiple myelomas, or any immune-proliferative cancer. Lymphomas may affect B cells, T cells, and NK cells, and may be classified as high grade or low grade tumors depending on the stage of disease. Types of non-Hodgkin B cell lymphomas may include diffuse large B cell lymphoma, follicular lymphoma, marginal zone B cell lymphoma, Burkitt lymphoma, lymphoplasmacytic lymphoma, hairy cell leukemia, and primary central nervous system lymphoma. Types of non-Hodgkin T cell lymphomas may include precursor T-lymphoblastic lymphoma/leukemia and several subtypes of peripheral T cell lymphoma. Cells associated with these B or T cell lymphoma may overexpress CD20 on their surface. Further, B and T cell lymphomas may be found in subjects including canine, felines, or humans. In certain embodiments, the ACT of the present disclosure may be used to treat lymphomas originating from any immune cell. In some embodiments, the ACT of the present disclosure may be used to treat B cell lymphomas. In other embodiments, the ACT of the present disclosure may be used to treat T cell lymphomas.

Osteosarcoma. Osteosarcoma is a cancer that may originate in the bone and may be classified into subtypes of high-grade, intermediate-grade, or low-grade depending on the stage of disease progression. Osteosarcoma may develop at bone junctions or sites of new bone development, where cancerous cells may produce bone matrix that lacks the mechanical integrity of healthy bone. Subjects affected by osteosarcoma may include canines, felines, or humans. Osteosarcoma may be found in youth among humans. In canines, nearly 85% of all bone tumors are a form of osteosarcoma. In certain embodiments, the ACT of the present disclosure may be used to treat osteosarcoma and may establish long term immunologic memory against osteosarcoma cancer cells.

Hemangiosarcoma. Hemangio sarcoma is a cancer of blood vessel cells most commonly reported in canines and, to a lesser extent, in felines. Hemangiosarcoma may be categorized into three subtypes defined by the location where the tumor develops and may include dermal hemangio sarcoma, hypodermal hemangio sarcoma, and visceral hemangio sarcoma. In certain embodiments, the ACT of the present disclosure may be used to treat hemangio sarcoma and may establish long term immunologic memory against hemangiosarcoma cancer cells.

Plasma Cell Tumors and Multiple Myeloma. Multiple myeloma is a condition in which multiple plasma cell tumors are identified in a subject. Plasma cells are mature B cells that produce immunoglobulin, but may become cancerous and may proliferate uncontrollably leading to cancer. Multiple myeloma may originate as a B cell cancer and may overexpress CD20. In certain embodiments, the ACT of the present disclosure may be used to treat plasma cell tumors and may establish long term immunologic memory against cancerous plasma cells. In further embodiments, the ACT of the present disclosure may be used to treat multiple myeloma and establish long term immunologic memory against cancer cells associated with multiple myeloma.

EXAMPLES

The following examples are included to further describe some aspects of the present disclosure, and should not be used to limit the scope of the embodiments described herein.

Example 1

Preparation of ABT-2+ Antigen Presenting Feeder Cells (aAPC)

This example describes preparation of the ABT-2+ antigen presenting feeder cells. The ABT-2+ cell line is a variant of the ABT-2 cell line, a chronic lymphocytic leukemia cell line, that has been transduced to express a set of cell surface markers and transfected to present an antigen. To produce the ABT-2+ cell line, ABT-2 was first transduced with lentiviruses comprising nucleotide sequences encoding human CD19, CD64, CD86, CD137L, and membrane bound human IL-15 to co-express human CD19, CD64, CD86, CD137L, and membrane bound human IL-15, and then cloned by limiting dilution. These cells were then co-cultured and transfected via electroporation with a nucleotide sequence encoding a recombinant canine CD20 (Engene, Inc.). ABT-2+ cells were grown in DME, supplemented with 10% FBS, L-glutamine and Sodium pyruvate (all obtained from Gibco/Life Technologies, Inc.). PNS (penicillin/neomycin/streptomycin) was added as an antibiotic to kill mycoplasmas, and prevent contamination (obtained from Sigma Corp). Cells were grown in a $CO_2$ incubator at 37° C., and 7.5% $CO_2$.

ABT-2+ cells were tested by PCR for the presence of the CD20 recombinant gene, and the absence of mycoplasma genes. Primer sequences employed were CD20 >>direction: TGC AGA CTC TTG GAA TTG GGT (SEQ ID NO: 4), CD20<<direction: AGC AGA GGT AAG CGA TCG TG (SEQ ID NO: 5), Myco>> direction: GTG GGG AGC AAA YAG GAT TAG A (SEQ ID NO: 6), and Myco<<direction: GGC ATG ATG ATT TGA CGT CRT (SEQ ID NO: 7). The cell line was positive for CD20 expression and negative for Mycoplasma.

The PCR profile that was employed is shown in Table 2.

TABLE 2

| PCR Parameters | | |
| --- | --- | --- |
| Degrees (C.) | Time (sec) | Cycles |
| 94 | 30 | 1 |
| 94 | 30 | |
| 56 | 90 | |
| 72 | 45 | 40 |

ABT-2+ cells were prepared for use in adoptive T cell studies by growth to exponential phase in DME/FBS, pelleted, and treated in one of two ways. In the first method, cells were inactivated by exposure to 57° C. for 25 minutes. Cells thus treated were determined to be >99% inactive, and suitable as targets. These cells were designated ABT-2+ HK (heat killed). In the second method, cells were inactivated by direct doses of gamma-radiation. A dose of 120 Gy was delivered by a cobalt cell irradiator to achieve a 99% inactive rate. These cells were designated ABT-2+ Gy. Human anti-CD3 antibody (OKT3, Muronmonab, Orthoclone, Raritan, N.J.), a general T lymphocyte stimulant, was then added to the inactivated cells from either method. Cells were frozen for storage in FBS/10% DMSO (Sigma) in liquid Nitrogen.

Example 2

Detection of B Cell Lymphoma in Patients and Cultures

This example describes the detection of B cell lymphomas in patients and cultures. Detection of lymphoma cells was performed by PCR using PCR primer sequences from Engene Labs, including LSA Blue 2, LSA Green 2, CB-1, and CB-2. Primers sequences employed were LSA Blue 2>> direction AGC CTG AGA GCC GAG GAC (SEQ ID NO: 8) and Green 2<< direction TGA GGA GAC GGT GAC CAG G (SEQ ID NO: 9), and were provided as a kind gift from North Carolina State University. Other primer sequences employed were CB-1>> direction CAG CCT GAG AGC CGA GGA CAC (SEQ ID NO: 10) and CB-2<< direction TGA GGA GAC GGT GAC CAG GGT (SEQ ID NO: 11), and were developed at Engene Labs.

The PCR profile that was employed is shown in Table 2.

Example 3

Preparation of Cells for Production of Antigen Specific Cells for Infusion

This example describes the production of antigen specific cells. The initial population of peripheral blood mononuclear cells (PBMCs) were collected from whole peripheral blood of the patient or donor, or concentrated from peripheral blood using an apheresis harvest. Apheresis techniques in canines were developed and optimized using the COBE Spectra and the Optia apheresis machines from TerumoBCT (Lakewood, Colo).

Preparation of cells from whole blood was performed by Ficoll gradient centrifugation to purify PBMCs from whole blood. This was done by collecting 20-40 ml of whole blood in lavender top tubes (EDTA), layering whole blood over Ficoll 1119 (Sigma Corp) which was diluted by the addition of 10 ml RPMI in 100 ml Ficoll, and then centrifuging these tubes at 2500 rpm for 25 min. FIG. 1 shows the cell layers that were obtained from this procedure. The upper layer of plasma was collected using a 10 ml pipette and discarded. Next, the PBMCs at the interface were collected into approximately 4 ml, diluted 1:10 in RPMI/FBS and centrifuged at 1500 rpm for 10 minutes. The resulting cell pellet was suspended in induction media.

Alternatively, PBMCs were also isolated from the fresh apheresis harvest. Three ml of cells were added to two 50 ml flasks with 15 ml of RPMI/FBS culture media that was diluted 1:10. Flasks were placed in the 37° C. incubator for 10 minutes after which the flasks were removed and agitated. Fibrin clots and platelets were removed with a pipette. This step was repeated 3-4 times until no more clumping occurred. The cells were then prepared for culture. Alternatively, the cryopreserved apheresis harvest along with a DMSO/plasma preservative was placed in a 50 ml centrifuge tube and centrifuged at 800 rpm for 5 minutes. The cell pellet was resuspended in 30 ml of induction media (RMP, IL-21, and phytohemaglutinin) and placed in the cell culture flasks.

This resulting population of PBMCs from any of these methods was a mixture of all phenotypes of lymphocytes and monocytes, of which a variable number were CD8+ T cells with naturally occurring T cell receptors.

Preparation of cells from apheresis harvest was performed as follows. Approximately 3 ml of harvest at 60,000 cells/ml were used. The harvest was directly added to 2×50 ml flasks, which contained 15 ml RPMI/FBS. Flasks were placed in the 37° C. incubator for 10 minutes and then removed and agitated. Fibrin/platelet clots appeared and precipitated into clumps as shown in FIG. 2. This step was repeated about 3-4 times for each flask, until no further clotting appears. Clumps were removed with a pipette, any additional reagents were added to the remaining cells, and the flasks were incubated normally.

Figure 11:
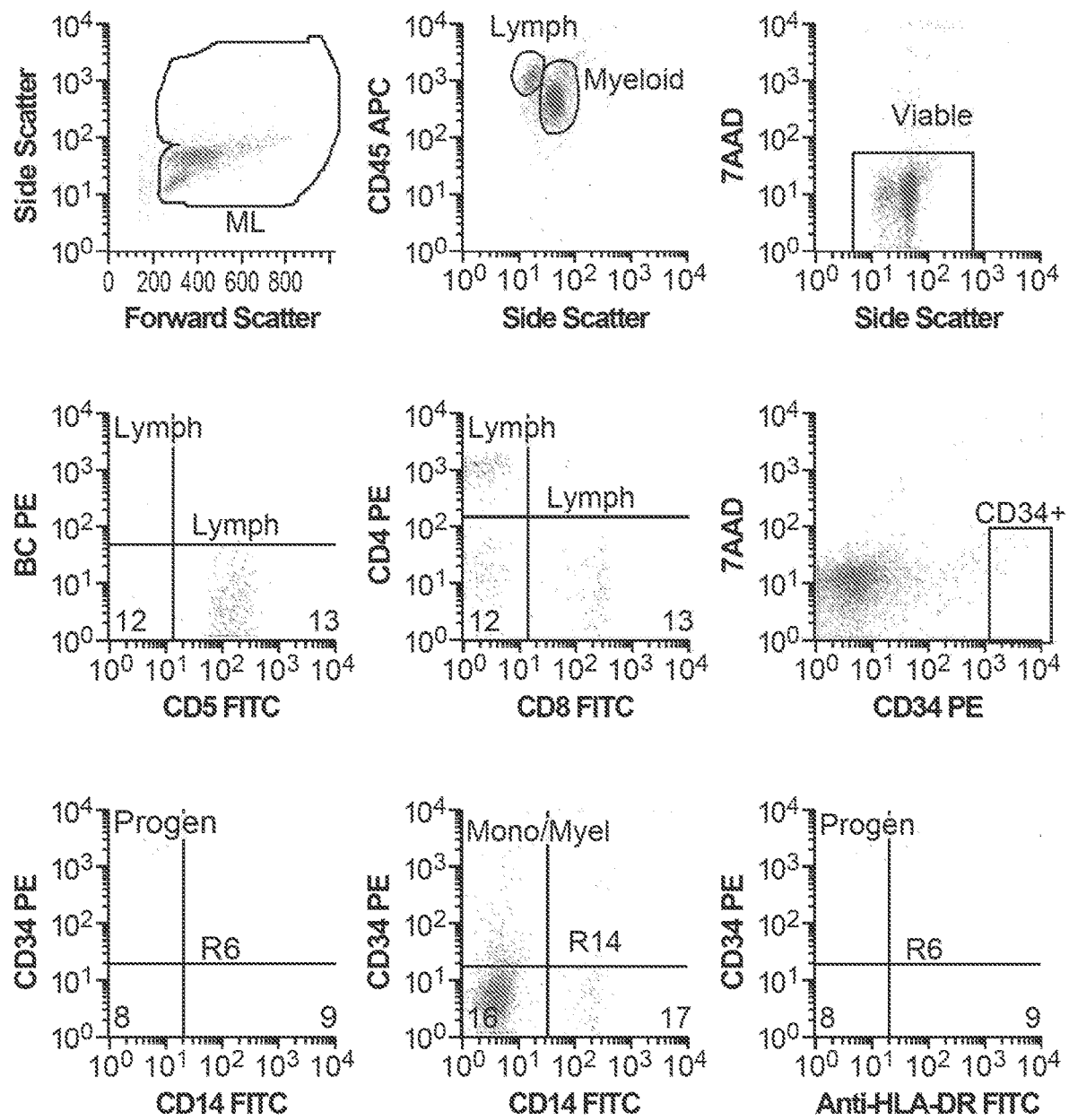
FIG. 11 shows flow cytometry dot plots of cell populations from the peripheral blood of patient GS.

FIG. 11 shows cell populations from the peripheral blood of patient GS. Patient GS had a clinical history of B cell lymphoma. Patient GS was administered standard CHOP therapy may 2014-January 2015 and relapsed in 03/2015. GS was administered another round of CHOP therapy followed by rescue chemotherapy until the patient's first infusion. Flow cytometry was used to assess cell populations in peripheral blood three months after her last chemotherapy. Flow cytometry was used to determine that the peripheral blood included 9.5% lymphocytes, 88% myeloid/monocyte cells, and 0.3% progenitor cells including some monocytes. Viability was determined to be 93%. Independent immunophenotypic analysis revealed lymphocytes consisting exclusively of T cells with a normal CD4:CD8 ratio of 53:13. B lymphoid cells were not identified.

Figure 12:
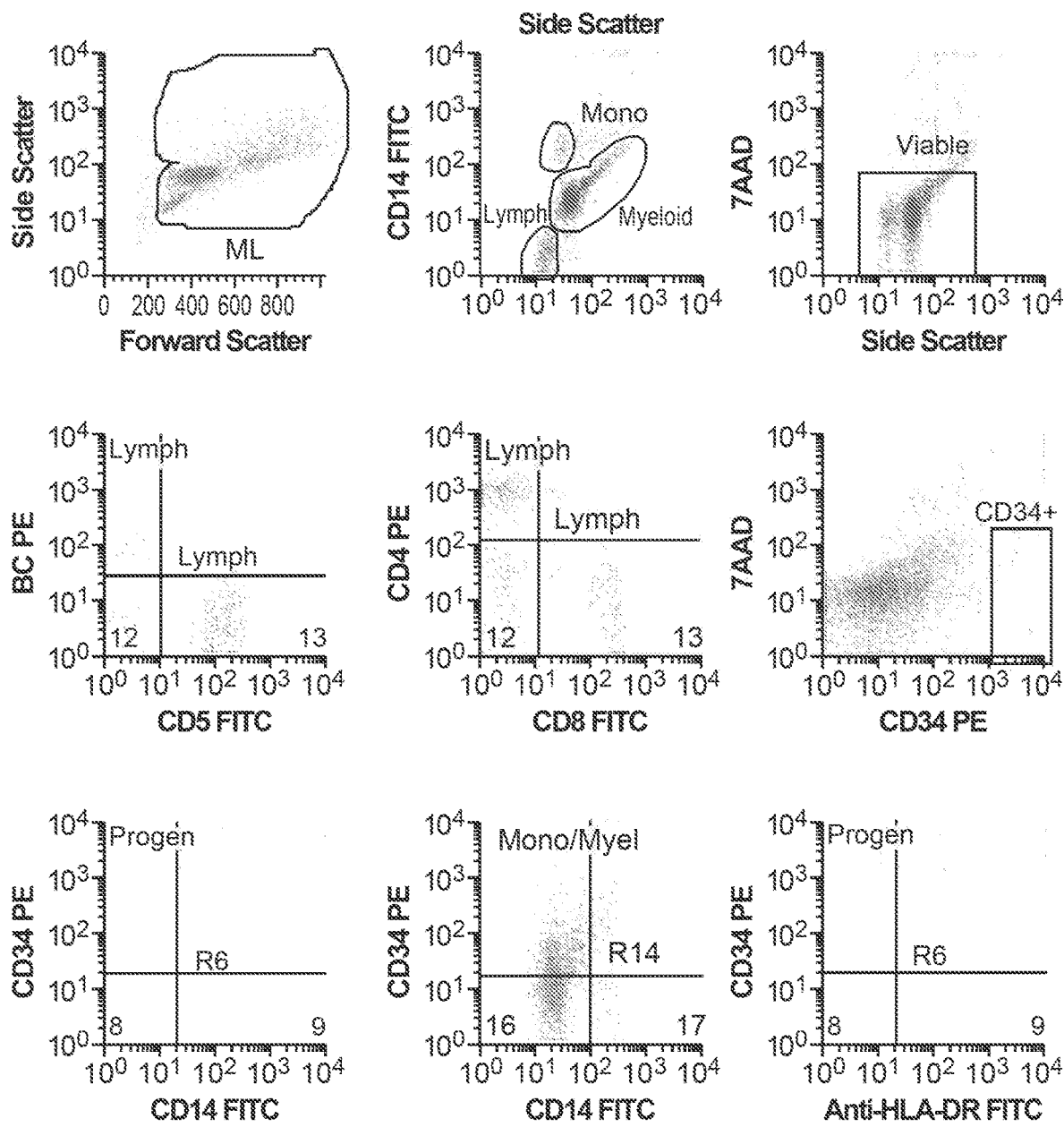
FIG. 12 shows flow cytometry dot plots of cell populations from the buffy coat after apheresis harvest from patient GS.

FIG. 12 shows cell populations from the buffy coat after apheresis harvest and centrifugation of whole blood from patient GS. Flow cytometry was used to assess cell populations in buffy coat three months after her last chemotherapy. Flow cytometry was used to determine that the buffy coat included 9.6% lymphocytes, 85% myeloid/monocytes, and 0.2% progenitor cells including some monocytes. Viability was determined to be 93%. Independent immunophenotypic analysis revealed lymphocytes consisting of 4.3% B cells, 88% T cells, and 7.0% NK cells. The CD4:CD8 ratio (58:19) was normal.

Figure 15:
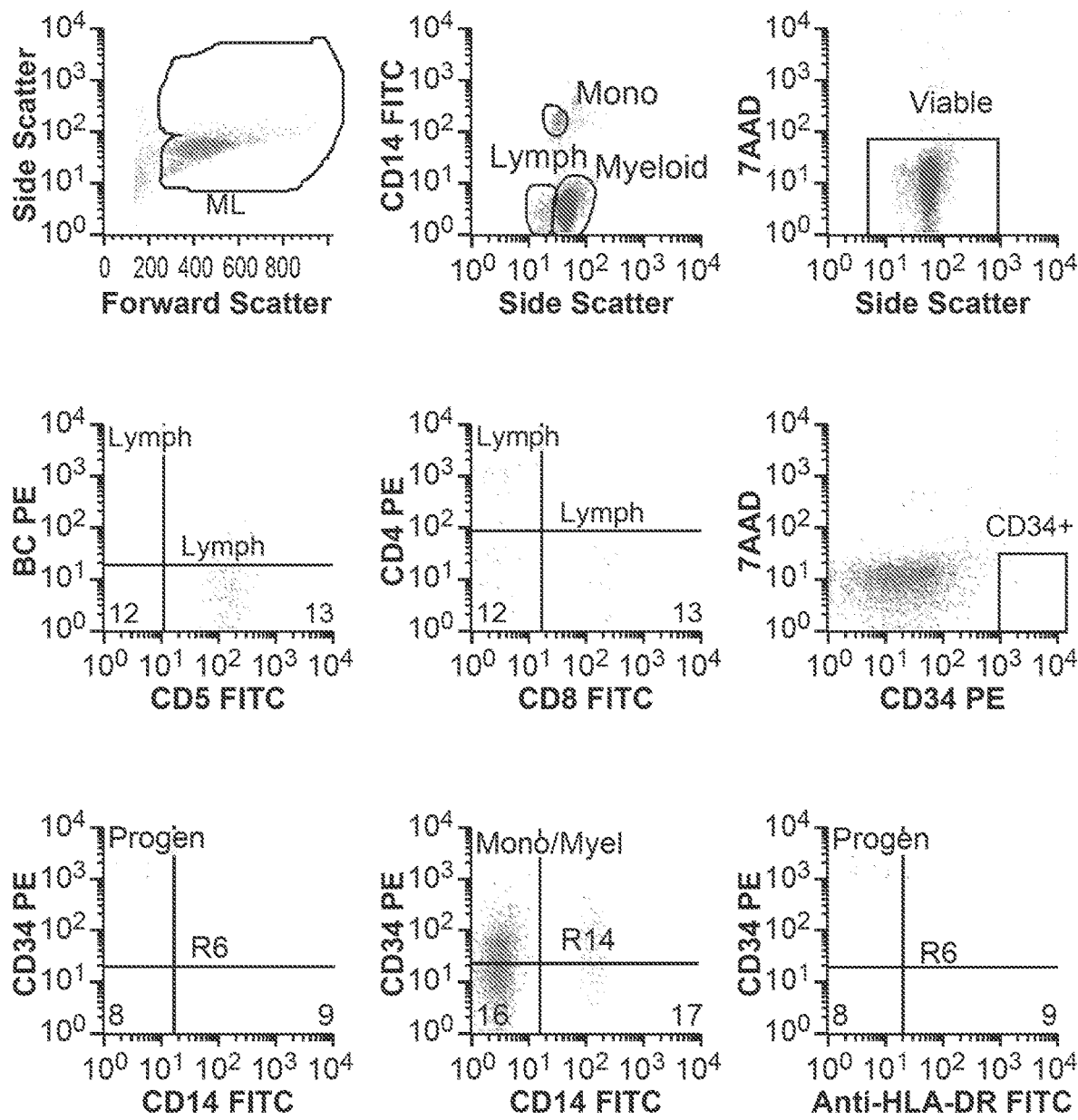
FIG. 15 shows flow cytometry dot plots of cell populations from the peripheral blood of patient CL.

FIG. 15 shows cell populations from peripheral blood of patient CL. Patient CL had a clinical history of B cell lymphoma. Flow cytometry was used to determine that the peripheral blood included 2.6% lymphocytes, 94% myeloid/monocytes, and 0.1% progenitor cells this including some monocytes. Viability was determined to be 94%. Independent immunophenotypic analysis revealed lymphocytes consisting exclusively of T cells. The CD4:CD8 ratio (46:19) was normal and B lymphoid cells were not identified.

Figure 16:
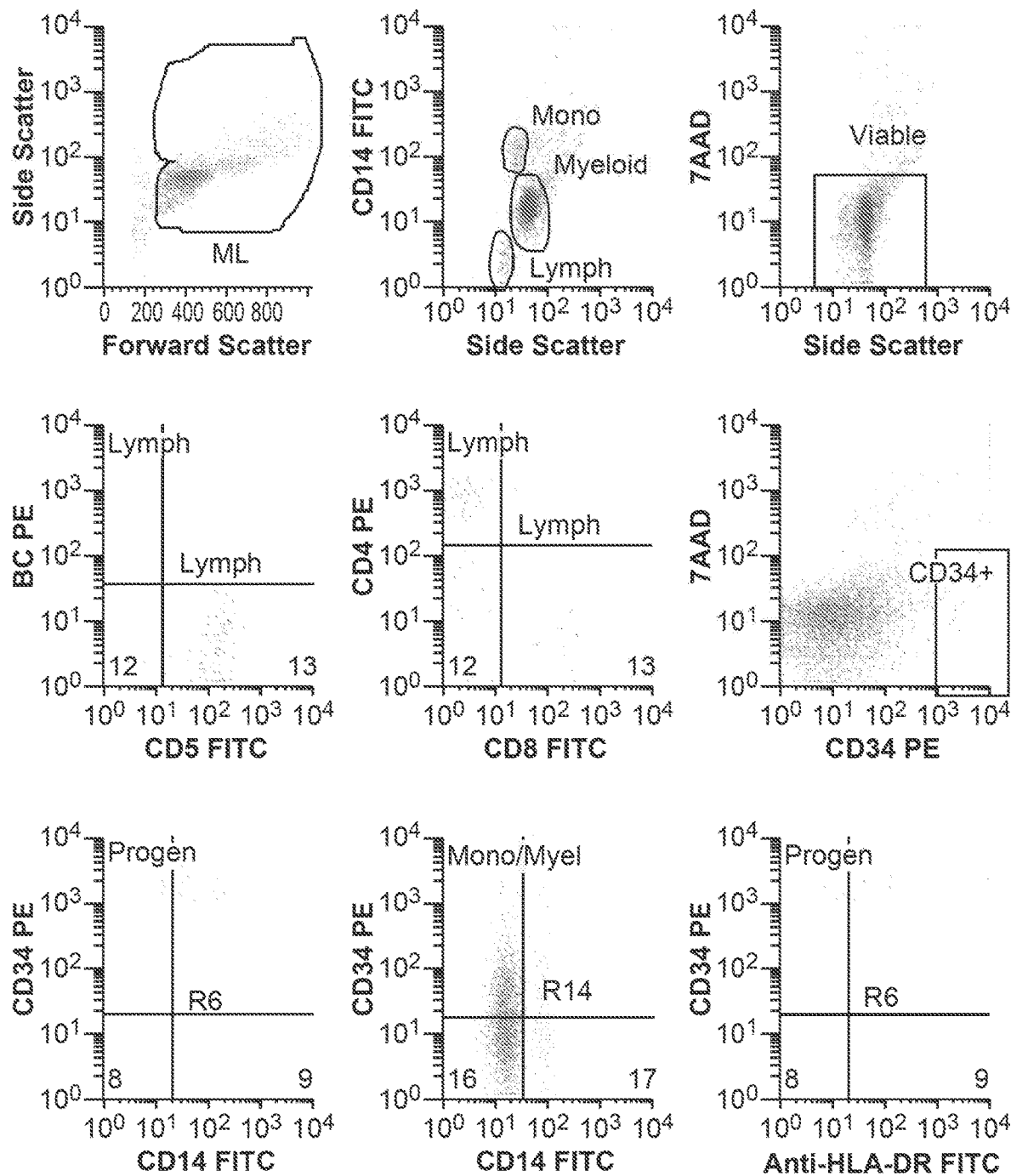
FIG. 16 shows flow cytometry dot plots of cell populations from the buffy coat after apheresis harvest from patient CL.

FIG. 16 shows cell population from the buffy coat after apheresis harvest and centrifugation of whole blood from patient CL. Flow cytometry was used to determine that the buffy coat included 3.2% lymphocytes, 92% myeloid/monocytes, and 0.4% progenitor cells including some monocytes. Viability was determined to be 91%. Independent immunophenotypic analysis revealed lymphocytes consisting exclusively of T cells. The CD4:CD8 ratio (65:12) was normal and B lymphoid cells were not identified. These measurements were done after patient CL underwent conditioning as described in Table 3.

Cryopreserved apheresis harvest was treated differently. The entire harvest consisted of approximately 20 ml of cells in a DMSO/autologous plasma preservative. The harvest was placed in a 50 ml centrifuge tube and spun gently at 800 rpm for 5 minutes. The cell pellet was re-suspended in 30 ml of induction media and placed in 50 ml flasks and 24 well plates as required.

To select, expand, and stimulate the CD8+ T lymphocytes that have anti-B cell lymphoma properties, isolated PBMCs were co-cultured with an interleukin mixture and irradiated, cryopreserved, antigen presenting feeder cell line (aAPC)— ABT-2+ Gy cells, which were produced as described in EXAMPLE 1.

The isolated PBMCs were cultured in the 37° C. incubator at 5% $CO_2$ and at 96% humidity in RPMI culture media at a 2:1 ratio of PBMCs to irradiated, cryopreserved ABT-2+ (ABT-2+ Gy) cells. The culture was re-stimulated every 7-10 days with additional ABT2+ Gy cells. Recombinant human IL-21 was added three times for the first week, in order to preferentially stimulate propagation of CD8+ T cells. Recombinant human IL-21 and recombinant human IL-2 were added at 100 U/ml three times per week for subsequent weekly stimulations, beginning with the first re-addition of ABT-2+ Gy cells.

The cells were checked for contamination with mycoplasma via PCR and then aliquoted for infusion, continued in expansion, or cryopreserved in freeze media for future use. Freeze media was made with 10% DMSO in autologous plasma. The resulting cell population was evaluated via flow cytometry to confirm a predominant CD8+ T cell phenotype of expanded PBMCs.

Viable T cells were enumerated every 7 days by Trypan blue exclusion. The resulting cell culture was expanded through repeated transfers to culture flasks, and when a sufficient number of T cells were produced, they were purified until no more ABT-2+ Gy cells were evident.

PBMCs established in the culture with ABT-2+ Gy cells and the interleukin mixture passed through several major phases. First, a period of generalized cell death was observed as cells which were unresponsive to IL-21 and had no reactivity to antigens presented on the ABT-2+ Gy cell surface died. Unresponsive cells constituted approximately 95% of the cells isolated in the Ficoll gradient step. FIG. 3 shows the result of this process, which was a cell nadir that reached a maximum extent at Day +7 after culture initiation.

Next, the influence of IL-21 on T cells reacting to CD20 on the ABT-2+ Gy+ cell surface lead to the expansion of T cells, as shown by their physical association with ABT-2+ cells in culture. These CD8+ T cells were elongated as they were activated and divided. As T cells found and interacted with ABT-2+ Gy cells, they were bound in clusters in an end-on manner. FIG. 4 shows an example of this phenomenon, which started around Day +7 in culture and continued for a week or more. FIG. 5 shows an example of this phenomenon on Day +11 where T cells were bound to ABT-2+ Gy cells in clusters.

FIG. 17 shows a tissue culture 8 days after growth. Flow cytometry was used to determine that the cell population was composed of 1.5% lymphocytes and 46% monocytes. The rest were non-viable cells and cell debris. The lymphocytes consisted exclusively of T cells that express CDS, CD8 and CD4. The CD4:CD8 ratio (35:47) was reversed and the viability was determined to be 5%.

FIG. 18 shows a tissue culture different from that of FIG. 17 8 days after growth. Flow cytometry was used to determine that the cell population as composed of 1.6% lymphocytes and 42% monocytes. The remainder consisted of non-viable cells and cellular debris. Lymphocytes consisted exclusively of T cells that expressed CDS, CD8 and CD4. The CD4:CD8 ratio (20:61) was reversed and viability was determined to be 15%.

In the third stage, the overall numbers of IL-21 reactive, CD20 responsive CD8+ T cells greatly expanded. As shown in FIG. 6 on Day +14 and in FIG. 7 on DAY +16, at this point, generally all surviving ABT-2+ cells had attached T cells.

FIG. 8 shows that as T cells expanded clonally from their initial points, by Day +12, there was a distinct directionality to their physical expansion highlighted by the end-to-end orientation of T cells.

In the final stage, expansion of T cells reached an exponential phase. During this phase, IL-21 addition was ceased and cells were expanded on IL-2 and PHA only. No further ABT-2+ Gy cells were added. As shown in FIG. 9, T cells covered the available surface of the flask or well in a confluent layer by Day +21. The expanded cells were collected at this stage around Day +21.

FIG. 14 shows cell culture 21 days after growth. As determined by flow cytometry, the population of cells was 100% lymphocytic. The lymphocytes consisted exclusively of T cells that expressed CD5, CD8 and CD4. The CD4:CD8 ratio (18:33) was reversed and viability was at 13%.

Example 4

Preparation of Media Used to Produce Antigen Specific Cells

This example describes the preparation of media used to produce antigen specific cells. Two basic media preparations were used. Dulbecco's Modified Eagle's Media (DMEM) (Gibco) supplemented with 10% FBS (Gibco) L-glutamine, PNS antibiotics (penicillin, neomycin and streptomycin) (Gibco), and sodium pyruvate was used to grow the cell line ABT-2+. This media is strongly buffered and useful for robust, established cell lines which rapidly grow. Roswell Park Memorial Institute #1640 (RPMI), was used for propagating peripheral blood mononuclear cells (PBMCs). This media was less buffered, and therefore less toxic to cells unaccustomed to culture. It was also supplemented with 10% FBS (Gibco, or Sigma Titer-Max), L-glut, and PNS antibiotics. After preparation, contamination batch tests were placed in the incubator to verify sterility.

Induction media (IM) was used from days 0-7 of incubation of PBMC cultures. This media consisted of RPMI with Interleukin 21 (IL-21) (Gibco/Life) and Phytohemagglutinin (PHA) (Sigma Corp.). 30 µL of IL-21 was diluted to 100 µg/ml in sterile water, and 60 µL PHA (100 µg/ml in saline) was added to 30 ml RPMI/FBS. 20 µl of whole blood from the patient was added to serve as a feeder layer if necessary. $2 \times 10^7$ of ABT-2+ Gy/cryo cells were added to the preparation just prior to use. These cells were cryopreserved and were washed once in RPMI (gently spun at 800 rpm).

Propagation media (PM) was employed from day 7-21 incubation. This media consisted of 30 ml RPMI with 20 µL interleukin 2 (IL-2) diluted to 100 µg/ml in 100 mM acetic acid (Gibco/Life) added. Interleukin 21 (IL-21) and PHA were added as before. 10-20 µL of whole blood specific to the patient were added if required as a feeder layer. Freshly thawed $1 \times 10^7$ ABT-2+ Gy/cryo targets cells were also added.

Expansion media (EM) was used as the last feeding media prior to harvesting the cells for infusion. This media consisted of 30 ml RPMI (as above) with 30 µl IL-2 preparation and 60 µl PHA added. No IL-21 was used in this media preparation. No feeder cells or ABT-2+ were required for this media.

Example 5

Patient Conditioning Regimens Prior to Antigen Specific Cell Infusions

This example describes the patient conditioning regimens patients undergo prior to antigen specific cell infusions. Several variations of patient conditioning prior to antigen specific cell infusions were tested. Standard induction chemotherapy was used for most patients using the CHOP (cyclophosphamide, doxorubicin, vincristine, and prednisone) protocol, followed by a dose of cyclophosphamide (250 mg/m$^2$) 12-18 days before the first antigen specific cell infusion. It is postulated that the cyclophosphamide may be both cytoreductive to the tumor population as well as to the CD4+ regulatory T cells that inhibit an anti-tumor immune response by the adoptive T cells.

In two patients, an autologous bone marrow transplant was completed prior to infusion of the antigen specific cells. This conditioning served to provide a clean immunologic environment to the antigen specific cells, and therefore allowed a robust anti-tumor response.

Alternatively, one patient was conditioned with a truncated induction chemotherapy protocol that included one dose of L-Asparginase, one dose of vincristine, and one dose of cyclophosphamide prior to the adoptive T cell infusions. It was speculated that treatment in the early stage of disease will result in a more robust immune response as the immune system will not be fatigued by many weeks or months of chemotherapy. This patient continues to be in MR and is disease free as of the date of filing.

A summary of patients is shown in Table 3. Briefly, 25 B cell lymphoma patients and 1 osteosarcoma patient were treated with autologous activated T cells. Patients ranged in age from 3-11 years, with 9 years being the most common. The male to female ratio was 16:10 and the weight of patients ranged from 4.5 kg to 45 kg. In the lymphoma cases, the stage of lymphoma ranged from 4a-5b based on the WHO classification. 20/25 lymphoma patients were purebred canines and 5/25 lymphoma patients were mixed-breed canines. One osteosarcoma patient was a purebred canine. Twenty of twenty-six patients had standard CHOP therapy. Of the 25 lymphoma patients, 24 patients had B cell lymphoma and 1 patient had mixed T cell and B cell lymphoma.

Of the twenty-six subjects, fifteen subjects are currently in remission and are under monthly evaluation.

A total of seven dogs, identified here by their initials, were involved in an initial study. Four subjects (GS, CL, VS, EL) were B cell lymphomas that were out of remission (OOR). One subject (WS) was an osteosarcoma in the primary stage. One subject (RM) was initially a B cell lymphoma, converted to a T cell lymphoma, and was in a blast crisis. The final subject (MW) was a bone marrow transplant (BMT) B cell lymphoma case in complete remission (CR)/molecular remission (MR), in which cryopreserved harvest was used. An additional 5 patients were treated, in various stages of disease progression, some in CR at the time of antigen specific cell infusion, some immediately after an autologous bone marrow transplant, and one with minimal pre-treatment with chemotherapy.

Antigen specific cell infusion was also provided to one subject with a malignancy other than B cell lymphoma. One subject, patient WS, had appendicular osteosarcoma. Antigen specific cells are selected in the presence of tumor antigens, pressed towards a predominantly CD8+ phenotype, then expanded and stimulated prior to infusion.

Example 6

T Cell Infusion in Patients and Suppression of Active Disease

This example describes T cell infusion in patients and suppression of active disease. The propagated T cells were infused in patients via a peripheral vein catheter at an initial rate of $5 \times 10^8$ cells/m². The second and third doses of cells were escalated to $5 \times 10^9$ cells/m² and were given two weeks after and four weeks after the initial dose. This dosing schedule resulted in rapid response, identified as an improvement of clinical signs and a measureable decrease in the clonal B cell population based on PCR and flow cytometry, and minimal toxicity. The infused T cells, since they were an expansion of naturally occurring T cells with innate T cell receptors (TCRs) reproduced, recruited additional immune system cells, and induced memory T cell response. All patients treated, with the exception of patients GS, WS, CK, SH, MC, MW, BF, RK, and DT are in either CR or MR. Of the 26 patients shown in Table 4, five maintained MR, two maintained CR, seven went from CR to MR, one went from OOR to CR, and one went from MR to stable CR. Patient MW maintained OOR, but had a complication due to a blood born infection from a transfusion. Patient CK also maintained OOR, but went off protocol and received treatment elsewhere.

Subjects with B cell lymphomas were treated with standard multi-agent chemotherapy, then were consolidated with high dose cyclophosphamide chemotherapy (250 mg/m²-650 mg/m²) and/or total body irradiation (2-12 Gy), and rescued with either autologous or allogeneic (matching canine leukocyte antigen identical donor) CD34+ cells at $0.5$-$10 \times 10^6$ cells per kg. During the white blood cell recovery, 2-4 doses of adoptive T cells were infused that resulted in long term immunologic control of the B cell lymphoma. The addition of consolidation therapy reduced the number of regulatory immune cells in the patient.

Table 3 shows a summary of all patients that were enrolled in the current study (breed, age, sex, weight, disease, stage, date of diagnosis, induction therapy, rescue therapy, relapse, and remission status at the time of adoptive T cell therapy (ACT)).

TABLE 3

Patient Summary

| Patient | Breed | Age (Years) | Sex | Weight (kg) | Disease | Stage | Date of Diagnosis | Induction Therapy | Rescue Therapy | Relapse | Remission Status at time of ACT |
|---|---|---|---|---|---|---|---|---|---|---|---|
| GS | Golden Ret | 11 | Fs | 32.5 | B | 5b | 2014 | Chop | Chop | 3 | OOR |
| WS | Labradoodle | 11 | Mn | 43.6 | OS | NA | Feb. 28, 2016 | NA | NA | NA | OOR |
| CL | Mix | | Mn | 45.5 | B | 5b | 2015 | Chop | BMT | 3 | OOR |
| VS | Corgi | 9 | Mn | 13.2 | B | 5a | 2015 | Adriax5 | L-Asparaginase | 2 | OOR |
| MW | French Bulldog | 6 | Fs | 9.8 | B/T | 5a | 2015 | Chop | BMT | 2 | OOR |
| CM | Doberman | | Fs | 30 | B | 5b | 2015 | Chop | Chop | 2 | OOR |
| MM | Cocker | | Fs | 16 | B | 4a | 2015 | Chop | BMT | 0 | MR |
| BG | Golden Ret | | Mn | 34 | B | | 2015 | Chop | Cytox | 2 | MR |
| CK | Pointer | 8 | Mn | 28.6 | B | 5a | 2015 | Chop | Cytox | 2 | OOR |
| TC | Corgi | 7 | Mn | 12.3 | B | 4a | 2015 | Chop | Cytox | 1 | MR |
| MM | Pointer | | Mn | 18.1 | B | 4a | 2015 | Chop | BMT | 1 | MR |
| BT | Golden Ret | 9 | Mn | 33.8 | B | 5a | Jun. 3, 2016 | EV | Cytox | 1 | OOR |
| BF | Yorkie | | Mn | 4.5 | B | 4a | 2015 | Chop | Cytox | 1 | MR |
| SH | Havanese Mix | 11 | Fs | 6.7 | B | 5b | 2015 | Chop | Cytox | 2 | CR |
| RK | Pit Bull | 3 | Fs | 27.1 | B | 5a | 2015 | | Astatine BMT | 2 | OOR |
| NF | Corgi | 8 | Fs | 14 | B | 5b | May 1, 2016 | CHOP | BMT | 0 | MR |
| MC | Golden doodle | 9 | Fs | 23.6 | B | 5a | NA | CHOP | CCNU | 1 | OOR |
| DT | Cocker | 5 | Fs | 11.4 | B | 5b | Dec. 15, 2016 | CHOP | None | 2 | OOR |
| DP | Cocker | 7 | Mn | 12.7 | B | 5b | January 2016 | BMT | None | 0 | MR |
| CM | Chow Mix | 6 | Fs | 25 | B | 5b | October 2016 | CHOP | BMT | 2 | MR |
| BE | Cocker | 8 | Mn | 12.7 | B | 5a | October 2016 | CHOP | CCNU | 2 | CR |
| BPS | Golden Lab Mix | 6 | Mn | 21.8 | B | 5b | November 2016 | BMT | None | 0 | CR |
| BI | Poodle | 9 | Mn | 21.6 | B | 5a | Dec. 15, 2014 | CHOP | Tanovea | 2 | OOR |

TABLE 3-continued

Patient Summary

| Patient | Breed | Age (Years) | Sex | Weight (kg) | Disease | Stage | Date of Diagnosis | Induction Therapy | Rescue Therapy | Relapse | Remission Status at time of ACT |
|---|---|---|---|---|---|---|---|---|---|---|---|
| FW | Beagle | 7 | Mn | 16.8 | B | 5a | November 2016 | CHOP | None | 0 | MR |
| BA | Blue Heeler | 9 | Mn | 27.7 | B | 5b | NA | CHOP | None | 0 | CR |
| CA | Labrador | 7 | Mn | 31.8 | B | 5b | NA | BMT | None | 0 | MR |

Fs: Female spayed
Mn: Male neutered
OS: Osteosarcoma
B: B cell lymphoma
B/T: Combined B cell/T cell lymphoma
Chop: CHOP standard protocol of cyclophosphamide, doxorubicin, vincristine, and prednisone
EV: Combination of Elspar and vincristine
BMT: Autologous bone marrow transplant
OOR: Out of remission
CR: Clinical remission
MR: Molecular remission Table 4 shows a summary of all patients that were enrolled in the current study, total cells infused per kg, date of first infusion, current remission status, and general notes.

TABLE 4

Summary of Infusions and Current Patient Status

| Patient | Total Cells Per kg | Date of First Infusion | Current Remission Status | Notes |
|---|---|---|---|---|
| GS | 2.22E+06 | Mar. 25, 2016 | OOR | Disease progression and death. |
| WS | 1.48E+06 | Mar. 30, 2016 | CR | Disease progression and death five months post infusion. |
| CL | 1.50E+06 | Apr. 18, 2016 | MR | Doing well. |
| VS | 9.00E+06 | May 15, 2016 | CR | Disease progression and death five months post infusion. |
| MW | 1.51E+06 | May 23, 2016 | CR | Disease progression and death. |
| CM | 1.55E+06 | May 23, 2016 | MR | Doing well. |
| MM | 1.16E+06 | Jun. 6, 2016 | MR | Doing well. |
| BG | 7.35E+05 | Jun. 6, 2016 | MR | Relapsed, repeat chemo and infusion is scheduled. |
| CK | 3.21E+05 | Jun. 13, 2016 | OOR | Disease progression and death four months post infusion. |
| TC | 1.55E+05 | Jun. 20, 2016 | MR | Doing well. |
| MM | 2.29E+06 | Jun. 20, 2016 | MR | Doing well. |
| BT | 1.09E+06 | Jun. 23, 2016 | CR | Doing well. Conditioned with minimal induction chemotherapy of three doses - Elspar, Vincristine, Cyclophosphamide |
| BF | 4.31E+06 | Jun. 27, 2016 | CR | Disease progression and death. |
| SH | 3.48E+06 | Jun. 30, 2016 | OOR | Relapsed. Second set of infusions were given. Continues to have stable disease. |
| RK | 4.93E+05 | Jul. 1, 2016 | CR | Disease progression and death. |
| NF | 9.86E+05 | Jan. 19, 2017 | CR | Disease progression and death. |
| MC | 5.33E+06 | Mar. 9, 2017 | OOR | Disease progression and death three months post infusion. |
| DT | 4.75E+06 | 002/07/2017 | OOR | Disease progression and death 1 month post infusion |
| DP | 1.18E+06 | Feb. 7, 2017 | CR, MR | Doing well |
| CM | 1.65E+07 | Mar. 16, 2017 | CR | Doing well |
| BE | 1.25E+07 | Mar. 15, 2017 | CR | Doing well, stable disease. |
| BPS | 7.80E+06 | Mar. 7, 2017 | CR, MR | Doing well |
| BI | 5.22E+06 | Mar. 9, 2017 | CR | Died (chemotherapy induced cardiomyopathy). |
| FW | 2.88E+06 | Apr. 19, 2017 | CR, MR | Doing well |
| CA | 3.35E+06 | Apr. 19, 2017 | CR, MR | Doing well |
| BA | 2.26E+06 | May 11, 2017 | CR, MR | Doing well |

OOR: Out of remission
CR: Clinical remission
MR: Molecular remission

Table 5 shows the differential of white blood cell types in cells infused into each patient, including the number of white blood cells infused, and the numbers and percentages of neutrophils, lymphocytes, eosinophils, and basophils infused. The number after the patient indicates the infusion number.

TABLE 5

Summary of Infused Cell Composition

| Patient | WBC 10^3/uL | NEUT | LYM | MONO | EOS | BASO | NEUT % | LYM % | EOS % | MONO % | BASO % |
|---|---|---|---|---|---|---|---|---|---|---|---|
| BT 1 | 0.65 | 0.24 | 0.32 | 0.09 | 0 | 0 | 35.8 | 48.3 | 0.6 | 15.2 | 0.1 |
| CK 1 | 0.69 | 0.23 | 0.31 | 0.13 | 0.02 | 0 | 32.0 | 44.5 | 3.4 | 19.8 | 0.0 |
| CK 2 | 0.80 | 0.27 | 0.36 | 0.16 | 0.01 | 0 | 32.6 | 44.9 | 2.1 | 20.4 | 0.0 |
| CL 2 | 1.30 | 0.39 | 0.47 | 0.40 | 0.01 | 0.03 | 29.6 | 36.0 | 1.1 | 30.3 | 3.0 |
| BG 1 | 1.14 | 0.43 | 0.25 | 0.25 | 0.20 | 0.01 | 37.7 | 21.7 | 18.1 | 21.3 | 1.2 |
| CL 2 | 1.63 | 0.29 | 1.19 | 0.14 | 0.01 | 0 | 17.7 | 73.0 | 0.6 | 8.4 | 0.3 |
| BG 2 | 1.36 | 0.32 | 0.5 | 0.41 | 0.11 | 0.02 | 23.6 | 36.2 | 8.4 | 30.4 | 1.4 |
| WS 3 | 1.87 | 0.68 | 0.55 | 0.46 | 0.14 | 0.02 | 36.0 | 29.3 | 7.6 | 25.7 | 1.4 |
| WS 2 | 2.12 | 0.36 | 1.08 | 0.63 | 0.02 | 0.03 | 16.9 | 50.9 | 1.1 | 29.3 | 1.8 |
| MMO 1 | 0.78 | 0.25 | 0.26 | 0.21 | 0.05 | 0.01 | 31.3 | 33.1 | 7.6 | 26.7 | 1.3 |
| TYC 1 | 0.62 | | | | | | | | | | |
| RK 1 | 1.38 | 0.68 | 0.30 | 0.29 | 0.09 | 0.02 | 48.7 | 21.7 | 6.7 | 21.4 | 1.5 |
| CM 2 | 1.66 | 0.51 | 0.73 | 0.32 | 0.09 | 0.01 | 30.2 | 43.5 | 5.5 | 19.8 | 1.0 |
| WS 1 | 2.44 | 0.52 | 1.41 | 0.39 | 0.10 | 0.02 | 21.1 | 57.5 | 4.4 | 16.1 | 0.9 |
| WS 4 | 2.66 | 0.94 | 1.32 | 0.26 | 0.13 | 0.01 | 25.2 | 49.4 | 4.9 | 10.1 | 0.4 |
| VS 2 | 0.86 | 0.28 | 0.38 | 0.18 | 0.01 | 0.01 | 31.8 | 43.1 | 1.8 | 21.2 | 2.1 |
| MMO 2 | 1.08 | 0.35 | 0.46 | 0.20 | 0.06 | 0.01 | 31.8 | 41.9 | 6.1 | 19.2 | 1.0 |
| MMA 1 | 1.46 | | | | | | | | | | |
| GS | 2.73 | 0.54 | 1.19 | 0.97 | 0.02 | 0.01 | 19.8 | 43.4 | 0.9 | 35.3 | 0.6 |
| CL 1 | 1.45 | 0.47 | 0.59 | 0.32 | 0.04 | 0.03 | 32.1 | 40.4 | 3.1 | 22.0 | 2.4 |
| BT | 3.04 | 0.82 | 1.07 | 0.96 | 0.15 | 0.04 | 26.9 | 35.2 | 5.0 | 31.4 | 0.0 |
| CM 1 | 3.00 | 1.04 | 0.92 | 0.74 | 0.22 | 0.08 | 34.4 | 30.6 | 7.4 | 24.8 | 2.8 |
| TYC 2 | 1.29 | 0.37 | 0.54 | 0.34 | 0.04 | 0 | 28.5 | 41.6 | 3.4 | 26.1 | 0.0 |
| GS | 4.45 | 1.94 | 1.52 | 0.85 | 0.16 | 0.07 | 42.6 | 33.4 | 3.6 | 18.8 | 1.6 |
| MMA 2 | 2.67 | 0.82 | 1.32 | 0.38 | 0.10 | 0.03 | 30.5 | 50.3 | 4.0 | 14.0 | 0.0 |
| MW 1 | 1.51 | 0.34 | 0.61 | 0.49 | 0.06 | 0.01 | 22.8 | 40.0 | 4.2 | 32.2 | 0.8 |
| CK 3 | 4.64 | 1.32 | 1.12 | 1.70 | 0.46 | 0.01 | 28.3 | 24.5 | 9.8 | 37.1 | 0.3 |
| RK 2 | 5.03 | 2.46 | 1.65 | 0.69 | 0.19 | 0.04 | 48.8 | 32.8 | 3.9 | 13.6 | 0.9 |
| BF 2 | 0.89 | 0.44 | 0.31 | 0.11 | 0.03 | 0 | 48.4 | 34.5 | 3.5 | 12.9 | 0.7 |
| VS 1 | 3.27 | 0.92 | 1.55 | 0.69 | 0.09 | 0.02 | 28.0 | 47.4 | 2.7 | 21.3 | 0.6 |
| SH 2 | 2.11 | 0.82 | 0.8 | 0.41 | 0.06 | 0.02 | 38.9 | 37.9 | 3.1 | 19.2 | 0.9 |
| SH 1 | 2.37 | 0.98 | 0.69 | 0.56 | 0.13 | 0.01 | 41.1 | 29.1 | 5.7 | 23.5 | 0.6 |
| SK 1 | 2.76 | 0.77 | 1.54 | 0.19 | 0.25 | 0.01 | 27.8 | 55.5 | 9.2 | 7.0 | 0.5 |
| BF 1 | 2.40 | 1.64 | 0.41 | 0.28 | 0.07 | 0 | 68.0 | 17.0 | 3.1 | 11.9 | 0.0 |
| NF1 | 34.26 | 9.47 | 8.58 | 15.45 | 0.52 | 0.24 | 27.7 | 25.0 | 1.5 | 45.1 | 0.7 |
| NF2 | 0.95 | 0.38 | 0.45 | 0.10 | 0.02 | 0.00 | 39.1 | 46.7 | 11.3 | 2.6 | 0.3 |
| NF3 | 4.89 | 1.70 | 2.31 | 0.75 | 0.12 | 0.01 | 34.8 | 47.2 | 15.3 | 2.4 | 0.3 |
| NF4 | 6.68 | 1.68 | 2.32 | 2.47 | 0.18 | 0.03 | 25.2 | 34.6 | 37.0 | 2.7 | 0.5 |
| NF5 | 3.55 | 2.47 | 0.60 | 0.31 | 0.15 | 0.02 | 69.4 | 16.9 | 8.8 | 4.2 | 0.7 |
| NF6 | 0.92 | 0.54 | 0.27 | 0.08 | 0.03 | 0.00 | 58.7 | 28.7 | 8.7 | 3.5 | 0.4 |
| CA1 | 0.71 | 0.25 | 0.38 | 0.05 | 0.03 | 0.00 | 34.3 | 53.0 | 6.7 | 5.2 | 0.8 |
| CA2 | 1.47 | 0.54 | 0.58 | 0.25 | 0.09 | 0.01 | 36.6 | 38.9 | 17.0 | 6.3 | 1.2 |
| BA1 | 10.33 | 3.54 | 4.82 | 1.64 | 0.27 | 0.06 | 34.2 | 46.7 | 15.9 | 2.6 | 0.6 |
| BA2 | 4.17 | 1.63 | 1.84 | 0.58 | 0.07 | 0.05 | 39.0 | 44.0 | 13.9 | 1.8 | 1.3 |
| FW1 | 4.57 | 0.75 | 2.84 | 0.85 | 0.12 | 0.01 | 16.4 | 62.1 | 18.7 | 2.6 | 0.2 |
| FW2 | 3.23 | 0.80 | 2.01 | 0.37 | 0.04 | 0.01 | 24.6 | 62.2 | 11.6 | 1.3 | 0.3 |
| BI1 | 1.14 | 0.40 | 0.60 | 0.11 | 0.03 | 0.00 | 34.9 | 52.5 | 9.6 | 2.7 | 0.3 |
| BI2 | 7.51 | 2.37 | 3.83 | 1.10 | 0.15 | 0.06 | 31.6 | 51.0 | 14.6 | 2.0 | 0.8 |
| BPS1 | 11.33 | 5.34 | 3.73 | 1.28 | 0.87 | 0.11 | 47.1 | 32.9 | 11.3 | 7.7 | 1.0 |
| BPS2 | 36.44 | 9.33 | 16.17 | 7.81 | 2.93 | 0.20 | 25.6 | 44.4 | 21.5 | 8.0 | 0.5 |
| BPS2 | 1.21 | 0.31 | 0.63 | 0.24 | 0.03 | 0.00 | 25.4 | 51.8 | 19.4 | 2.7 | 0.7 |
| BE1 | 3.92 | 1.22 | 1.88 | 0.62 | 0.18 | 0.02 | 30.9 | 47.8 | 15.8 | 4.8 | 0.7 |
| BE2 | 10.55 | 2.92 | 6.04 | 0.93 | 0.57 | 0.09 | 27.7 | 57.2 | 8.9 | 5.4 | 0.8 |
| CM1 | 27.54 | 11.63 | 12.00 | 3.20 | 0.57 | 0.14 | 42.3 | 43.6 | 11.6 | 2.0 | 0.5 |
| DP1 | 1.00 | 0.29 | 0.55 | 0.09 | 0.07 | 0.00 | 28.9 | 54.4 | 8.2 | 7.7 | 0.8 |
| DP2 | 3.34 | 1.00 | 1.63 | 0.56 | 0.11 | 0.04 | 30.0 | 48.6 | 16.9 | 3.3 | 1.2 |
| DP3 | 0.86 | 0.23 | 0.53 | 0.07 | 0.03 | 0.00 | 26.5 | 60.9 | 7.8 | 4.3 | 0.5 |
| MC1 | 8.38 | 3.25 | 4.24 | 0.68 | 0.18 | 0.03 | 38.8 | 50.5 | 8.1 | 2.2 | 0.4 |
| DT1 | 3.47 | 1.39 | 1.22 | 0.77 | 0.06 | 0.03 | 40.0 | 34.9 | 22.3 | 1.8 | 1.0 |
| DT2 | 0.76 | 0.32 | 0.26 | 0.14 | 0.02 | 0.02 | 42.0 | 34.1 | 18.1 | 2.7 | 3.1 |

WBC: White blood cells
NEUT: Neutrophils
LYM: Lymphocytes
MONO: Monocytes
EOS: Eosinophils
BASO: Basophils Table 6 shows a summary of cells infused into each patient, including the date, patient weight on the day of the infusion, cells/kg infused, and remission status at the time of the first infusion and 4 weeks after the first infusion. The number after the patient indicates the infusion number.

sively of T cells that expressed CD5, CD8, and CD4 and the CD4:CD8 ratio (16:33) was reversed. The viability was determined to be 37%. These cells are at Day +21 of co-culture.

TABLE 6

Summary of Infused Cells in Patients

| Patient | Date | Wt (kg) | Cells/kg | Remission Status at Time of First Infusion | Remission Status 4 Weeks After First Infusion |
|---|---|---|---|---|---|
| BT 1 | Jun. 23, 2016 | 33.8 | 1.92E+05 | OOR | MR |
| CK 1 | Jun. 13, 2016 | 28.6 | 2.41E+05 | OOR | OOR |
| CK 2 | Jun. 16, 2016 | 28.6 | 2.80E+05 | OOR | OOR |
| CL 2 | Apr. 21, 2016 | 45.5 | 2.86E+05 | OOR | MR |
| BG 1 | Jun. 9, 2016 | 34.0 | 3.35E+05 | CR | CR |
| CL 2 | May 2, 2016 | 45.5 | 3.58E+05 | OOR | MR |
| BG 2 | Jun. 6, 2016 | 34.0 | 4.00E+05 | CR | CR |
| WS 3 | May 11, 2016 | 43.6 | 4.29E+05 | OOR | CR |
| WS 2 | Apr. 12, 2016 | 43.6 | 4.86E+05 | OOR | CR |
| MMO 1 | Jun. 6, 2016 | 16.0 | 4.88E+05 | CR | MR |
| TYC 1 | Jun. 20, 2016 | 12.3 | 5.04E+05 | MR | MR |
| RK 1 | Jul. 1, 2016 | 27.1 | 5.09E+05 | OOR | CR |
| CM 2 | May 26, 2016 | 30.0 | 5.53E+05 | OOR | MR |
| WS 1 | Mar. 30, 2016 | 43.6 | 5.60E+05 | OOR | CR |
| WS 4 | Jun. 25, 2016 | 43.6 | 6.10E+05 | OOR | CR |
| VS 2 | May 15, 2016 | 13.2 | 6.52E+05 | OOR | MR |
| MMO 2 | Jun. 9, 2016 | 16.0 | 6.75E+05 | OOR | MR |
| MMA 1 | Jun. 20, 2016 | 18.1 | 8.07E+05 | CR | MR |
| GS | Mar. 28, 2016 | 32.5 | 8.40E+05 | OOR | OOR |
| CL 1 | Apr. 18, 2016 | 45.5 | 8.60E+05 | OOR | MR |
| BT | Jun. 30, 2016 | 33.8 | 8.99E+05 | OOR | MR |
| CM 1 | May 23, 2016 | 30.0 | 1.00E+06 | CR | MR |
| TYC 2 | Jun. 23, 2016 | 12.3 | 1.05E+06 | MR | MR |
| GS | Mar. 25, 2016 | 32.5 | 1.37E+06 | OOR | D |
| MMA 2 | Jun. 23, 2016 | 18.1 | 1.48E+06 | CR | MR |
| MW 1 | May 23, 2016 | 10.0 | 1.51E+06 | OOR | CR |
| CK 3 | Jul. 6, 2016 | 28.6 | 1.62E+06 | OOR | OOR |
| RK 2 | Jul. 4, 2016 | 27.1 | 1.86E+06 | OOR | CR |
| BF 2 | Jun. 30, 2016 | 4.5 | 1.98E+06 | MR | MR |
| VS 1 | May 31, 2016 | 13.2 | 2.48E+06 | OOR | MR |
| SH 2 | Jul. 4, 2016 | 6.7 | 3.15E+06 | OOR | OOR |
| SH 1 | Jun. 30, 2016 | 6.7 | 3.54E+06 | OOR | OOR |
| SK 1 | Jul. 6, 2016 | 5.2 | 5.33E+06 | OOR | CR |
| BF 1 | Jun. 27, 2016 | 4.5 | 5.33E+06 | MR | MR |
| NF1 | Jan. 19, 2017 | 14.0 | 9.86E+05 | OOR | OOR |
| NF2 | Jan. 24, 2017 | 14.0 | 3.80E+06 | OOR | OOR |
| NF3 | Jan. 31, 2017 | 14.0 | 7.16E+06 | OOR | OOR |
| NF4 | Feb. 13, 2017 | 14.0 | 5.24E+06 | OOR | CR |
| NF5 | Feb. 15, 2017 | 14.0 | 1.02E+06 | CR | CR |
| NF6 | Feb. 20, 2017 | 14.0 | 3.67E+07 | OOR | CR |
| MC1 | Mar. 9, 2017 | 23.6 | 5.33E+06 | OOR | OOR |
| DT1 | Feb. 7, 2017 | 11.4 | 4.57E+06 | OOR | OOR |
| DT2 | Feb. 2, 2017 | 11.4 | 1.00E+06 | OOR | CR |
| DP1 | Feb. 7, 2017 | 12.7 | 1.18E+06 | MR | MR |
| CM1 | Mar. 16, 2017 | 25.0 | 1.65E+07 | CR | CR |
| BE1 | Mar. 15, 2017 | 12.7 | 1.25E+07 | OOR | CR |
| BE2 | Mar. 8, 2017 | 12.7 | 4.63E+06 | OOR | CR |
| BPS1 | Mar. 7, 2017 | 21.8 | 7.80E+06 | CR | MR |
| BPS2 | Mar. 15, 2017 | 21.8 | 2.51E+07 | MR | MR |
| BI1 | Mar. 9, 2017 | 21.6 | 5.22E+06 | OOR | CR |
| BI2 | Mar. 16, 2017 | 21.6 | 7.92E+05 | OOR | CR |
| FW1 | Apr. 19, 2017 | 16.8 | 2.88E+06 | CR | MR |
| FW2 | Apr. 25, 2017 | 16.8 | 4.08E+06 | MR | MR |
| BA1 | May 11, 2017 | 27.7 | 2.26E+06 | CR | CR |
| BA2 | May 18, 2017 | 27.7 | 5.59E+06 | CR | CR |
| CA1 | Apr. 19, 2017 | 31.8 | 3.35E+05 | CR | MR |
| CA2 | May 24, 2017 | 31.8 | 6.93E+05 | CR | MR |

OOR: Out of remission
CR: Clinical remission
MR: Molecular remission

FIG. 13 shows the T cell population, which was infused into patient GS. Flow cytometry was used to determine that the cell population consisted of a homogenous population of small lymphoid cells. Non-lymphoid cells were identified to be non-viable or cell debris. Lymphocytes consisted exclu- The effects of antigen specific cell infusion were demonstrated in patient CL. This patient was in the process of failing remission at the time of apheresis harvest collection. The harvest was PCR+ for the presence of lymphoma, as was the circulating blood of the patient at the time of collection. Cell cultures also developed tumor colonies, which were determined by PCR to be B cell lymphoma. Sufficient flasks and wells in which T cells had grown were obtained and administered in 3 separate infusions.

Figure 10:
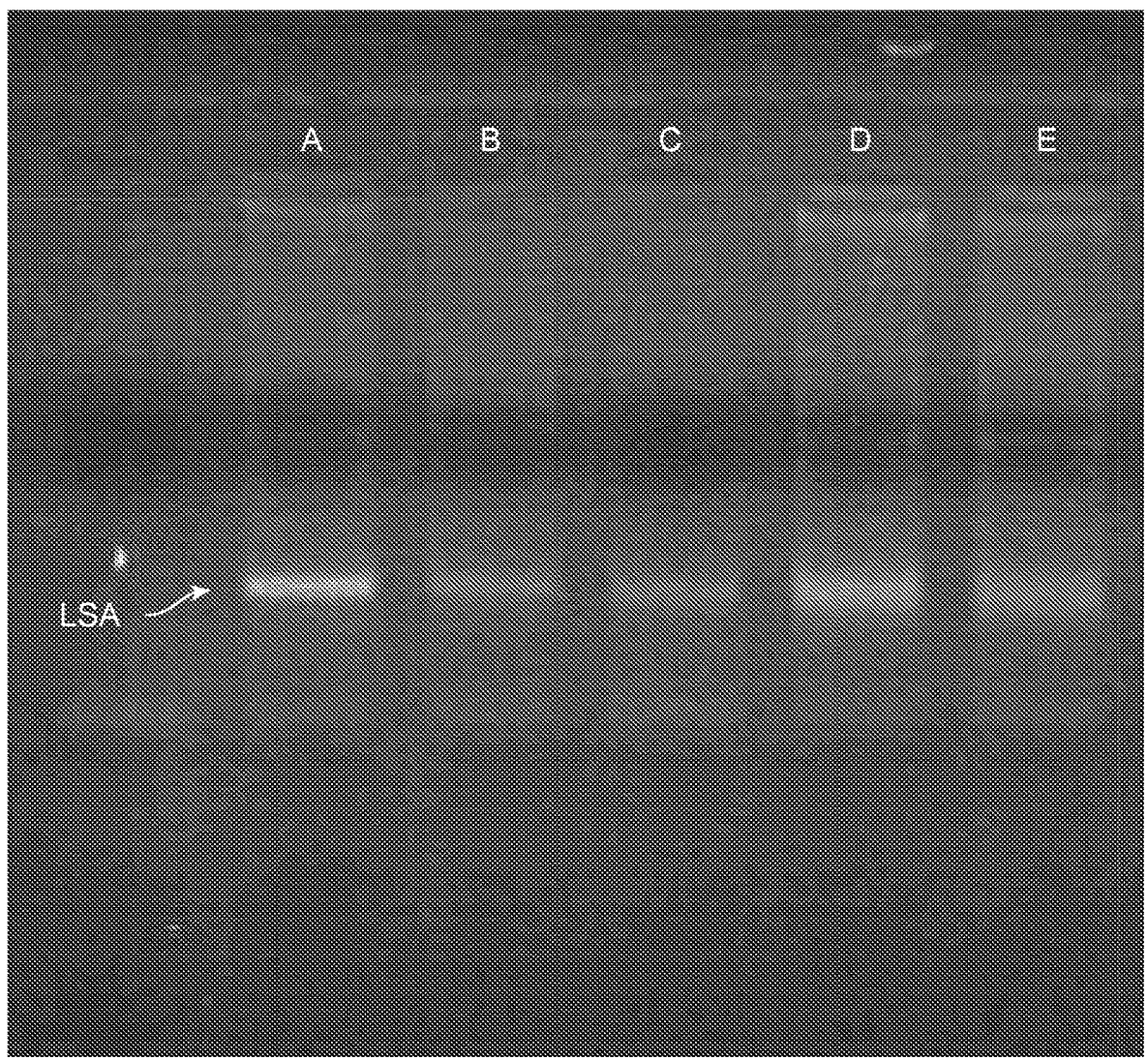
FIG. 10 shows the results of the PCR analysis from patient CL's apheresis harvest by DNA gel electrophoresis. The white arrow indicates the position of a positive band of LSA (lymphosarcoma) in each lane. A positive band indicates the presence of an overabundance of clonal B cells. Lane A shows the apheresis harvest and lane B shows CL's peripheral blood prior to ACT infusion. Lane C shows the peripheral blood prior to the second ACT infusion and Lane D shows the peripheral blood prior to the third ACT infusion. Lane E shows the peripheral blood of patient CL after the third infusion on Day 14. Lanes C, D, and E are all negative.
Figure 23:
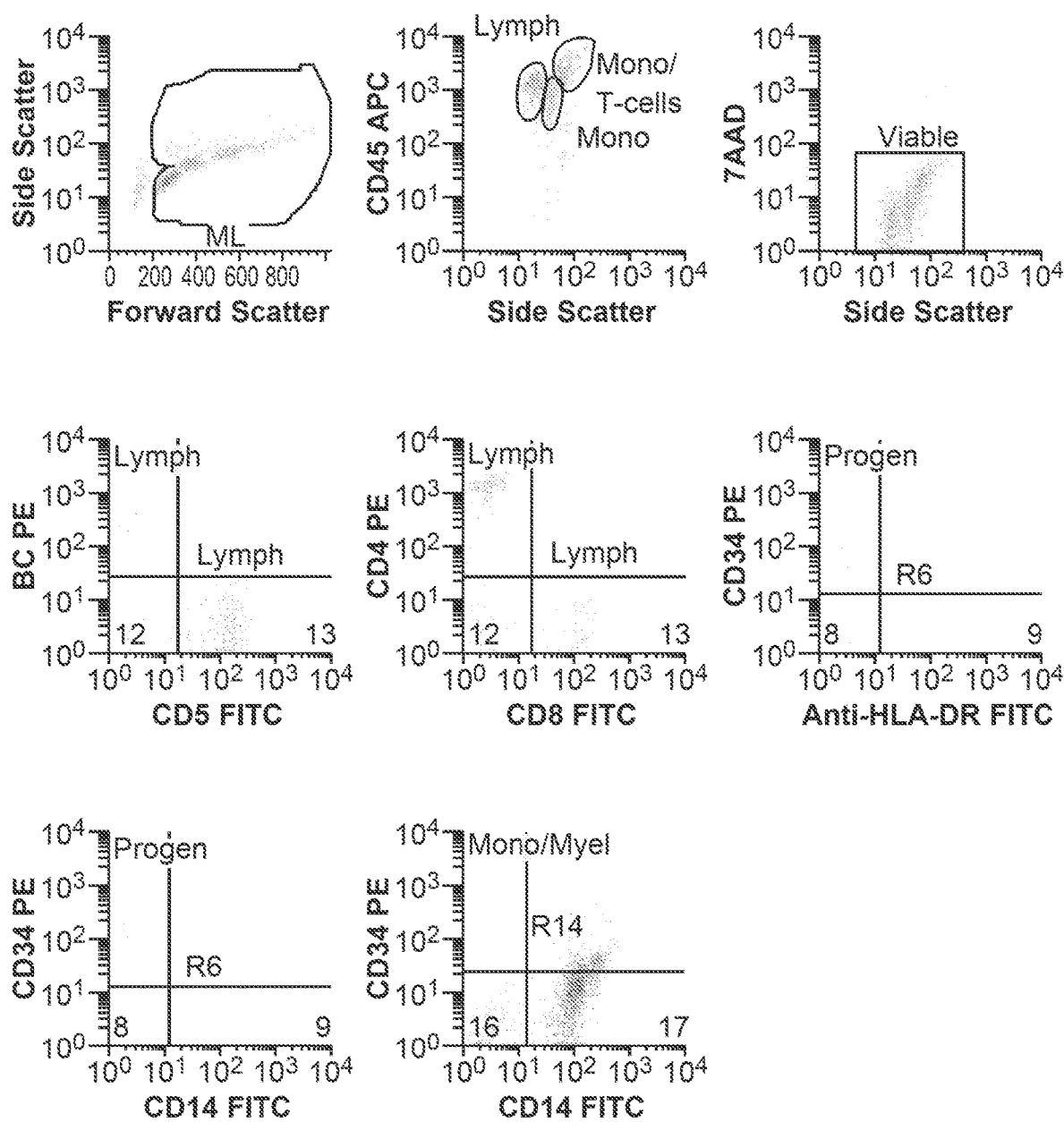
FIG. 23 shows flow cytometry dot plots of cell populations from the apheresis harvest of patient CL.

PCR analysis was performed on blood from the patient prior to infusion #1, and before each subsequent dose. FIG. 10 shows the results of the PCR analysis of patient CL's apheresis harvest (lane A), blood prior to infusion #1 (lane B), prior to subsequent infusions (lanes C and D), and prior to the most recent subsequent infusion (lane E). PCR results showed that the blood of patient CL, which was strongly positive in the apheresis harvest (which comprises concentrated white blood cells) and clearly positive in circulating blood prior to administration, became and stayed negative post-infusion, demonstrating efficacy. FIG. 23 shows the cell populations from the apheresis harvest of patient CL. As measured by flow cytometry, patient CL had an apheresis product composition of 16% lymphocytes and 69% myeloid/monocytes. Independent immunophenotypic analysis revealed 0.2% progenitor cells, including some monocytes. The viability was 86%. The patient has remained CR and MR at 16 months post-infusion.

Figure 19:
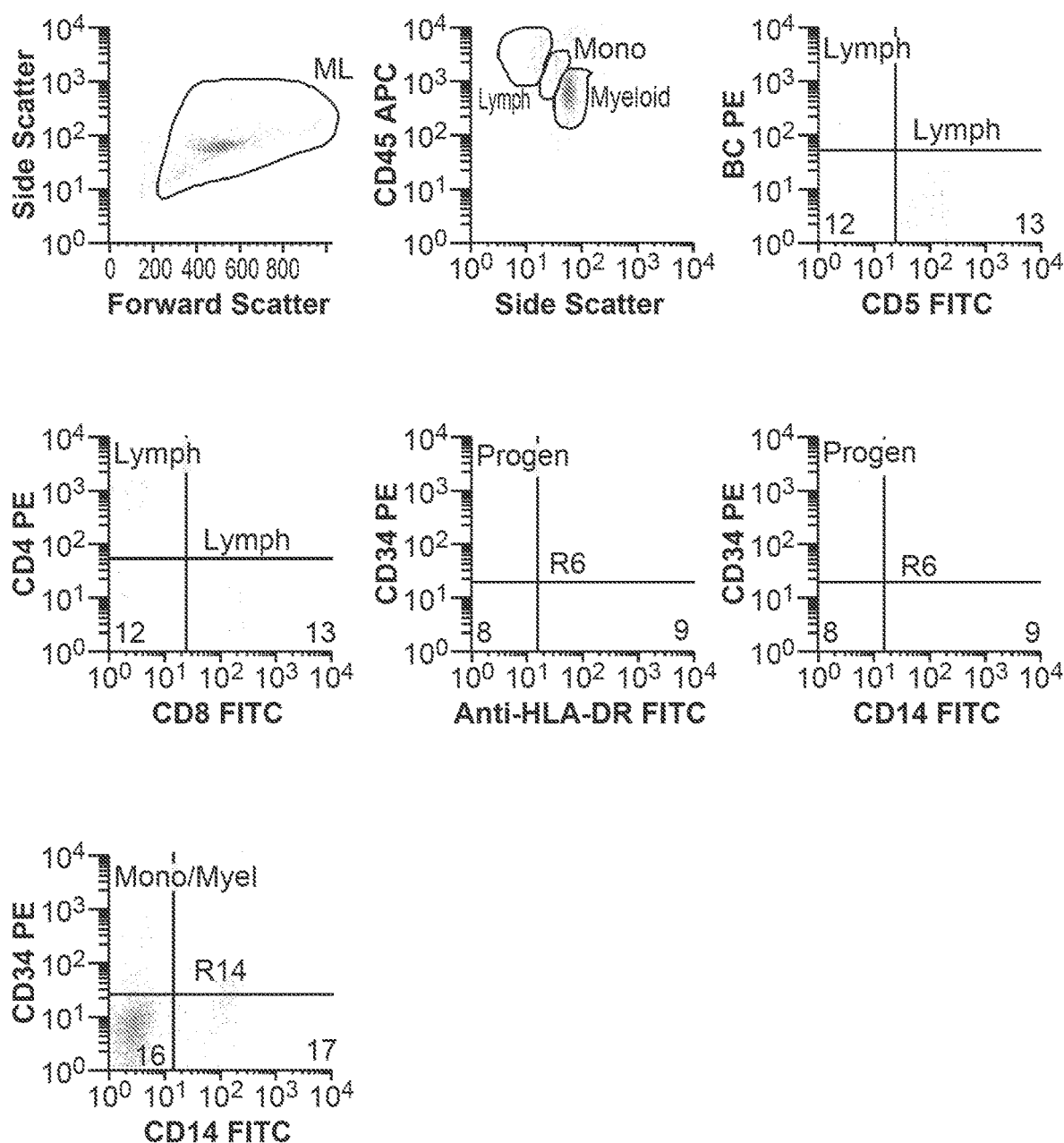
FIG. 19 shows flow cytometry dot plots of cell populations in the peripheral blood of patient CL prior to the first ACT infusion.
Figure 20:
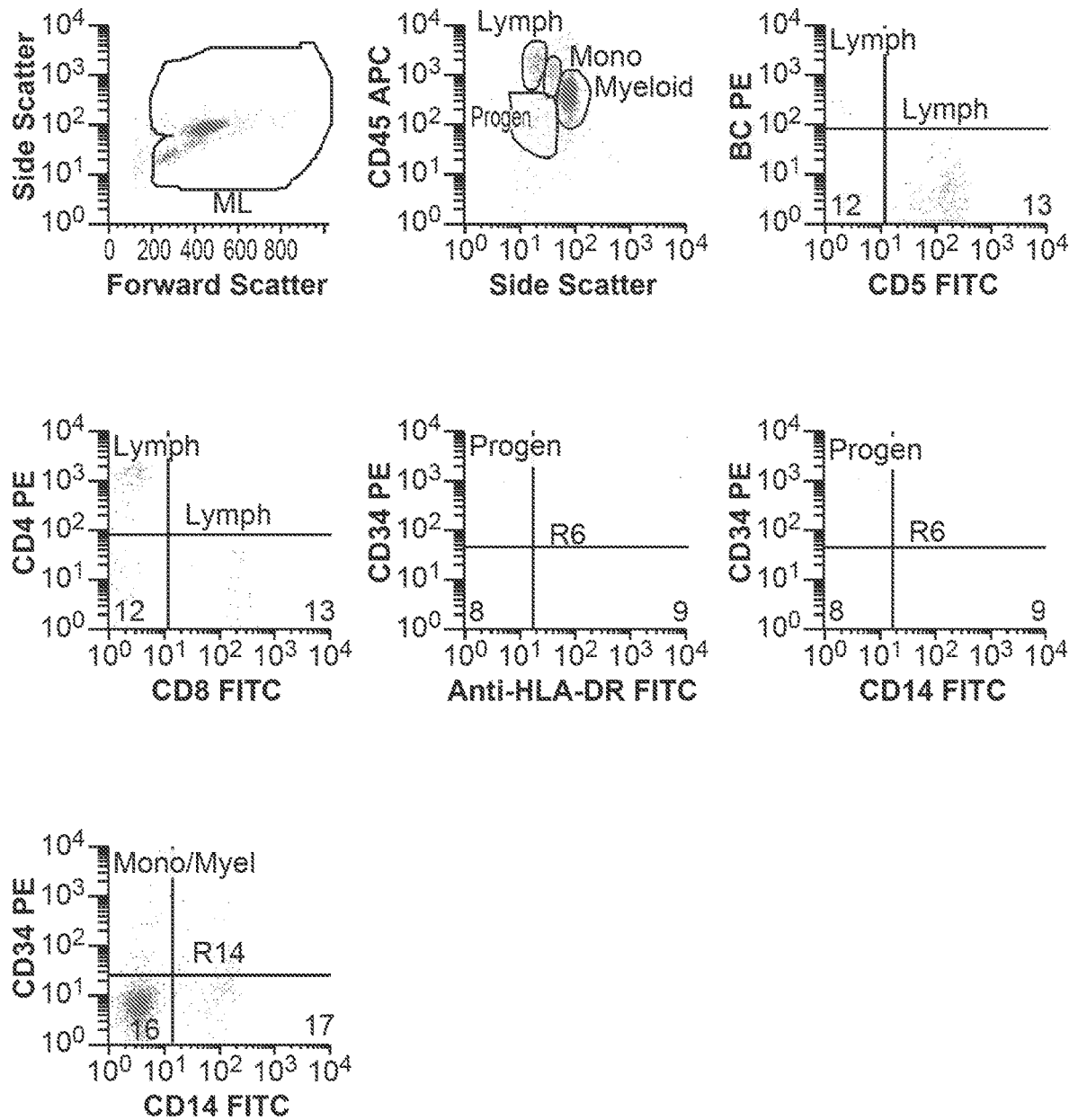
FIG. 20 shows flow cytometry dot plots of cell populations in the peripheral blood of patient CL after the first ACT infusion.

FIG. 19 shows the cell populations from peripheral blood from patient CL, prior to the first T cell infusion. As measured by flow cytometry, patient CL had a peripheral blood cell composition of 0.9% normal lymphocytes and 88% myeloid/monocytes. No abnormal cells were noted at this time. Independent immunophenotypic analysis revealed a small population of normal lymphoid cells. B cells comprised 5.3% of the cell population and appeared normal. T lymphoid cells comprised 92% of the cell population and expressed mature antigens. The CD4:CD8 ratio (57:23) was determined to be normal FIG. 20 shows the cell populations from peripheral blood from patient CL, after the first T cell infusion. Flow cytometry was used to determine that peripheral blood cells were comprised of 6% lymphocytes, 10% monocytes, and 74% myeloid cells. No abnormal lymphocytes were noted. Independent immunophenotypic analysis revealed a small population of normal lymphoid cells. The B cells comprised 3.5% of the cell population and appeared normal. The T lymphoid cells comprised 96% of the cell population and expressed mature antigens.

Figure 21:
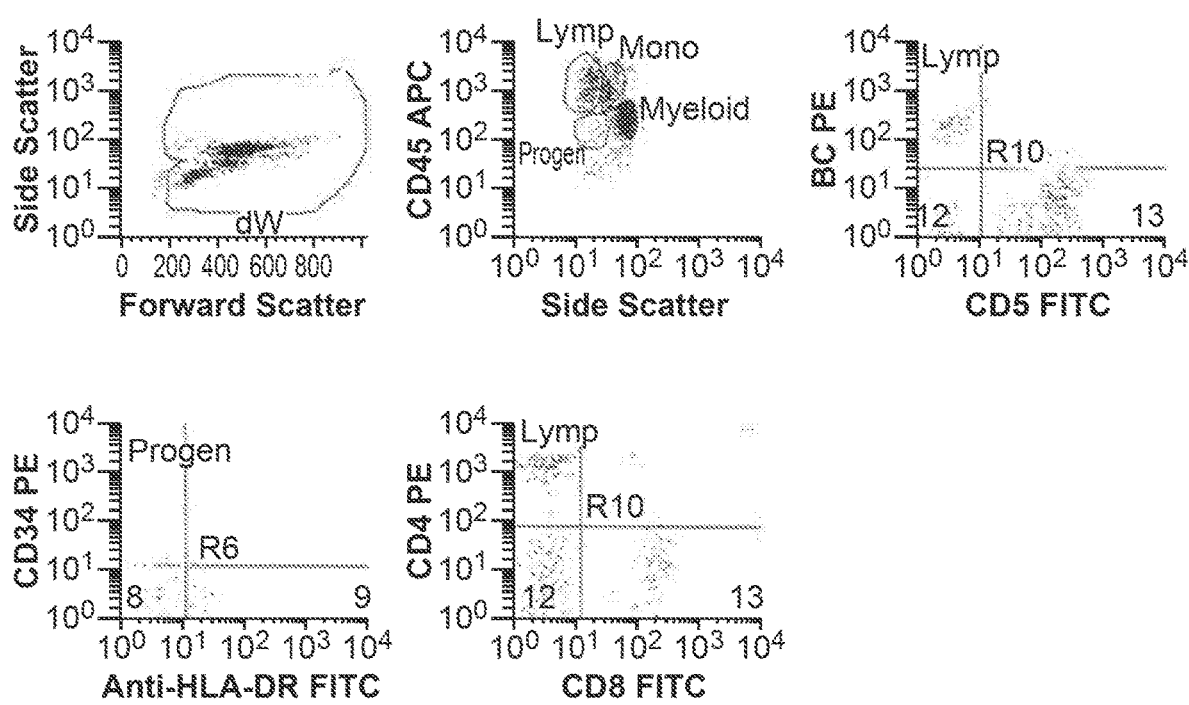
FIG. 21 shows flow cytometry dot plots of cell populations in the peripheral blood of patient CL after the third ACT infusion.

FIG. 21 shows cell populations from peripheral blood from patient CL after the third T cell infusion. Flow cytometry was used to determine that peripheral blood cells were comprised of 7.8% lymphocytes, 7.7% monocytes, and 58% myeloid cells. No abnormal lymphocytes were noted. Independent immunophenotypic analysis revealed a small population of normal lymphoid cells. B cells comprised 1.1% of the cell population and appeared normal. The T lymphoid cells comprised 78% of the cell population and expressed mature antigens. The CD4:CD8 ratio (44:21) was determined to be normal.

Figure 22:
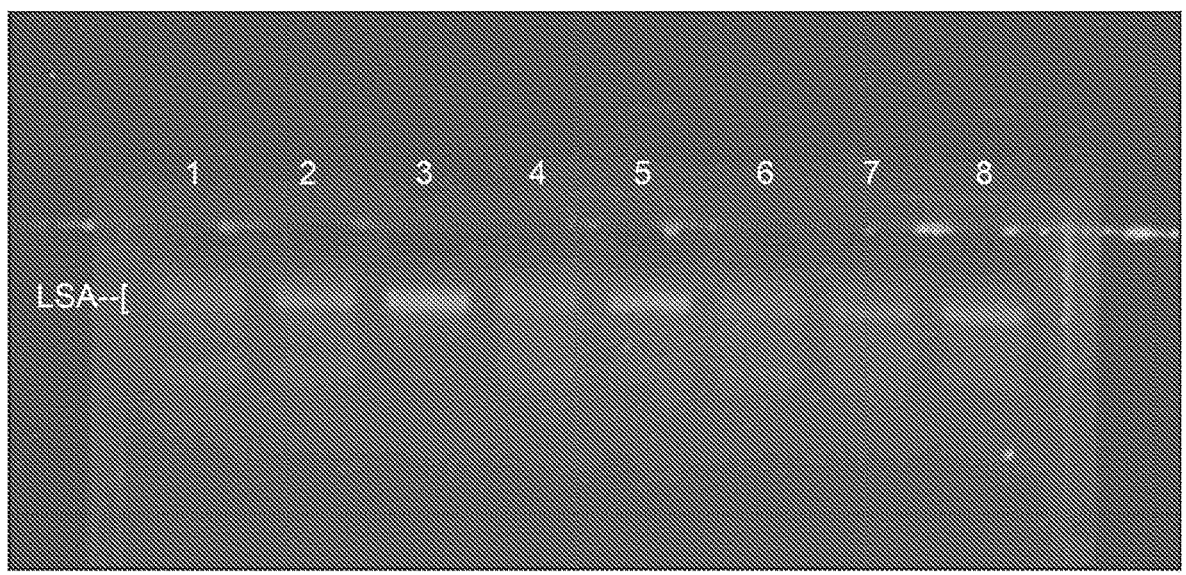
FIG. 22 shows the results of PCR analysis of patient BT prior to and over the course of ACT infusions by DNA gel electrophoresis. The white bracket indicates the position of a positive lymphosarcoma (LSA) band in each lane. The positive band indicates the presence of an overabundance of clonal B cells. Lane 1 shows the peripheral blood of patient BT after three ACT infusions. Lanes 2, 3, 5, and 7 show positive controls of peripheral blood from other positive patients. Lanes 4 and 6 show negative controls of peripheral blood from other negative patients. Lane 8 shows the peripheral blood of patient BT prior to ACT infusion.

FIG. 22 shows the results of the PCR analysis of patient BT's peripheral blood after three infusions (lane 1) and prior to infusion (lane 8). Peripheral blood from other positive patients (lanes 2, 3, 5, 7) and negative patients (lanes 4, 6) are also shown.

A different patient, VS, was failing remission at the time of blood collection and cultures were positive for B cell lymphoma colonies and bacteremia. A first ACT infusion (coupled with doses of L-Asparaginase) was administered and the patient was in CR and MR in status at least 45 days post-infusion. Patient VS then went off protocol and received vincristine and prednisone by a different care provider, and after two weeks was OOR. A PCR exam of the aspirate did not identify a clonal population of B cells, nor did a peripheral blood sample. VS had disease progression and died.

Patient WS, which was an osteosarcoma (OS) case, received multiple infusions and had moderate to slow growth of the primary bone mass. To date, no metastatic disease has been detected, and the patient remains in good health after having a limb-sparing surgical procedure. WS had disease progression and died five months post infusion.

Patient MW, the only case in which T cells were raised from cryopreserved harvest, received two infusions, but had disease progression and the additional burden of T cell lymphoma leading to death.

In all subjects, the infusions were well tolerated, with no immediate reactions or long term deleterious effects noted. These studies indicated the number of T cells that can be infused, and which were safe and efficacious in a clinical setting.

Example 7

Treatment of a Cancer with Antigen Specific Cell Infusion

This example describes the use of antigen specific cell infusion of the disclosure to treat cancer. CD8+ T cells with anti-cancer specificity and anti-cancer activity are stimulated and expanded by antigen presenting feeder cells that are transduced and transfected with a cancer target antigen as described in EXAMPLE 1.

The antigen specific cells of the disclosure are administered to a subject in need thereof. The administration is done via peripheral vein infusion. The subject is a mammal, such as a canine, a feline, or a human.

An antigen specific cell infusion is administered to a subject in need thereof. The antigen specific cell infusion is administered before, co-administered, or administered after delivery of chemotherapeutic agents such as cyclophosphamide, doxorubicin, vincristine, L-Asparaginase, or any combination thereof. The antigen specific cell infusion is administered before, co-administered, or administered with a steroid, such as prednisone.

Infusion of antigen specific cells in a subject in need thereof results in anti-cancer activity, and long-term immunologic memory is established against cancer cells.

Example 8

Treatment of B Cell Lymphoma with an Antigen Specific Cell Infusion

This example describes the use of antigen specific cell infusion of the disclosure to treat B cell lymphoma. CD8+ T cells with anti-cancer specificity and anti-cancer activity are stimulated and expanded by antigen presenting feeder cells that are transduced and transfected as described in EXAMPLE 1.

The antigen specific cells of the disclosure are administered to a subject in need thereof. The administration is done via infusion. The subject is a mammal, such as a canine, feline, or a human.

An antigen specific cell infusion is administered to a subject in need thereof. The antigen specific cell infusion is administered before, co-administered, or administered after delivery of chemotherapeutic agents such as cyclophosphamide, doxorubicin, vincristine, L-asparaginase, or any combination thereof. The antigen specific cell infusion is administered after a steroid, such as prednisone.

Infusion of antigen specific cells in a subject in need thereof results in anti-B cell lymphoma cancer activity, and long-term immunologic memory is established against B cell lymphoma cancer cells.

Example 9

Treatment of Osteosarcoma with an ACT of the Disclosure

This example describes the use of antigen specific cell infusion of the disclosure to treat osteosarcoma. CD8+ T cells with anti-cancer specificity and anti-cancer activity are stimulated and expanded by antigen presenting feeder cells that are transduced and transfected as described in EXAMPLE 1.

The antigen specific cells of the disclosure are administered to a subject in need thereof. The administration is done via infusion. The subject is a mammal, such as a canine, feline, or a human.

An antigen specific cell infusion is administered to a subject in need thereof. The antigen specific cell infusion is administered before, co-administered, or administered after delivery of chemotherapeutic agents such as methotrexate, doxorubicin, cisplastin, or any combination thereof.

Infusion of antigen specific cells in a subject in need thereof results in anti-osteosarcoma cancer activity, and long-term immunologic memory is established against osteosarcoma cancer cells.

Example 10

Treatment of Hemangiosarcoma with an ACT of the Disclosure

This example describes the use of antigen specific cell infusion of the disclosure to treat hemangio sarcoma. CD8+ T cells with anti-cancer specificity and anti-cancer activity are stimulated and expanded by antigen presenting feeder cells that are transduced and transfected as described in EXAMPLE 1.

The antigen specific cells of the disclosure are administered to a subject in need thereof. The administration is done via infusion. The subject is a mammal, such as a canine, feline, or a human.

An antigen specific cell infusion is administered to a subject in need thereof. The antigen specific cell infusion is administered before, co-administered, or administered after delivery of chemotherapeutic agents such as cyclophosphamide or doxorubicin.

Infusion of antigen specific cells in a subject in need thereof results in anti-hemangio sarcoma cancer activity, and long-term immunologic memory is established against hemangiosarcoma cancer cells.

Example 11

Treatment of Multiple Myeloma with an ACT of the Disclosure

This example describes the use of antigen specific cell infusion of the disclosure to treat multiple myeloma. CD8+ T cells with anti-cancer specificity and anti-cancer activity are stimulated and expanded by antigen presenting feeder cells that are transduced and transfected as described in EXAMPLE 1.

The antigen specific cells of the disclosure are administered to a subject in need thereof. The administration is done via peripheral vein infusion. The subject is a mammal, such as a canine, feline, or a human.

An antigen specific cell infusion is administered to a subject in need thereof. The antigen specific cell infusion is administered before, co-administered, or administered after delivery of chemotherapeutic agents such as cyclophosphamide, doxorubicin, vincristine, or any combination thereof. The antigen specific cell infusion is administered before, co-administered, or administered with a steroid, such as prednisone.

Infusion of antigen specific cells in a subject in need thereof results in anti-multiple myeloma cancer activity, and long-term immunologic memory is established against multiple myeloma cancer cells.

Example 12

Treatment of a Plasma Cell Tumor with an ACT of the Disclosure

This example describes the use of antigen specific cell infusion of the disclosure to treat a plasma cell tumor. CD8+ T cells with anti-cancer specificity and anti-cancer activity are stimulated and expanded by antigen presenting feeder cells that are transduced and transfected as described in EXAMPLE 1.

The antigen specific cells of the disclosure are administered to a subject in need thereof. The administration is done via infusion. The subject is a mammal, such as a canine, feline, or a human.

An antigen specific cell infusion is administered to a subject in need thereof. The antigen specific cell infusion is administered before, co-administered, or administered after delivery of chemotherapeutic agents such as cyclophosphamide, doxorubicin, and vincristine. The antigen specific cell infusion is administered before, co-administered, or administered with a steroid, such as prednisone.

Infusion of antigen specific cells in a subject in need thereof results in anti-plasma cell tumor activity, and long-term immunologic memory is established against plasma cell tumors.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method of expanding a CD20 antigen specific cell, the method comprising:
   contacting a first cell with a feeder cell in a co-culture comprising a population of allogeneic tumor cell membrane extracts to produce the CD20 antigen specific cell from the first cell,
   wherein the feeder cell presents a recombinant CD20 selected from the group consisting of a recombinant canine CD20 or a recombinant feline CD20 and
   wherein the population of allogeneic tumor cell membrane extracts is generated by exposing a population of allogeneic tumor cells to a plurality of freeze/thaw cycles to disrupt the allogenic tumor cells, centrifuging the resulting cells, and collecting at least a portion of the resulting pellet for addition to the co-culture.

2. The method of claim 1, further comprising isolating the feeder cell from whole peripheral blood by density centrifugation.

3. The method of claim 1, further comprising adding an interleukin mixture comprising interleukin 21, interleukin 2, phytohemagglutinin, anti-CD3 antibody, or any combination thereof.

4. The method of claim 1, further comprising adding interleukin 21 at least three times in a first week of the co-culture.

5. The method of claim 1, further comprising co-administering interleukin 21 and interleukin 2 three times a week starting in a second week of the co-culture.

6. The method of claim 5, further comprising adding the interleukin 2 to the co-culture at least three times a week in a second week of the co-culture, a third week of the co-culture, a fourth week of the co-culture, a fifth week of the co-culture, a sixth week of the co-culture, or any combination thereof.

7. The method of claim 1, wherein the CD20 antigen specific cell is a T cell.

8. The method of claim 1, wherein the recombinant thereof comprises at least 80% sequence identity to SEQ ID NO: 1 or SEQ ID NO: 3.

9. The method of claim 1, wherein the feeder cell is an antigen presenting cell comprising a dendritic cell, a macrophage, or a B cell.

10. The method of claim 9, wherein the antigen presenting cell is derived from a chronic lymphocytic leukemia cell line.

11. The method of claim 1, wherein the feeder cell further expresses at least one human cell surface molecule comprising CD19, CD64, CD86, CD137L, membrane bound IL-15, or any combination thereof.

12. The method of claim 1, wherein the feeder cell is heat killed or irradiated by a direct dose of gamma radiation.

13. The method of claim 1, wherein the feeder cell is transfected with a nucleotide sequence encoding the recombinant CD20.

14. The method of claim 1, wherein the feeder cell expresses a human cell surface molecule comprising CD19, CD64, CD86, CD137L, membrane bound IL-15, or any combination thereof.

15. The method of claim 1, wherein exposing the population of allogenic tumor cells to a plurality of freeze/thaw cycles comprises exposing the population of allogeneic tumor cells to $-120°$ C. for 5 minutes then thawing the population to $37°$ C.

16. The method of claim 1, wherein the feeder cell is mixed with a human anti-CD3 antibody.

17. A method of treating a subject in need thereof comprising:
generating a CD20 antigen specific cell by contacting a cell with an allogeneic tumor cell membrane extract and a feeder cell presenting a recombinant canine CD20 or a recombinant feline CD20; and
administering the CD20 antigen specific cell to a subject in need thereof,
wherein the CD20 antigen specific cell is selected from the group consisting of a canine CD20 antigen specific cell and a feline CD20 antigen specific cell, and
wherein the allogeneic tumor cell membrane extract is generated by exposing a population of allogeneic tumor cells to a plurality of freeze/thaw cycles to disrupt the allogenic tumor cells, centrifuging the resulting cells, and contacting the cell with at least a portion of the resulting pellet.

18. The method of claim 17, wherein the administering is an infusion via a peripheral vein catheter.

19. The method of claim 17, wherein the administering comprises a first dose infused at a rate of from $5\times10^5$ cells/m$^2$ to $5\times10^{10}$ cells/m$^2$.

20. The method of claim 19, wherein the administering further comprises a second dose infused two weeks after the first dose, infused at a rate of from $5\times10^5$ to $5\times10^{10}$ cells/m$^2$.

21. The method of claim 17, further comprising conditioning the subject with a chemotherapy before the administering.

22. The method of claim 17, wherein the subject is a canine.

23. The method of claim 17, further comprising killing a cancer cell from a B cell lymphoma with the antigen specific cell.

24. The method of claim 17, wherein the subject has a B cell lymphoma, a T cell lymphoma, an osteosarcoma, a hemangiosarcoma, multiple myeloma, or a plasma cell tumor.

25. The method of claim 17, wherein the subject is a human.

* * * * *